( 12 ) United States Patent
Qu

(10) Patent No.: US 7,962,290 B1
(45) Date of Patent: Jun. 14, 2011

(54) IDENTIFICATION OF PHARMACOPHORES FROM CO-CRYSTALS OF SPLEEN TYROSINE KINASE (SYK) AND SYK LIGANDS

(75) Inventor: Kunbin Qu, Palo Alto, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1047 days.

(21) Appl. No.: 11/651,363

(22) Filed: Jan. 9, 2007

Related U.S. Application Data

(60) Provisional application No. 60/757,545, filed on Jan. 9, 2006.

(51) Int. Cl.
*G01N 33/48* (2006.01)
*G01N 31/00* (2006.01)
*G01N 33/53* (2006.01)
*G06G 7/58* (2006.01)

(52) U.S. Cl. ............. 702/19; 702/27; 703/11; 435/7.71
(58) Field of Classification Search ........................ None
See application file for complete search history.

(56) References Cited

U.S. PATENT DOCUMENTS

| | | | |
|---|---|---|---|
| 5,756,466 A | 5/1998 | Bemis et al. | |
| 2002/0067800 A1 | 6/2002 | Newman et al. | |
| 2004/0253178 A1 | 12/2004 | Atwell et al. | |

FOREIGN PATENT DOCUMENTS

WO WO 2004/035604 A2 4/2004

OTHER PUBLICATIONS

Matsubara et al. (American Journal of Respiratory and Critical Care Medicine, vol. 173, pp. 56-63, 2006, published ahead of print on Sep. 28, 2005).*
Rigel Pharmaceuticals (Retrieved from the Internet: <http://www.rigel.com/rigel/pr_1078950345>, Retrieved on Oct. 28, 2010).*
Matsubara et al. (Syk Activation in Dendritic Cells Is Essential for Airway Hyperresponsiveness and Inflammation, Am J Respir Cell Mol Biol, 34(4):426-33, published on Dec. 9, 2005).*
Braselmann et al. (The Journal of Pharmacology and Experimental Therapeutics vol. 319, No. 3, pp. 998-1008, 2006).*
Yanagi et al., Biochem. Biophys. Res. Comm. 288:495-498 (2001).
Atwell et al., J. Biol. Chem. 279 (53):55827-55832 (2004); PDB ID:1XBA, 1XBB and 1XBC.
Lemmen C. and Lengauer T., Computational methods for the structural alignment of molecules, J. Comput. Aided Mol. Des. 14(3):215-32 (2000).
Guner O., Clement O. and Kurogi Y., Pharmacophore modeling and three dimensional database searching for drug design using catalyst: recent advances, Curr. Med. Chem. 11(22):2991-3005 (2004).
Yamamoto N., Takeshita K., Shichijo M., Kokubo T., Sato M., Nakashima K., Ishimori M., Nagai H., Li Y.F., Yura T., Bacon K.B. . The orally available spleen tyrosine kinase inhibitor 2-[7-(3,4-dimethoxyphenyl)-imidazo[1,2-c]pyrimidin-5- ylamino]nicotinamide dihydrochloride (BAY 61-3606) blocks antigen-induced airway inflammation in rodents, J. Pharmacol. Exp. Ther. 306(3):1174-81 (2003).
Eisenberg et al. (1984) J. Mol. Biol. 179:125-42.
Lovell S.C., Word J.M., Richardson J.S. and Richardson D.C., The Penultimate Rotamer Library, Proteins: Structure Function and Genetics 40 389-408 (2000).
McPherson, Eur. J. Biochem. 189:1-23, 1990.
Weber, Adv. Protein Chem. 41:1-36, 1991; Methods in Enzymology 276:13-22, 100-110; 131-143, Academic Press, San Diego, 1997.
Matthews, J. Mol. Biol. 33(2):491-97, 1968.
Lattman, Methods in Enzymology 115:55-77, 1985.
Hendrickson, Science, 254:51-58, 1991.
Brodersen, et al., Acta Cryst., D56:431-41, 2000.
North, Acta Cryst. 18:212-16, 1965.
MDL Information Systems, Inc.; Dalby, et al., J. Chem. Inf. Comp. Sci., 32:244-55, 1992.
Weininger, J. Chem. Inf. Comp. Sci. 28:31-36, 1988.
Travis, Science, 262:1374, 1993.
Meng, et al., J. Comp. Chem. 13:505-24, 1992.
SYK (Blaney, J. M. and Dixon, J. S., Perspectives in Drug Discovery and Design, 1:301, 1993).
CE (Shindyalov, Ind., Bourne, P E, "Protein Structure Alignment by Incremental Combinatorial Extension (CE) of the Optimal Path," Protein Engineering, 11:739-47, 1998).
Charmm (Brooks, et al., J. Comp. Chem. 4:187-217, 1983).
Dock (Kuntz et al., J. Mol. Biol., 161:269-88, 1982; DOCK is available from University of California, San Francisco, Calif.).
AUTODOCK (Goodsell & Olsen, Proteins: Structure, Function, and Genetics 8:195-202, 1990; AUTODOCK is available from Scripps Research Institute, La Jolla, Calif.).
GOLD (Cambridge Crystallographic Data Centre (CCDC); Jones et al., J. Mol. Biol. 245:43-53, 1995).
FLEXX (Tripos, St. Louis, Mo.; Rarey, M., et al., J. Mol. Biol. 261:470-89, 1996).
Amber (Weiner, et al., J. Am. Chem. Soc. 106: 765-84, 1984) and C2 MMFF (Merck Molecular Force Field; Accelrys, San Diego, Calif.).
Eldridge, et al., J. Comput. Aided Mol. Des. 11:425-45, 1997; Schrodinger, Inc., New York.
MDL Information Systems, San Leandro, Calif.); HOOK (Eisen et al., Proteins: Struct., Funct., Genet., 19:199-221, 1994).
Bohm, J. Comp. Aid. Molec. Design 6:61-78, 1992; and available from Accelrys, Inc., San Diego, Calif.
Cohen et al., J. Med. Chem. 33:883-94, 1990.
Guida, Curr. Opin. Struct. Biol. 4:777-81, 1994.
Klebe, G., J. Mol. Med. 78:269-81, 2000).

(Continued)

*Primary Examiner* — Suzanne M Noakes
*Assistant Examiner* — Jae W Lee
(74) *Attorney, Agent, or Firm* — Travis Young; McDonnell Boehnen Hulbert & Berghoff LLP

(57) ABSTRACT

The invention comprises for methods of identifying pharmacophores based on the spleen tyrosine kinase (SYK) protein or fragment thereof. The invention further provides methods of identifying SYK inhibitors using pharmacophores that are identified from co-crystals of SYK and its ligands. Further, the invention comprises methods of inhibiting SYK comprising contacting the residues lining the binding site with an inhibitor compound identified from pharmacophores.

29 Claims, 32 Drawing Sheets
(24 of 32 Drawing Sheet(s) Filed in Color)

OTHER PUBLICATIONS

Hol. W. G. J., Angewandte Chemie (Int'l Edition in English) 25:767-852, 1986.

Gane, P. J. and Dean, P. M., Current Opinion in Structural Biology, 10:401-04, 2000.

Maignan, S. and Mikol, V., Curr. Top. Med. Chem. 1: 161-174 (2001).

Z. Otwinowski and W. Minor, "Processing of X-ray Diffraction Data Collected in Oscillation Mode", Methods in Enzymology, vol. 276: Macromolecular Crystallography, part A, p. 307-326, (1997), C.W. Carter, Jr. & R. M. Sweet, Eds., Academic Press (New York).

A.A. Vagin and E.J. Dodson, in Acta Cryst. D53, 240, (1997).

T.A Jones, J.Y Zou, S.W. Cowan, and M. Kjeldgaard, Acta. Cryst. A47, 110, (1991).

Cohen et al., "Molecular modeling software and methods for medicinal chemistry," J. Med. Chem. 33: 883-94, 1990.

George et al., "[6] Second virial coefficient as predictor in protein crystal growth," Methods in Enzymology 276: 100-110, 1997.

Lattman, "Diffraction methods for biological macromolecules. Use of the rotation and translation functions," Methods in Enzymology 115: 55-77, 1985.

Matthews, "The extension of the isomorphous replacement method to include anomalous scattering measurements," Acta Cryst. 20: 82-86, 1966.

McPherson, "Current approaches to macromolecular crystallization," Eur. J. Biochem. 189:1-23, 1990.

McPherson, Crystallization of Biological Macromolecules, Cold Spring Harbor Press, New York, 1998. [Table of Contents.].

Navia & Murcko, "Use of structural information in drug design," Current Opinion in Structural Biology 2:202-10, 1992.

North, "The combination of isomorphous replacement and anomalous scattering data in phase determination of noncentrosymmetric reflexions," Acta Cryst. 18: 212-16, 1965.

Protein Data Bank ID: 1XBA, "Crystal structure of apo syk tyrosine kinase domain," printed on Sep. 8, 2010.

Protein Data Bank ID: 1XBB, "Crystal structure of the syk tyrosine kinase domain with Gleevec," printed on Sep. 8, 2010.

Protein Data Bank ID: 1XBC, "Crystal structure of the syk tyrosine kinase domain with Staurosporin," printed on Sep. 8, 2010.

Rossmann, The Molecular Replacement Method, Int. Sci. Rev. Ser. No. 13, Gordon & Breach, New York, 1972. [Table of Contents.].

Sousa, "[8] Using cosolvents to stabilize protein conformation for crystallization," Methods in Enzymology 276: 131-143, 1997.

Terwilliger, "[30] Multiwavelength anomalous diffraction phasing of macromolecular structures: Analysis of MAD data as single isomorphous replacement with anomalous scattering data using the MADMRG program," Methods in Enzymology 276: 530-37, 1997.

Vagin and Teplyakov, "MOLREP: an Automated Program for Molecular Replacement," J. Appl. Cryst. 30: 1022-5, 1997.

Weber, "[2] Overview of protein crystallization methods," Methods in Enzymology 276: 13-22, 1997.

Weber, "Physical principles of protein crystallization," Adv. Protein Chem. 41:1-36, 1991.

\* cited by examiner

MW markers top to bottom- 200 kDa, 116.25 kDa, 97.4 kDa, 66.2 kDa, 45 kDa, 31kDa 1- MW markers
2- Lysate
3- Flow through
4- Flow through
5- 1$^{st}$ gradient (0% to 5% 500mM imidazole)
6- Elution fraction
7- Elution fraction
8- Elution fraction
9- Elution fraction
10- Elution fraction
11- Elution fraction (100% of 500mM imidazole)
12- Elution fraction (100% of 500mM imidazole)

IDENTIFICATION OF PHARMACOPHORES FROM CO-CRYSTALS OF SPLEEN TYROSINE KINASE (SYK) AND SYK LIGANDS

CROSS-REFERENCE TO RELATED APPLICATIONS

This application claims benefit to U.S. Provisional Application No. 60/757,545 filed Jan. 9, 2006.

DESCRIPTION OF THE COMPACT DISK-RECORDABLE (CD-R)

CD-R 1 contains Tables 1 to 6 and Tables O-X formatted in tab-delimited ASCII text. CD-R 1 is labeled with Volume Label 05-689. The file containing Table 1 is entitled 05-689 Table 1.txt, created on Jan. 9, 2007, and is 184 KB in size. The file containing Table 2 is entitled 05-689 Table 2.txt, created on Jan. 9, 2007, and is 185 KB in size. The file containing Table 3 is entitled 05-689 Table 3.txt, created on Jan. 9, 2007, and is 187 KB in size. The file containing Table 4 is entitled 05-689 Table 4.txt, created on Jan. 9, 2007, and is 186 KB in size. The file containing Table 5 is entitled 05-689 Table 5.txt, created on Jan. 9, 2007, and is 184 KB in size. The file containing Table 6 is entitled 05-689 Table 6.txt, created on Jan. 9, 2007, and is 187 KB in size. The file containing Table O is entitled 05-689 Table O.txt, created on Jan. 9, 2007, and is 1 KB in size. The file containing Table P is entitled 05-689 Table P.txt, created on Jan. 9, 2007, and is 6 KB in size. The file containing Table Q is entitled 05-689 Table Q.txt, created on Jan. 9, 2007, and is 1 KB in size. The file containing Table R is entitled 05-689 Table R.txt, created on Jan. 9, 2007, and is 6 KB in size. The file containing Table S is entitled 05-689 Table S.txt, created on Jan. 9, 2007, and is 1 KB in size. The file containing Table T is entitled 05-689 Table T.txt, created on Jan. 9, 2007, and is 6 KB in size. The file containing Table U is entitled 05-689 Table U.txt, created on Jan. 9, 2007, and is 1 KB in size. The file containing Table V is entitled 05-689 Table V.txt, created on Jan. 9, 2007, and is 6 KB in size. The file containing Table W is entitled 05-689 Table W.txt, created on Jan. 9, 2007, and is 3 KB in size. The file containing Table X is entitled 05-689 Table X.txt, created on Jan. 9, 2007, and is 1 KB in size.

The disclosure of Tables 1 to 6, and Tables O—X, submitted as an electronic document on compact disc as described above are to be part of the permanent USPTO record of this patent application and are hereby expressly incorporated by reference.

BACKGROUND OF THE INVENTION

1. Field of the Invention

The present invention is in the field of crystalline forms of polypeptides corresponding to the kinase domain of spleen tyrosine kinase (SYK), methods of obtaining such crystals, and to methods for identifying pharmacophores from high-resolution X-ray diffraction structures. The invention is also related to the field of using three-dimensional coordinates for screening for, identifying, and/or discovering compounds useful as inhibitors of SYK activity.

2. Summary of the Related Art

Spleen tyrosine kinase (SYK) is a member of the SYK family of tyrosine protein kinases, a family of cytoplasmic tyrosine kinases characterized by the presence of two SH2 domains in the amino terminal of a single kinase domain. Homologs of the SYK family of protein kinases have been identified in a number of species, including the human ZAP-70. SYK has been reported to be involved in several cellular signaling events. For example, SYK participates in immunoreceptor signaling, integrin signaling, and G protein-coupled receptor signaling. SYK is known to be expressed in hematopoietic cells as wells as in fibroblasts, epithelial cells, hepatocytes, neuronal cells, endothelial cells and mast cells. SYK is also involved in hematopoietic responses such as proliferation, for example, SYK inhibitors have been suggested as modulators of thrombin-induced ASM cell proliferation, differentiation, and phagocytosis.

In addition, SYK inhibitors have also been demonstrated to be important in non-hematopoietic cells as well, such as in fibroblasts, epithelial cells, breast tissue, hepatocytes, neuronal cells, and vascular endothelial cells. Accordingly, SYK has been implicated as playing a critical role in endothelial cell functions, including morphogenesis cell growth, migration, and survival, and as contributing to maintaining vascular integrity in vivo. For further review, see Yanagi et al., Biochem. Biophys. Res. Comm. 288:495-498 (2001).

Both SYK antisense and specific inhibitors have been shown to have some activity in asthma models and SYK is thought to be a target for the treatment of asthma and other airway diseases, as well as for allergies, inflammation, and autoimmunity. SYK has also been suggested as a target for the development of agonists in cancer therapy, due to its role in cell growth.

Knowledge of the 3-D structures of target proteins provides an important basis for structure-based approaches to drug design by defining the topographies of the complementary surfaces of ligands and their protein targets. Therefore, knowledge of the structure of the SYK protein may be useful in the identification, design, or development of novel and specific modulators of SYK, as well as diagnostic and pharmaceutical compounds useful for disorders associated with SYK expression or activity. Knowledge of the structure of SYK may also be useful for gene therapy. The three-dimensional structure of SYK may be useful, for example, for identifying novel therapeutic compounds that can modulate protein kinase activity, and for treatment of conditions mediated by human signal transduction of kinase activity, such as cancer, allergy, inflammation, asthma, arthritis, irritated bowel syndrome, and multiple sclerosis.

The molecular structure coordinates of SYK has been previously reported. For example, WO 04/035604 describes the crystal structure of SYK with stable ATP surrogates, such as AMP-PNP. Further, the coordinates of SYK co-crystals with Gleevec and Staurosporine have also been reported (Atwell et al., J. Biol. Chem. 279 (53):55827-55832 (2004); PDB ID: 1XBB and 1XBC). However, the currently available three-dimensional structures of SYK with or without bound ligands are not sufficient for identifying pharmacophores. The availability of pharmacophore models are desirable to facilitate the identification of modulators of SYK activity.

Thus, the present invention provides methods for identifying pharmacophore models using co-crystals of SYK and its ligands, and methods for identifying compounds that inhibit SYK using the pharmacophore models.

SUMMARY OF THE INVENTION

The present invention provides co-crystals of SYK and its ligands, methods of using the three-dimensional data from the co-crystals to identify and design pharmacophore models, methods for screening for or identifying compounds that modulate the activity of SYK using the pharmacophore models, and methods of inhibiting SYK with inhibitors identified using a pharmacophore model.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
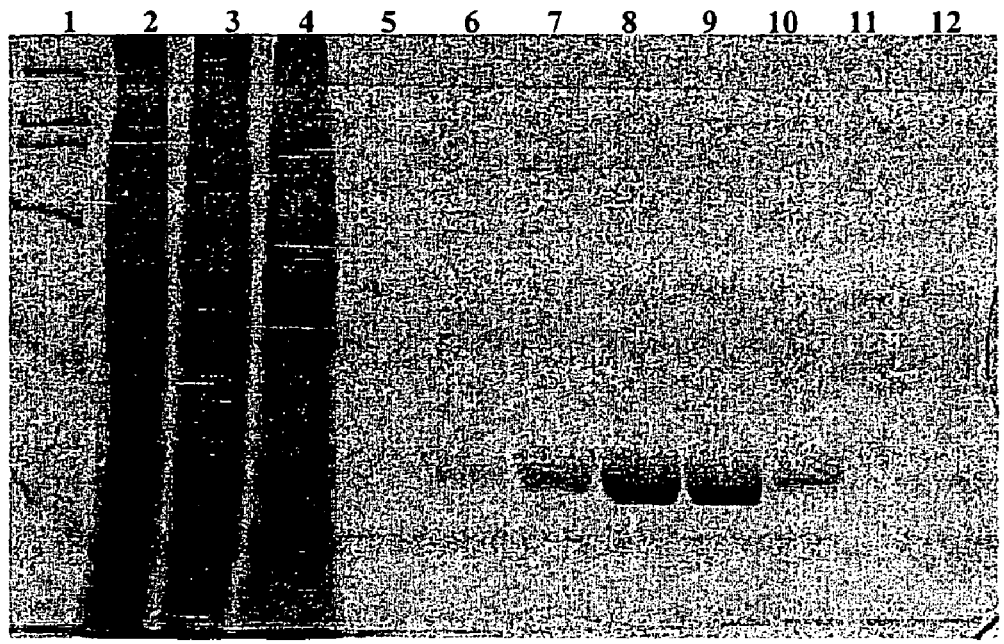
FIG. 1 is an SDS-PAGE of SYK Kinase 1358 to N635 with the mutation E440Q purified from a Ni-chelating column from SF9 cells.
Figure 2:
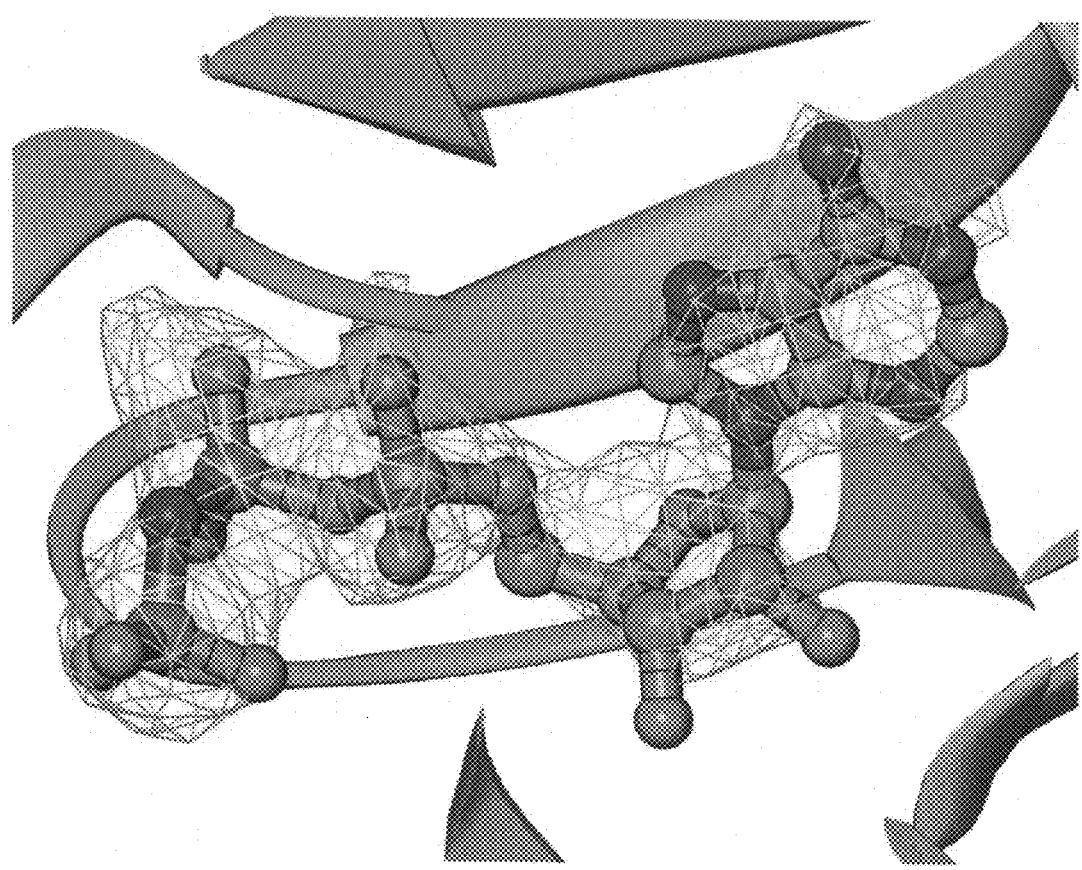
FIG. 2 illustrates the calculated Fo-Fc omit map of AMP-PNP Contoured at 2.5σ. Carbon atoms are represented in green; nitrogen atoms are represented in blue; phosphorous atoms are represented in purple; and oxygen atoms are represented in red. Ribbon diagrams representing alpha-helices and beta strands are light blue. Molecules and protein folds are represented using this color scheme throughout the figures.
Figure 3:
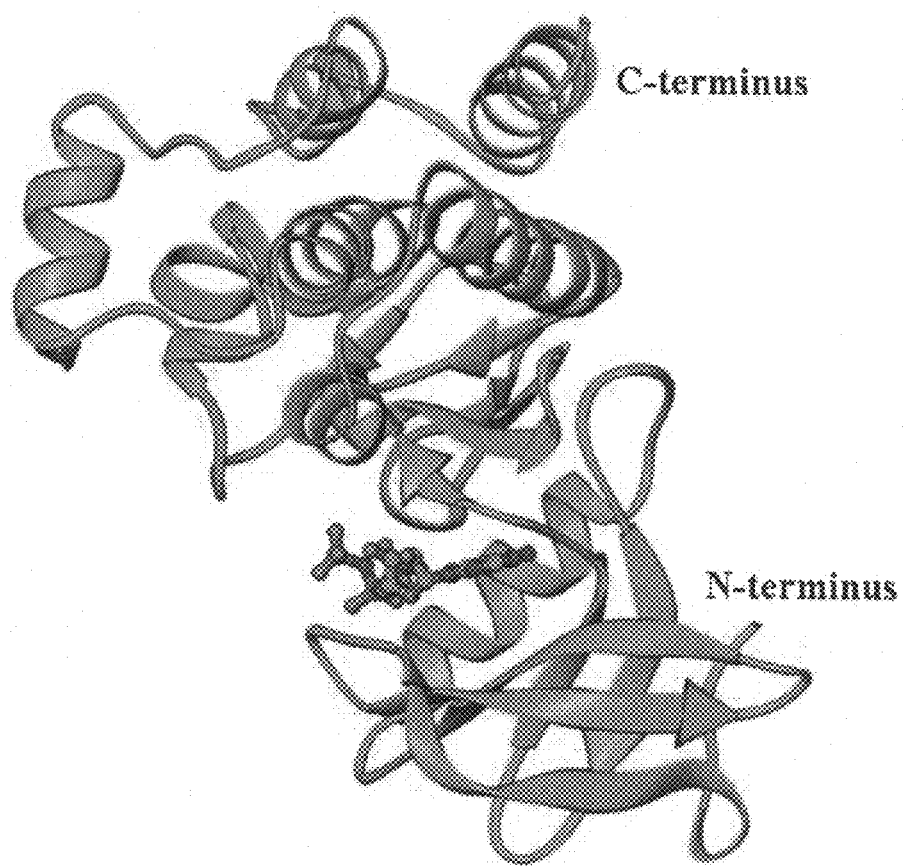
FIG. 3 illustrates the AMP-PNP in the ATP Binding Pocket of SYK kinase.
Figure 4:
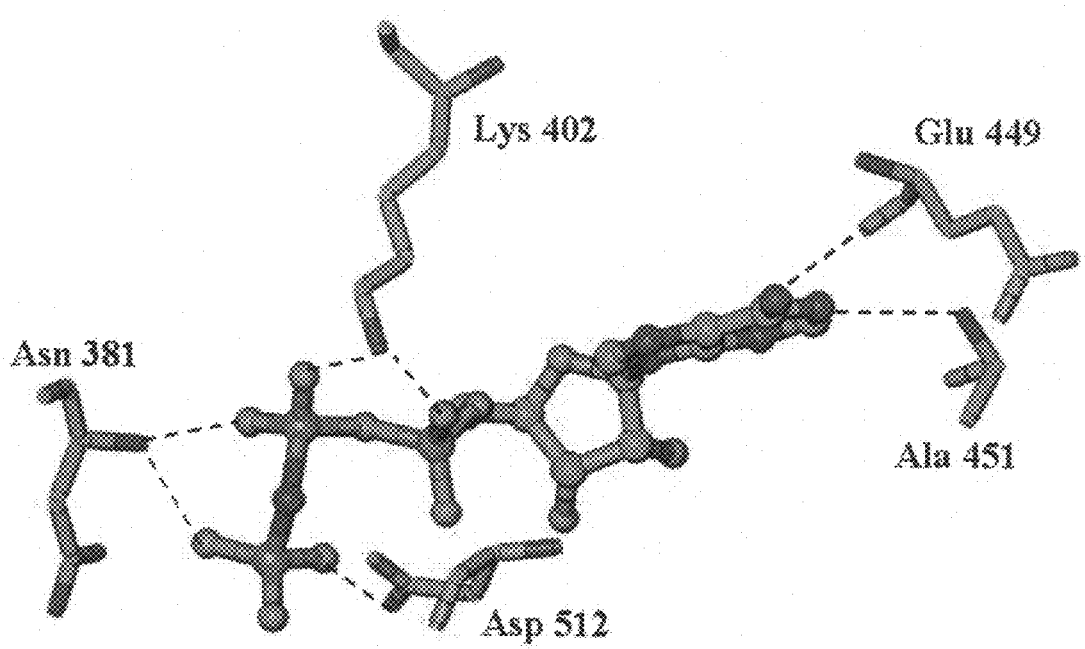
FIG. 4 illustrates the non-bonded interactions between AMP-PNP and SYK kinase.

The present invention provides co-crystals of SYK and its ligands, methods of using the three-dimensional data from the co-crystals to identify and design SYK inhibitors and SYK pharmacophores, methods for screening for or identifying compounds that modulate the activity of SYK, methods of inhibiting SYK with inhibitors identified using pharmacophores, and the pharmacophores identified by the methods of the invention.

As used herein, the terms "pharmacophore", "pharmacophore model" and "pharmacophore test model" are used interchangeably, and refer to a specific, three-dimensional map of chemical and biological structures, properties, and features common to a set of ligands that exhibit a particular activity. A pharmacophore is a compilation of the functional and structural features of ligands that accomplish a specific task (e.g., inhibition of SYK). A pharmacophore can be used as a model for the design of specific molecules that exhibit the same structural and functional features as the ligands from which the pharmacophore was derived. So, for example, a pharmacophore may have a structural feature and a functional feature. Examples of pharmacophores according to the invention are displayed in FIGS. 27-30. The term "inhibitor" is used in distinction to "pharmacophore" as referring to a particular molecule (i.e., a species of molecule described by the pharmacophore model).

"Pharmacophore features" or "features" refer to functional, structural, chemical or biological descriptors that describe a substituent and interaction of ligands with their receptors or binding sites. Such descriptors may be derived from any set of data, for example, but not limited to, three-dimensional data. Features may include any subatomic element, atom or groups of atoms that form, for example, but not limited to, hydrogen bond donors, hydrogen bond acceptors, hydrophobic regions, hydrophilic regions, ionizable regions, or aromatic rings. The features may further be described by the distances separating the features. For example, a feature may be a hydrogen bond donor that is 3 Å away from a hydrogen bond acceptor. Pharmacophore features may be arranged in three-dimensional space and define points of interaction with the residues lining a binding site. In addition, features may further be described by torsional degrees of freedom of an atom or groups of atoms that define distinct, low energy conformations.

In a first aspect (Aspect A), the invention comprises a method of constructing an SYK inhibitor pharmacophore comprising:

(a) generating a set of three-dimensional conformers comprising a binding site of SYK and compounds from a training set comprising one or more SYK ligands for the binding site;
(b) using the conformers generated in (a) to identify one or more features on the ligands, wherein the features comprise groups that interact with the residues lining the binding site; and (c) formulating a set of one or more pharmacophores from the conformers of (a), each of the pharmacophores comprising one or more features identified in (b).

In Aspect A1, the invention provides a method of constructing an SYK inhibitor pharmacophore according to Aspect A wherein the conformers are generated using the coordinates of the SYK binding site from one or more of Tables 1-6. The SYK ligand can be any ligand that can bind to the SYK binding site. In one embodiment, the conformers are generated using the coordinates of the SYK binding site and bound SYK ligand from one or more of Tables 1-6, wherein the SYK ligand is any one of compounds Cpd. No. 1-6.

In Aspect A2, the invention comprises a method of constructing an SYK inhibitor pharmacophore comprising:

(a) generating a set of three-dimensional conformers of one or more compounds that are SYK ligands;
(b) using the conformers generated in (a) to identify one or more features on the ligands, wherein the features comprise groups that interact with the residues lining an SYK binding site; and (c) formulating a set of one or more pharmacophores from the conformers of (a), each of the pharmacophores comprising one or more features identified in (b).

In Aspect A-A2, the three-dimensional conformers can be generated by using coordinates from co-crystals of SYK or fragment thereof containing a ligand binding site and SYK ligands, such as those disclosed herein, using methods known to those skilled in the art. In one embodiment, the SYK comprises the fragment from I358 to N635 of the wild type SYK (Atwell et al., J. Biol. Chem. 279 (53):55827-55832 (2004); PDB ID:1XBA) optionally with the mutation E440Q.

The features can be selected from the group consisting of a hydrogen bond donor; a hydrogen bond acceptor, a hydrophobic region, a hydrophilic region, an ionizable region, and an aromatic ring, wherein the features are arranged in three-dimensional space and interact with the residues lining the binding site. In one embodiment, the step of formulating a set of one or more pharmacophores comprises measuring the distances separating the features, measuring the angles separating the features, or measuring the distances and angles separating the features. Methods of identifying features are known to those skilled in the art (Lemmen C. and Lengauer T., Computational methods for the structural alignment of molecules, J. Comput. Aided Mol. Des. 14(3):215-32 (2000); Guner O., Clement O. and Kurogi Y., Pharmacophore modeling and three dimensional database searching for drug design using catalyst: recent advances, Curr. Med. Chem. 11(22):2991-3005 (2004)).

In Aspect A-A2, the steps can be conducted using techniques known to those skilled in the art (see below). The training set of SYK ligands generally comprises compound(s) that are known to exhibit SYK inhibition, such as those disclosed herein. Preferably the compounds that exhibit SYK inhibition will have $IC_{50}$ values of 500 nM or less measured by an SYK kinase assay, such as described in Yamamoto N., Takeshita K., Shichijo M., Kokubo T., Sato M., Nakashima K., Ishimori M., Nagai H., Li Y. F., Yura T., Bacon K. B. The orally available spleen tyrosine kinase inhibitor 2-[7-(3,4-dimethoxyphenyl)-imidazo[1,2-c]pyrimidin-5-ylamino]nicotinamide dihydrochloride (BAY 61-3606) blocks antigen-induced airway inflammation in rodents, J. Pharmacol. Exp. Ther. 306(3):1174-81 (2003). Preferably, the training set of step (a) comprises at least three compounds. Also preferred is training set of step (a) that comprises at least six compounds. In one embodiment, the training set of step (a) comprises one or more compounds having the structure:

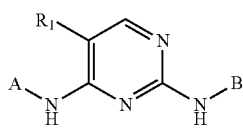

I wherein, A and B are independently aryl or heteroaryl wherein each of the aryl and heteroaryl is optionally substituted with one or more groups selected from —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, mono- to perhalogenated C$_1$-C$_6$ alkyl, mono- to perhalogenated C$_1$-C$_6$ alkyloxy, —S(O)$_2$—NH$_2$, —S(O)$_2$—N(H)—C$_1$-C$_6$ alkyl, —S(O)$_2$—N(C$_1$-C$_6$ alkyl)(C$_1$-C$_6$ alkyl), C$_1$-C$_6$ alkyl, oxo, halo, and C$_1$-C$_6$ alkyloxy; and R$_1$ is halo, —OH, —NH$_2$, N(H)—C$_1$-C$_6$ alkyl, —N(C$_1$-C$_6$ alkyl)(C$_1$-C$_6$ alkyl), —SH, —S—C$_1$-C$_6$ alkyl, —CN, C$_1$-C$_6$ alkyl, C$_1$-C$_6$ alkyloxy, mono- to perhalogenated C$_1$-C$_6$ alkyl, and mono- to perhalogenated C$_1$-C$_6$ alkyloxy. Preferably, the training set of step (a) comprises one or more compounds selected from the group consisting of:

Cpd. No. 1

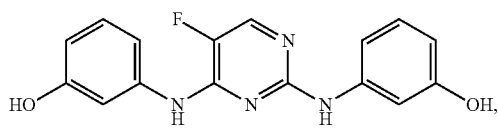

Cpd. No. 2

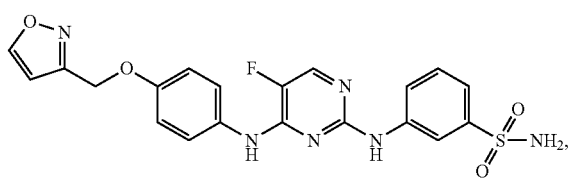

Cpd. No. 3

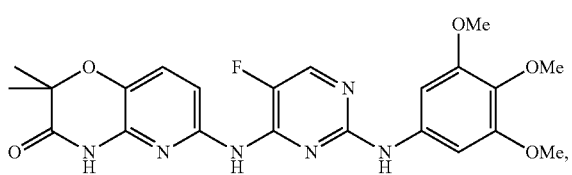

Cpd. No. 4

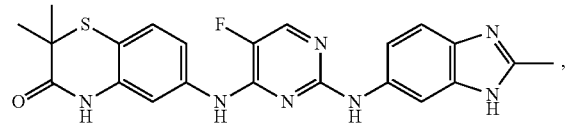

Cpd. No. 5

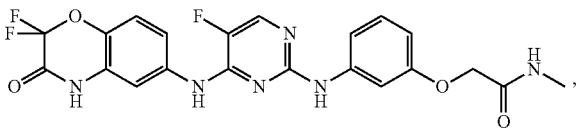

and

Cpd. No. 6

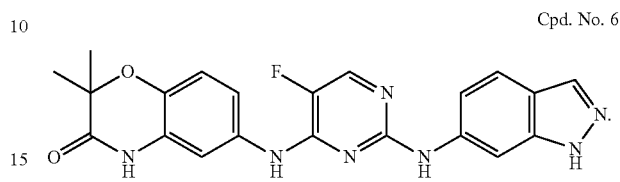

Figure 19:
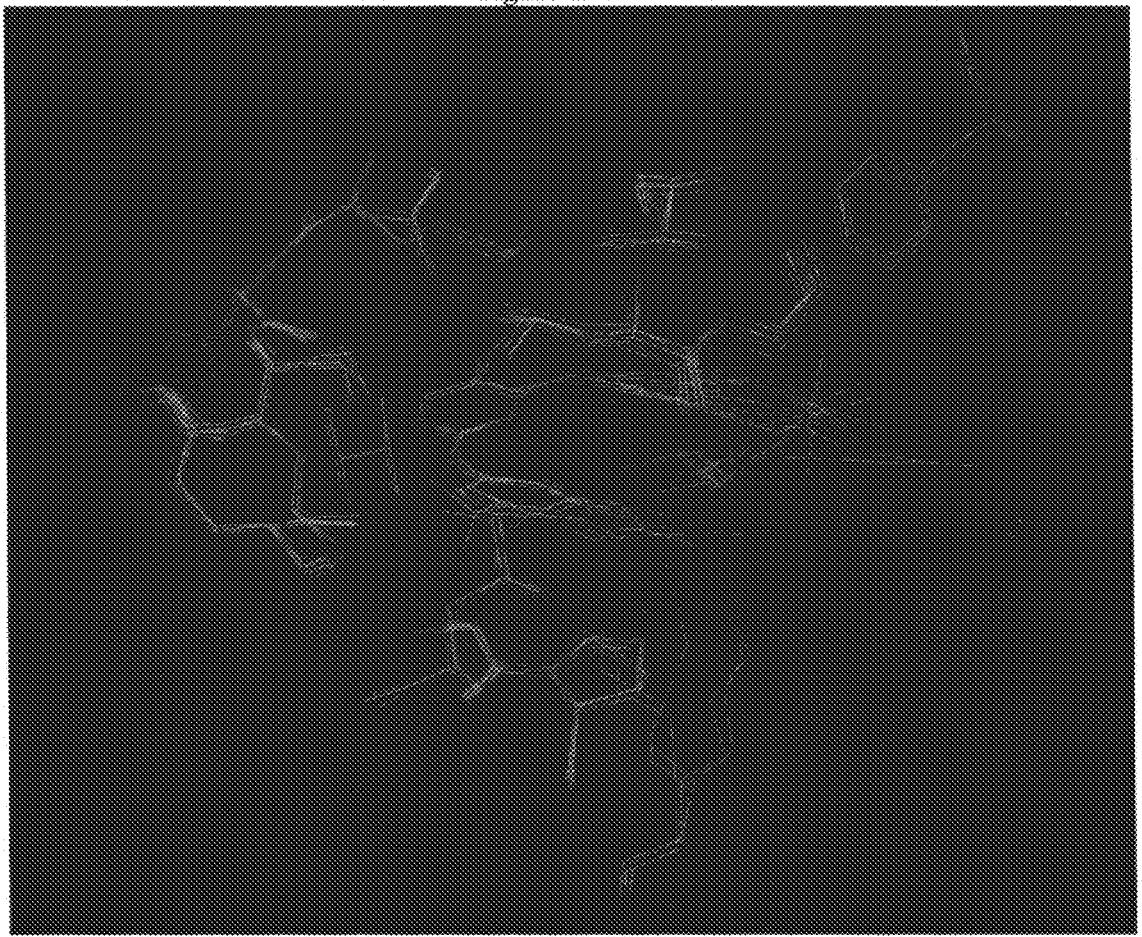
FIG. 19 illustrates the overlay of SYK structures with Cpd. No. 1-6 with residues within 4.5 Å away from the ligand. Waters are represented as red dots. Most of the residues overlay well, except Lys458 at the front which has quite some dynamic motion.
Figure 20:
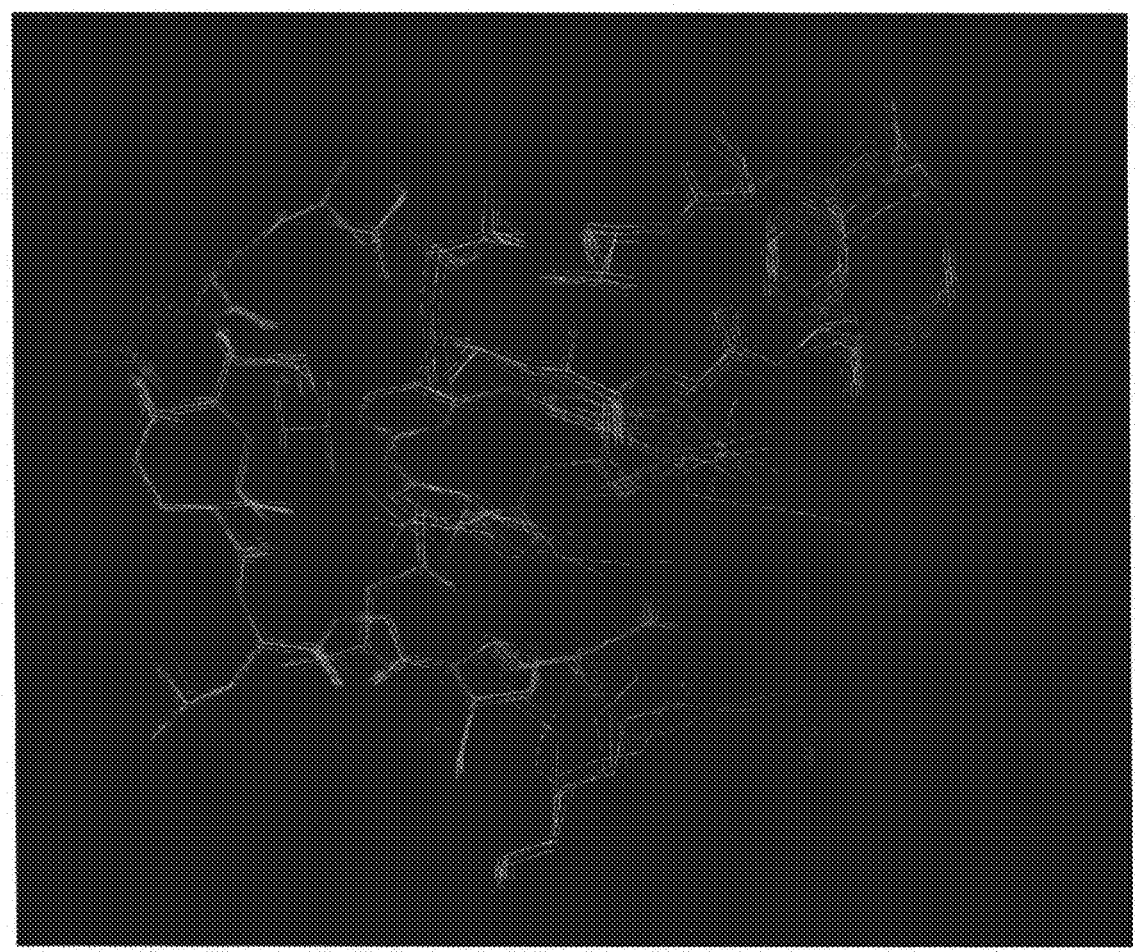
FIG. 20 illustrates the overlay of SYK structures with Cpd. No. 1-6 with residues within 6 Å away from the ligand.
Figure 21:
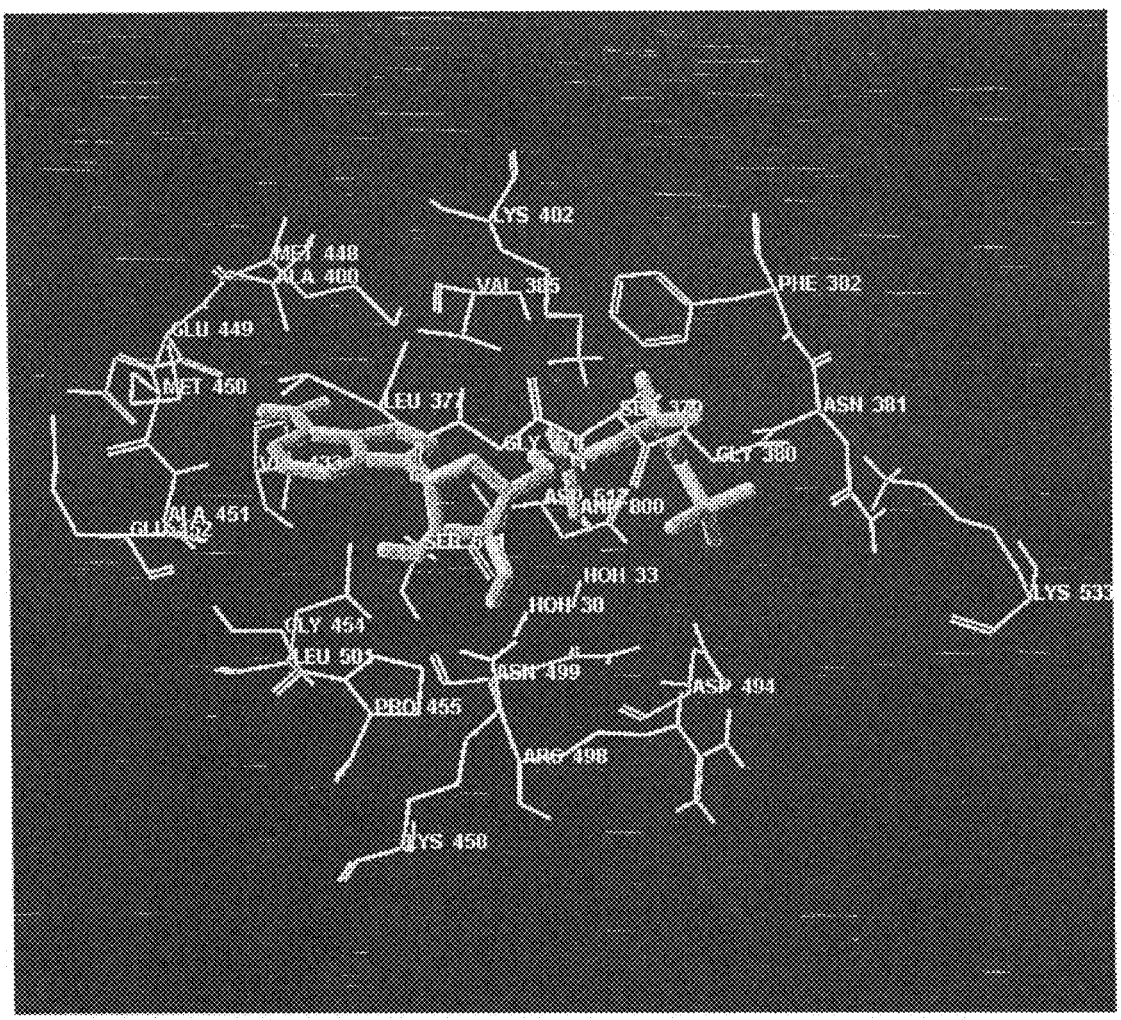
FIG. 21 illustrates the co-crystals of SYK with AMP-PNP.
Figure 22:
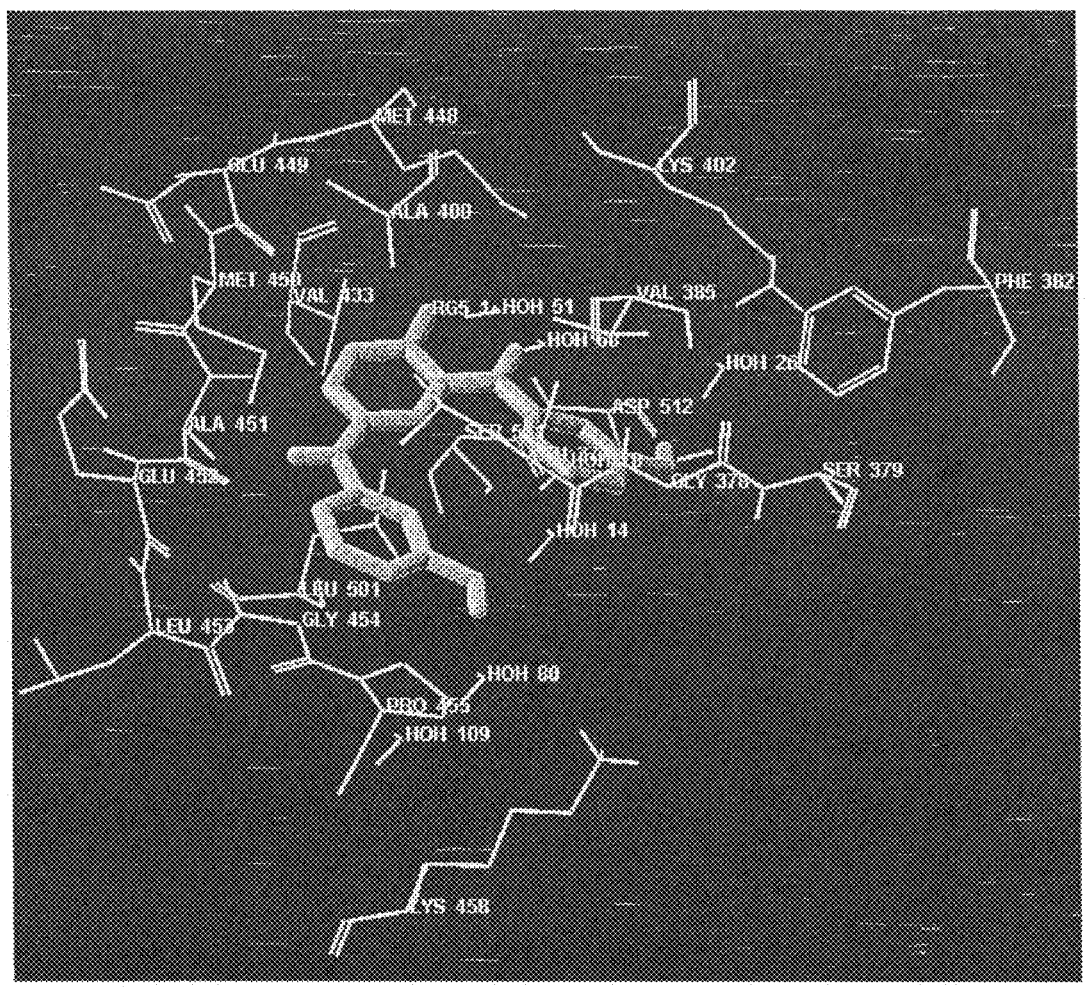
FIG. 22 illustrates the co-crystals of SYK with Cpd. No. 1.

In one embodiment of Aspect A, the conformer comprises one or any combination of two or more of the following:

(a) the following residues within 4.5 Å of the SYK ligand: Leu377, Gly378, Phe382, Val385, Ala400, Val433, Met448, Glu449, Met450, Ala451, Glu452, Gly454, Pro455, Lys458, Leu501, and Asp512 (FIG. 19);

(b) the following residues within 6 Å of the SYK ligand in addition to the residues listed in (a): Lys375, Ser379, Gly380, Gly383, Thr384, Lys402, Leu453, Arg498, Asn499, and Ser511 (FIG. 20);

(c) a hydrophobic core comprising Met448, Ala400, Val433, Met448, Glu449, Met450, Ala451, and Leu501, wherein Met448 interacts with a hydrophobic region or an aromatic ring of the ligand;

(d) the backbone carbonyl group of Glu449 and Ala451 that act as hydrogen bond acceptors from the ligand;

(e) the backbone amine group of Ala451 that acts as a hydrogen bond donor to the ligand;

(f) the carboxyl group of Asp512 that acts as a hydrogen bond acceptor from the ligand;

(g) and the amine of Lys458 that acts as one or more hydrogen bond donors to the ligand;

(h) a hydrophobic core comprising Leu377, Gly378, Phe382, and Val385;

(i) a hydrophobic core comprising Leu377, Met450, Ala451, Glu452, Gly454, Pro455, and Leu501;

(j) a binding site in the conformer that is surrounded by Val433, Met448, Asp512 and a ligand, wherein the binding site comprises one or more water molecules; or (k) and a hydrophilic region formed by Arg498 and Asn499, wherein the hydrophilic region may contribute to ligand selectivity.

Figure 27:
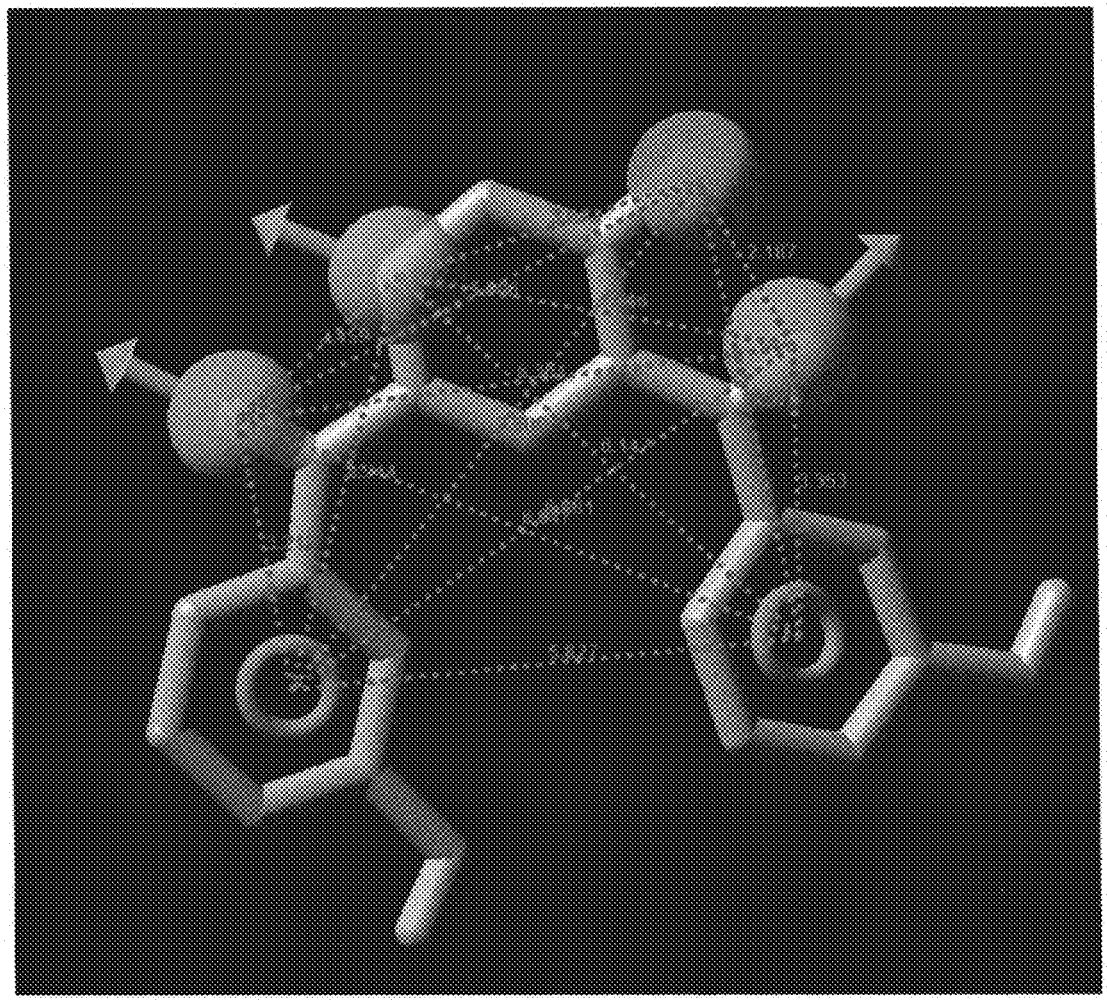
FIG. 27 illustrates a pharmacophore with features based on the structure alignment of the bound structures of the Cpd. No. 1. The pharmacophore model was derived by Phase (Schrodinger Inc.). The model comprises six features. The features are ADDHRR(R: aromatic, orange circle: D: hydrogen-bond donor, blue ball with arrow; H: hydrophobic, green ball; A: hydrogen-bond acceptor, pink ball with arrow). The model shows alignment of Cpd. No. 1 with inter-distances of the pharmacophore features. The three-dimensional coordinates of the pharmacophore feature points are listed in Table 0 in the file entitled 05-689 Table O.txt in CD-R 1. The three-dimensional coordinates can be used to calculate the distances and angles between any pharmacophore feature points. The vector direction of the hydrogen donor, acceptor and the aromatic ring can be calculated from the coordinates of the reference compound in conjunction with the pharmacophore feature points. The reference compound's coordinates is included in Table P in the file entitled 05-689 Table P.txt in CD-R 1.
Figure 28:
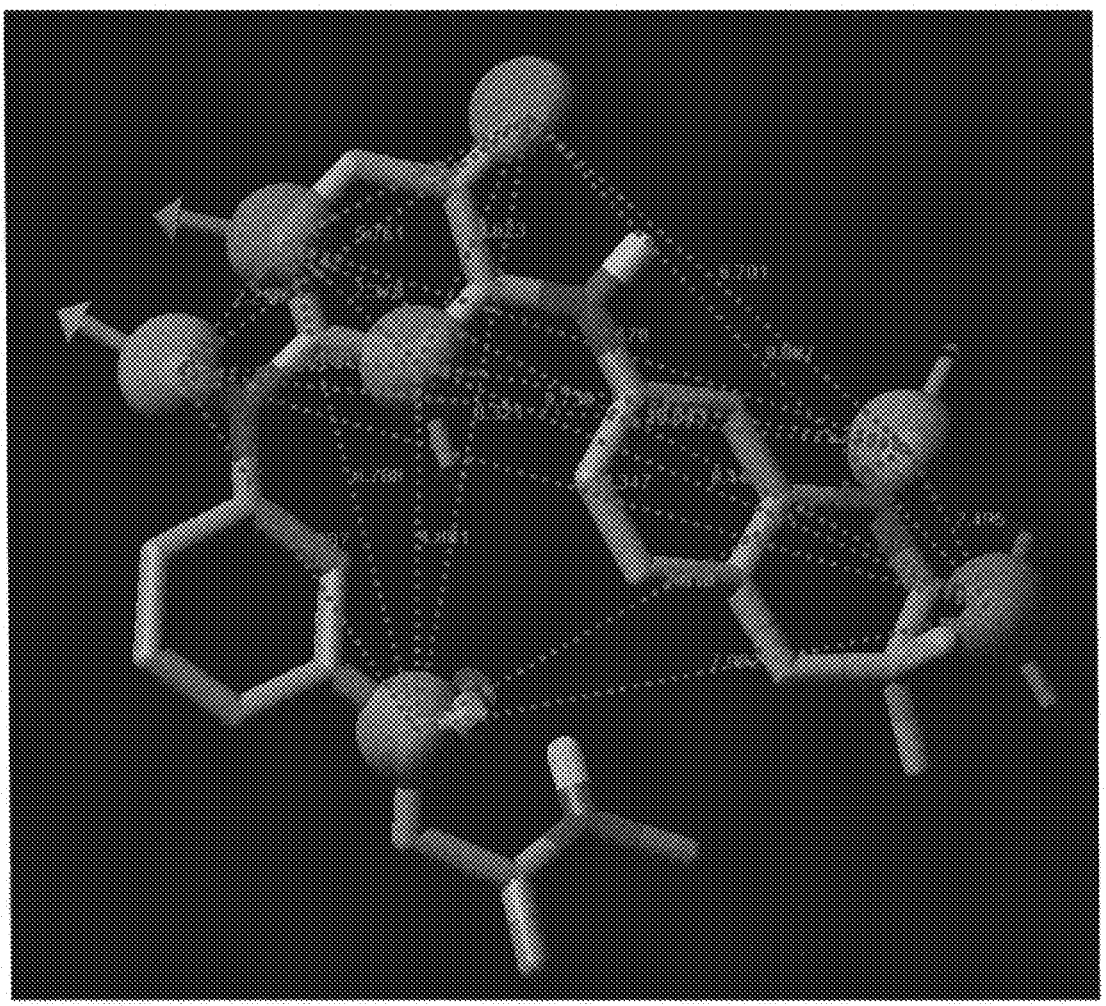
FIG. 28 illustrates a pharmacophore model comprising seven features AAAADDH. The model shows alignment of Cpd. No. 5 with pharmacophore features and inter-distances. The features are D: hydrogen-bond donor, blue ball with arrow; H: hydrophobic, green ball; A: hydrogen-bond acceptor, red ball with arrow. The three-dimensional coordinates of the pharmacophore feature points are listed in Table Q in the file entitled 05-689 Table Q.txt in CD-R 1. The three-dimensional coordinates can be used to calculate the distances and angles between any pharmacophore feature points. The vector direction of the hydrogen donor, acceptor and the aromatic ring can be calculated from the coordinates of the reference compound in conjunction with the pharmacophore feature points. The reference compound's coordinates is included in Table R in the file entitled 05-689 Table R.txt in CD-R 1.
Figure 29:
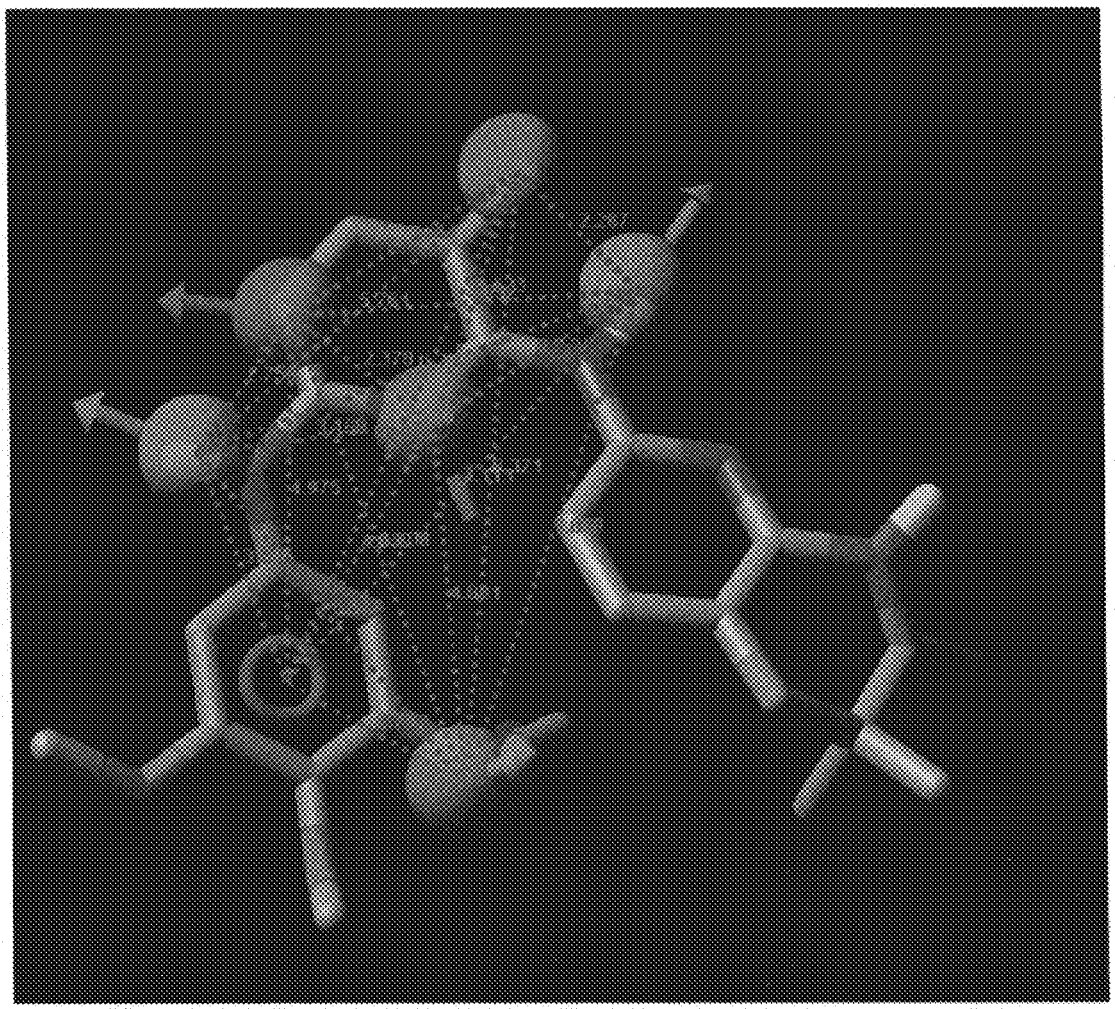
FIG. 29 illustrates a pharmacophore model comprising seven features AAADDHR. The model shows alignment of Cpd. No. 3 with pharmacophore features and inter-distances. The features are R: aromatic, orange circle; D: hydrogen-bond donor, blue ball with arrow; H: hydrophobic, green ball; A: hydrogen-bond acceptor, red ball with arrow. The three-dimensional coordinates of the pharmacophore feature points are listed in Table S in the file entitled 05-689 Table S.txt in CD-R 1. The three-dimensional coordinates can be used to calculate the distances and angles between any pharmacophore feature points. The vector direction of the hydrogen donor, acceptor and the aromatic ring can be calculated from the coordinates of the reference compound in conjunction with the pharmacophore feature points. The reference compound's coordinates is included in Table T in the file entitled 05-689 Table T.txt in CD-R 1.
Figure 30:
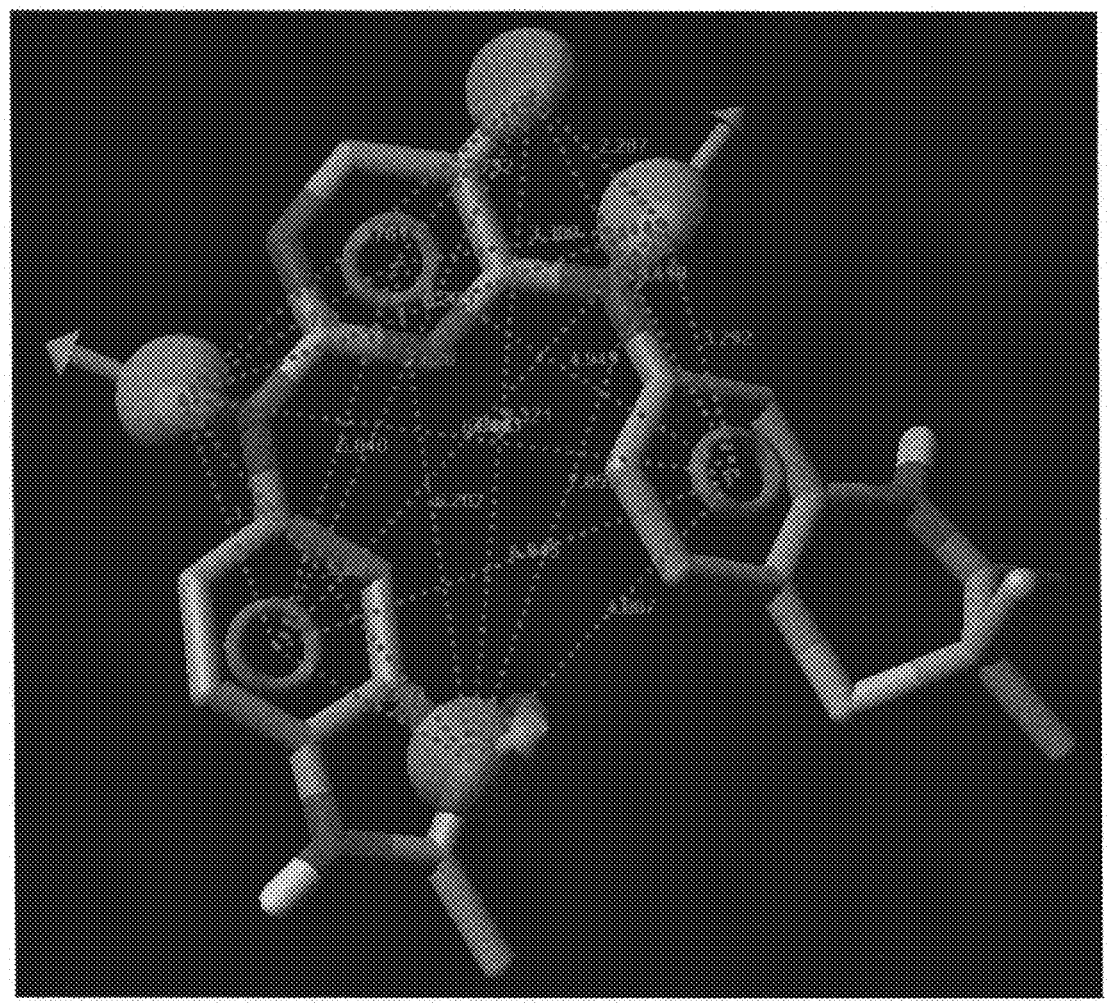
FIG. 30 illustrates a pharmacophore model comprising seven features ADDHRRR. The model shows alignment of Cpd. No. 4 with pharmacophore features and inter-distances. The features are A: aromatic, orange circle; D: hydrogen-bond donor, blue ball with arrow; H: hydrophobic, green ball; R: hydrogen-bond acceptor, red ball with arrow. The three-dimensional coordinates of the pharmacophore feature points are listed in Table U in the file entitled 05-689 Table U.txt in CD-R 1. The three-dimensional coordinates can be used to calculate the distances and angles between any pharmacophore feature points. The vector direction of the hydrogen donor, acceptor and the aromatic ring can be calculated from the coordinates of the reference compound in conjunction with the pharmacophore feature points. The reference compound's coordinates is included in Table V in the file entitled 05-689 Table V.txt in CD-R 1.
Figure 31:
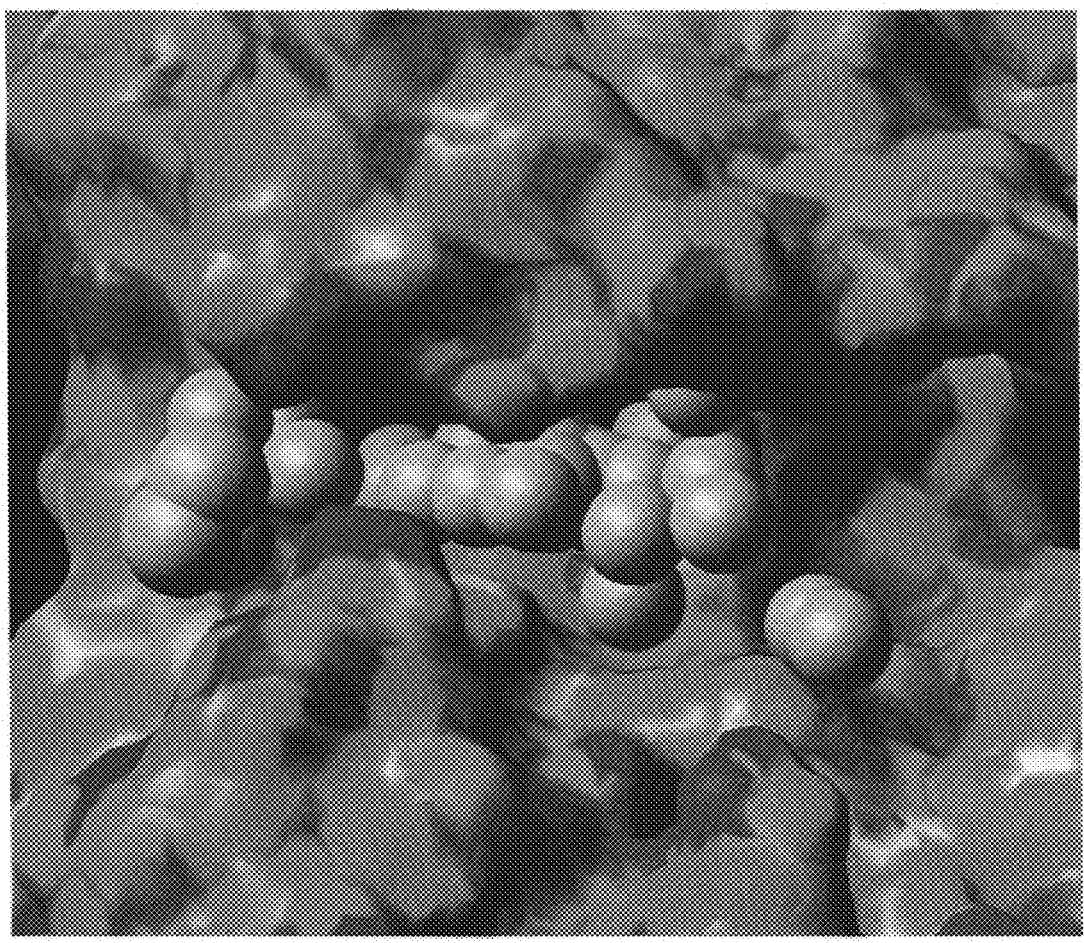
FIG. 31 illustrates the sphere space based on the normal projection of the protein surface of the ATP binding pocket. There are 38 spheres and any combination of those can be used as the pharmacophore model definition. The coordinates of the spheres are listed in Table W in the file entitled 05-689 Table W.txt in CD-R 1.
Figure 32:
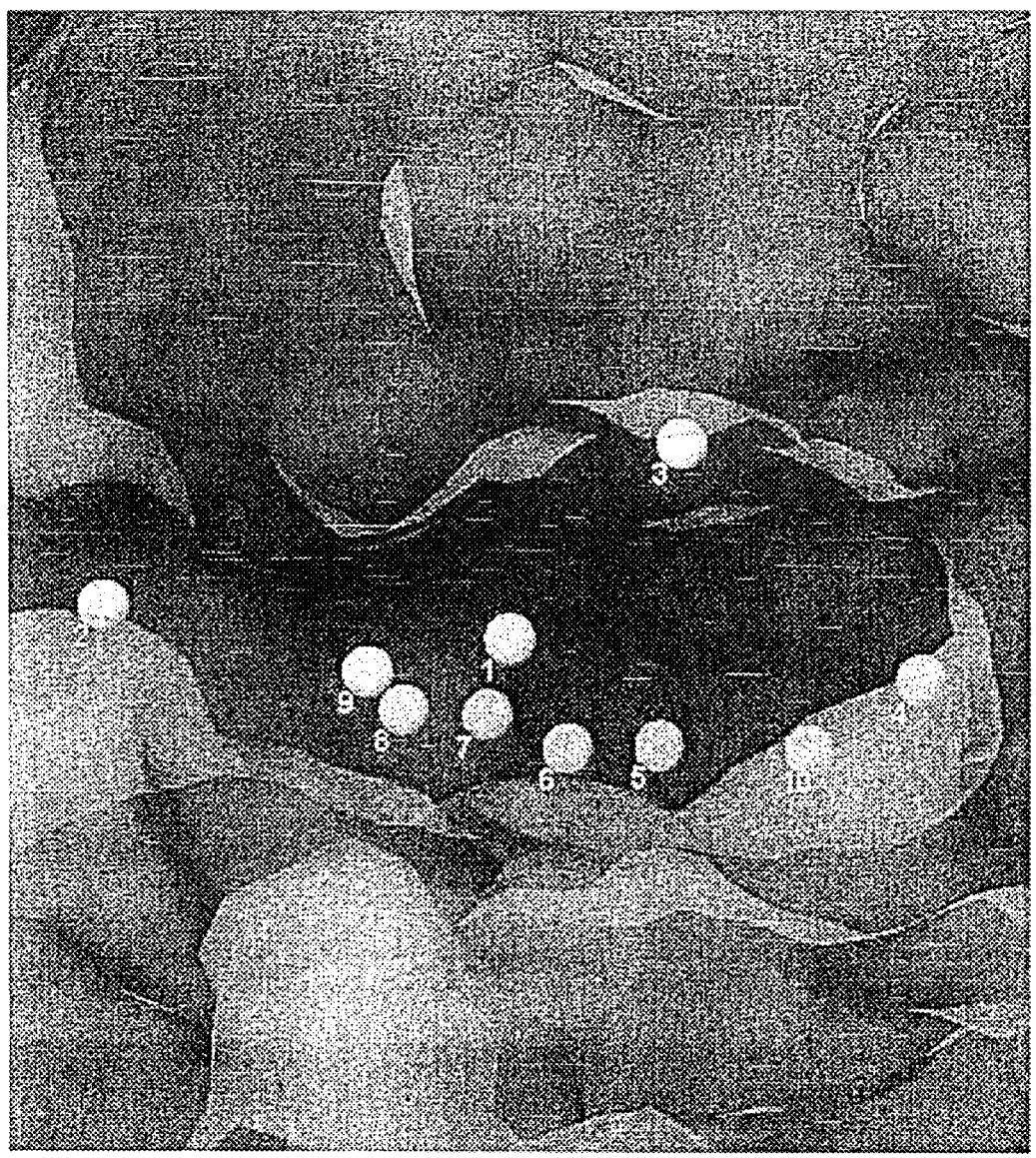
FIG. 32 illustrates a 10-feature pharmacophore model. The coordinates of the spheres are listed in Table X in the file entitled 05-689 Table X.txt in CD-R 1. Hydrophobic features: sphere 5, 1, 9, 3; H-bond acceptor features: 6, 8, 2; H-bond donor features: 7; polar features: 4, 10; aromatic features: 1, 9.

In Aspect B, the invention comprises a pharmacophore formulated according to Aspect A. Preferably, the pharmacophore comprises at least three features selected from the group consisting of a hydrogen bond donor, a hydrogen bond acceptor, a hydrophobic region, a hydrophilic region, an ionizable region and an aromatic ring. In one embodiment, the pharmacophore comprises six features: two aromatic ring features, two hydrogen bond donor features, one hydrogen bond acceptor feature, and one hydrophobic region feature, as illustrated in FIG. 27. In another embodiment, the pharmacophore comprises seven features: two hydrogen bond donor features, four hydrogen bond acceptor features, and one hydrophobic region feature, as illustrated in FIG. 28. In still another embodiment, the pharmacophore comprises seven features: one aromatic ring feature, two hydrogen bond donor features, three hydrogen bond acceptor features, and one hydrophobic region feature, as illustrated in FIG. 29. In yet another embodiment, the pharmacophore comprises seven features: three aromatic ring features, two hydrogen bond donor features, one hydrogen bond acceptor feature, and one hydrophobic region feature, as illustrated in FIG. 30.

In Aspect C, the invention comprises a method for screening for SYK inhibitors comprising:
(a) generating a set of three-dimensional conformers comprising a binding site of SYK and compounds from a training set comprising at least one SYK ligand for the binding site;
(b) formulating a set of one or more pharmacophores from the conformers of (a), the pharmacophores comprising one or more features;
(c) providing a set of one or more compounds that are possible SYK inhibitors;
(d) comparing the compound(s) with the pharmacophore(s) and maximizing the fit of the compound(s) to the pharmacophore(s); and
(e) identifying one or more compounds that fit the constraints imposed by the pharmacophore(s), each of the constraints of the pharmacophore(s) being defined by at least one pharmacophore feature.

In Aspect C, maximizing the fit in step (d) is preferably conducted using molecular modeling software PHASE from Schrodinger Inc. (New York, USA). By comparing the compound with the pharmacophore and maximizing the fit of the compound to the pharmacophore is meant comparing the one or more features on the compound with the one or more features at similar locations on the pharmacophore. This may require rotation and translation of the compound to achieve the best alignment with the pharmacophore in order to effectively compare the features. A compound is said to fit into a pharmacophore if the features on the compound match with the features on the pharmacophore. For example, a compound with an phenyl ring in a location fits into a pharmacophore if the phenyl ring matches with an aromatic ring in the same location in the pharmacophore. In such a case, the compound is said to fit the constraints of the pharmacophore. A compound fitting an SYK pharmacophore model would be identified as an SYK inhibitor. One skilled in the art know that various methods can be used to evaluate fitting a compound into a pharmacophore in addition to matching the features. For example, comparing the compound with a pharmacophore and maximizing the fit can be evaluated by rmsd or by other structural measurements. For example, the software module PHASE from Schrodinger (New York, USA) can be used for comparing a compound with a pharmacophore. Phase is a chemical software package offering a comprehensive set of tools for ligand-based drug design. Graphical workflows are provided to support a range of tasks, including 3D conformational analysis, pharmacophore perception and elucidation, QSAR model development, and 3D database preparation and screening. The final fit score of the compound to the pharmacophore model is a regression model of individual match score based on vector, site, volume and selectivity. In one embodiment, the inhibitors comprise compounds having the structure:

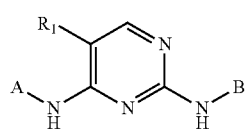

wherein
A and B are independently aryl or heteroaryl wherein each of the aryl and heteroaryl is optionally substituted with one or more groups selected from —OH, —N(H)—$C_1$-$C_6$ alkyl, —N($C_1$-$C_6$ alkyl)($C_1$-$C_6$ alkyl), —SH, —S—$C_1$-$C_6$ alkyl, —CN, mono- to perhalogenated $C_1$-$C_6$ alkyl, mono- to perhalogenated $C_1$-$C_6$ alkyloxy, —S(O)$_2$—NH$_2$, —S(O)$_2$—N (H)—$C_1$-$C_6$ alkyl, —S(O)$_2$—N($C_1$-$C_6$ alkyl)$_2$, $C_1$-$C_6$ alkyl, oxo, halo, and $C_1$-$C_6$ alkyloxy; and $R_1$ is halo, —OH, —NH$_2$, —N(H)—$C_1$-$C_6$ alkyl, —N($C_1$-$C_6$ alkyl)($C_1$-$C_6$ alkyl), —SH, —S—$C_1$-$C_6$ alkyl, —CN, $C_1$-$C_6$ alkyl, $C_1$-$C_6$ alkyloxy, mono- to perhalogenated $C_1$-$C_6$ alkyl, and mono- to perhalogenated $C_1$-$C_6$ alkyloxy.

In Aspect C1, the invention provides a method for screening for SYK inhibitors according to Aspect C wherein the conformers are generated using the coordinates of the SYK binding site from one or more of Tables 1-6. The SYK ligand can be any ligand that can bind to the SYK binding site. In one embodiment, the conformers are generated using the coordinates of the SYK binding site and bound SYK ligand from one or more of Tables 1-6, wherein the SYK ligand is any one of compounds Cpd. No. 1-6. In one embodiment, coordinates of the compounds that are possible SYK inhibitors are generated using, for example, a computer program, and then, using molecular modeling software, the coordinates of the compounds are fitted into the binding site of SYK, wherein the coordinates of the binding site are derived from one or more of Tables 1-6.

In Aspect C2, the invention comprises compounds identified by the method of Aspect C.

In Aspect D, the invention comprises a method of discovering SYK inhibitors using at least one pharmacophore comprising:
(a) providing a first virtual library of at least one scaffold molecular group, each scaffold comprising at least one attachment point for a substituent and comprising a plurality of atoms defined by a set of three-dimensional coordinates;
(b) providing a second virtual library of a plurality of substituents, each of the plurality of substituents being described by a set of conformations, wherein each conformation is a rotamer;
(c) assigning features to all possible groups of at least one atom on the rotamers and on the scaffold, wherein the features correspond to the features of at least one pharmacophore;
(d) generating a set of potential SYK inhibitors by adding the rotamers from the second virtual library to each attachment point of each scaffold; and
(e) evaluating the compatibility of each potential SYK inhibitor with at least one pharmacophore comprising comparing the features assigned in (c) for the rotamer and the scaffold with the features of the pharmacophore and selecting one or more compounds fitting the constraints of one or more pharmacophores.

In one embodiment of Aspect D, the scaffold comprises compounds having the structure:

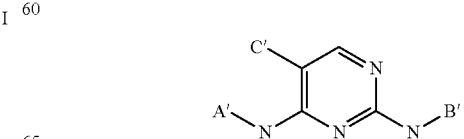

wherein A', B' and C' are attachment points for the substituents. The substituents attached at points A' and B' are independently aryl or heteroaryl, wherein each of the aryl and heteroaryl is optionally substituted with one or more groups selected from —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, mono- to perhalogenated C$_1$-C$_6$ alkyl, mono- to perhalogenated C$_1$-C$_6$ alkyloxy, —S(O)$_2$—NH$_2$, —S(O)$_2$—N(H)—C$_1$-C$_6$ alkyl, —S(O)$_2$—N(C$_1$-C$_6$ alkyl)$_2$, C$_1$-C$_6$ alkyl, oxo, halo, and C$_1$-C$_6$ alkyloxy. The substituents attached at point C' is halo, —OH, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, C$_1$-C$_6$ alkyl, C$_1$-C$_6$ alkyloxy, mono- to perhalogenated C$_1$-C$_6$ alkyl, and mono- to perhalogenated C$_1$-C$_6$ alkyloxy. The steps of Aspect D are preferably performed by a data processor. The features of the rotamers, scaffold and pharmacophore are defined as hydrogen bond donors; hydrogen bond acceptors, hydrophobic regions, hydrophilic regions, ionizable regions and aromatic rings. The features can also be further described by the distances separating each of the features.

One skilled in the art would recognize that additional scaffolds can be generated by screening a pharmacophore model against one or more candidate compounds in order to identify compounds that have structural moieties that overlap with the pharmacophore model. Thus, depending on the characteristics of the pharmacophore model used, many types of scaffolds can be used to generate SYK inhibitors.

Evaluating the compatibility of potential SYK inhibitors with pharmacophores comprises comparing the features assigned for the rotamers and the scaffolds used to form the potential SYK inhibitor compounds with the features of the pharmacophores. Compounds that fit the constraints of the pharmacophores are selected as SYK inhibitors. Comparing the features of the compounds with the pharmacophore and fitting compounds to the constraints can be accomplished as described for Aspect C of the invention.

Selecting SYK inhibitor compounds that fit into pharmacophores by comparing potential SYK inhibitor compounds with pharmacophores may comprise eliminating specific rotamers and scaffolds that form compounds that do not fit into the pharmacophores. This ensures that only rotamers and scaffold with the correct orientation are used to form potential SYK inhibitor compounds, which in turn increasing the probability that potential SYK inhibitor compounds would fit into pharmacophores.

In Aspect D1, the invention provides a method of discovering SYK inhibitors using a pharmacophores according to Aspect D, wherein the pharmacophores are generated using the coordinates of the SYK binding site from one or more of Tables 1-6. In one embodiment, the pharmacophores are generated using the coordinates of the SYK binding site and bound SYK ligand from one or more of Tables 1-6, wherein the SYK ligand is any one of compounds Cpd. No. 1-6. In one embodiment, coordinates of the compounds formed with the scaffolds and rotamers are generated using, for example, a computer program, and then, using molecular modeling software, the coordinates of the compounds are fitted into the binding site of SYK, wherein the coordinates of the binding site are derived from one or more of Tables 1-6.

In Aspect D2, the invention comprises compounds identified by the method of Aspect D.

In Aspect E, the invention comprises a method for inhibiting SYK comprising causing a compound according to Aspect B, C, or D to contact SYK.

In one embodiment of Aspect E, the inhibitors comprise compounds having the structure:

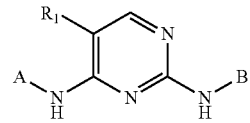

wherein
A and B are independently aryl or heteroaryl, wherein each of the aryl and heteroaryl is optionally substituted with one or more groups selected from —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, mono- to perhalogenated C$_1$-C$_6$ alkyl, mono- to perhalogenated C$_1$-C$_6$ alkyloxy, —S(O)$_2$—NH$_2$, —S(O)$_2$—N(H)—C$_1$-C$_6$ alkyl; —S(O)$_2$—N(C$_1$-C$_6$ alkyl)$_2$, C$_1$-C$_6$ alkyl, oxo, halo, and C$_1$-C$_6$ alkyloxy; and R$_1$ is halo, —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, C$_1$-C$_6$ alkyl, C$_1$-C$_6$ alkyloxy, mono- to perhalogenated C$_1$-C$_6$ alkyl, and mono- to perhalogenated C$_1$-C$_6$ alkyloxy.

In Aspect E, the features are selected from the group consisting of a hydrogen bond donor, a hydrogen bond acceptor, a hydrophobic region, an ionizable region and an aromatic ring, wherein the features are arranged in three-dimensional space and interact with the residues lining the binding site.

Generating a conformer of a binding site of SYK and a SYK ligand comprises adding together in a solvent the SYK binding site and the ligand. The solvent is then allowed to evaporate so that crystals are formed. The solvent can be any suitable solvent, such as a buffer comprising salts, protectants such as, but not limited to, glycerol, reducing or non-reducing agents, crystallant such as, but not limited to, PEG, citrate, and DMSO. The crystals are then collected and subjected to X-ray diffraction analysis from which a three-dimensional structure can be calculated. The calculated three-dimensional structure is used to derive coordinates for each atom in the crystal so that the coordinates for each atom of SYK and the ligand can be determined. To generate a set of conformers, the process described above is repeated with one or more additional ligands.

Conformers can also be generated in silico by using coordinates of the SYK with one or more binding sites. The binding sites may or may not be bound to ligands. Coordinates of SYK are publicly available (Protein Data Bank ID No. 1XBA) and one skilled in the art would know how to use coordinates of the SYK binding sites to generate conformers comprising one or more SYK binding sites bound to ligands. One way to do this is to generate coordinates of ligands in silico by modeling around the SYK binding site.

When conformers are generated in silico, the coordinates can be determined from co-crystals of an SYK binding site bound to a ligand. In one embodiment, the co-crystals of Examples 1 to 7 can be used to generate conformers. In addition, one skilled in the art could use the coordinates of the SYK binding sites of the co-crystals of Examples 1 to 7 to formulate ligands. The X-ray diffraction data obtained from the co-crystals of Examples 1 to 7 can be analyzed to generate coordinates by methods well know in the art, which are summarized in the section "Determination of SYK Coordinates" of this specification.

The three-dimensional conformer can be used to identify features on the ligand that interact with the residues lining the binding site of SYK. This process of identifying features can be performed by displaying the three-dimensional structure of SYK (using the SYK X-ray data provided herein) with a ligand on a computer and identifying groups that interact with the binding site of SYK. This can be done by measuring distances between atoms, or measuring angles formed by atoms. The groups that interact with the binding site are then classified by any suitable manner, such as by their functional, chemical, or physical properties. For example, the groups can be classified as, but not limited to, hydrogen bond donors; hydrogen bond acceptors, hydrophobic groups, ionizable groups or as aromatic rings. Other ways of classifying groups can be by polarity and charge. One skilled in the art will recognize that any suitable manner can be used for classifying the groups. The class to which a group belongs is the "feature." For example, if a phenyl group of a ligand interacts with the binding site of SYK, the phenyl group can be classified as an aromatic ring or as a six-membered unsaturated ring. In such a case, the feature of the ligand that covers the phenyl group is called an aromatic ring feature or a six-membered unsaturated ring feature.

Once features of one or more ligands are determined from three-dimensional structures, a pharmacophore can be formulated by comparing and compiling the features of the ligands that interact with specific locations in the binding site and generating a molecule comprising one or more the identified features that interact with the SYK binding site. For example, if an aromatic ring feature is required at a specific location on one or more ligands to permit interaction with a specific hydrophobic residue in the binding site, a pharmacophore can be formulated that has an aromatic ring at such a position. By continuing this analysis for different locations on a ligand, a pharmacophore can be formulated that comprises a feature for each location on a ligand. In some instances, a single location can have more than one feature so that more than one pharmacophores can be derived from a set of ligands.

Testing or evaluating compatibility of a compound with a pharmacophore comprises comparing the one or more features on a compound with the one or more features at similar locations on the pharmacophore. This may require rotation and translation of a compound to achieve the best alignment with the pharmacophore (i.e., lowest energy conformation or interaction) in order to effectively compare the features. A compound is said to be compatible with a pharmacophore if the features on the compound match with the features on the pharmacophore. For example, compatibility occurs if an aromatic ring in a location on a compound matches with an aromatic ring in the same location in the pharmacophore. In such a case, the compound is said to fit the constraints of the pharmacophore. Testing or evaluating compatibility of a compound with a pharmacophore is synonymous with finding the optimum fit of a compound with a pharmacophore.

Some embodiments used an SYK with a E440Q mutation to minimize the crystal packing due to the surface charge of some residues. Mutated residues should be at least 15 Å away from an active site or binding pocket and do not affect the generation of a pharmacophore model.

DEFINITIONS

As used herein, the following terms shall have the following meanings.

The amino acid notations used herein for the twenty genetically encoded amino acids are as follows. alanine: A or Ala; arginine: R or Arg; asparagine: N or Asn; aspartic acid: D or Asp; cysteine: C or Cys; glutamine: Q or Gln; glutamic acid: E or Glu; glycine: G or Gly; histidine: H or His; isoleucine: I or Ile; leucine: L or Leu; lysine: K or Lys; methionine: M or Met; phenylalanine: F or Phe; proline: P or Pro; serine: S or Ser; threonine: T or Thr; tryptophan: W or Trp; tyrosine: Y or Tyr; and valine: V or Val.

The symbol "-" means a single bond and "=" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

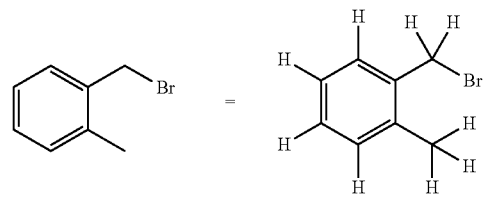

"Alkyl" is intended to include linear, branched, or cyclic hydrocarbon structures and combinations thereof, inclusively. For example, "C$_6$ alkyl" may refer to an n-hexyl, iso-hexyl, cyclobutylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. A "C$_0$" alkyl (as in "C$_0$-C$_6$alkyl") is a covalent bond. Exemplary alkyl groups are those of C$_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "C$_4$ alkyl" is meant to include n-butyl, sec-butyl, isobutyl, t-butyl, isobutenyl and but-2-ynyl groups; and for example, "propyl" or "C$_3$ alkyl" each include n-propyl, propenyl, and isopropyl.

"Alkoxy", "alkyloxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Aryl" refers to aromatic six- to fourteen-membered carbocyclic ring, for example, benzene, naphthalene, indane, tetralin, fluorene and the like, univalent substituents. As univalent substituents, the aforementioned ring examples are named, phenyl, naphthyl, indanyl, tetralinyl, and fluorenyl. Aryl groups can be mono-, bi-, or tricyclic.

When a group is referred to as "$C_1$-$C_6$ alkyl-aryl" or "$C_0$-$C_6$ alkyl-aryl", an aryl moiety is attached to a parent structure via an alkylene group. Examples include benzyl, phenethyl, and the like. Both the aryl and the corresponding alkylene portion of an "$C_1$-$C_6$ alkyl-aryl" or "$C_0$-$C_6$ alkyl-aryl" group may be optionally substituted.

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent may be a monocyclic, bicyclic or tricyclic ring system, which may include fused or bridged ring systems as well as spirocyclic systems; and the nitrogen, phosphorus, carbon or sulfur atoms in the heterocyclyl group may be optionally oxidized to various oxidation states. In a specific example, the group —$S(O)_{0-2}$—, refers to —S— (sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring substituent may be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Heteroaryl" refers specifically to an aromatic heterocyclyl group.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," optional substitution may occur on both the "$C_{1-8}$alkyl" portion and the "aryl" portion of the molecule may or may not be substituted. A list of exemplary optional substitutions is presented below in the definition of "substituted."

"Substituted" alkyl, aryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that may or may not have one or more substituents, and each of the substituents may or may not have one or more substituents. But, the substituents of the substituents may not be substituted.

"Hydrophilic Amino Acid" refers to an amino acid having a side chain exhibiting a hydrophobicity of up to about zero according to the normalized consensus hydrophobicity scale of Eisenberg et al. (1984) J. Mol. Biol. 179:125-42. Typically, hydrophilic amino acids exhibit favorable interaction with water. Genetically encoded hydrophilic amino acids include Thr (T), Ser (S), His (H), Glu (E), Asn (N), Gln (O), Asp (D), Lys (K) and Arg (R). Non-genetically encoded hydrophilic amino acids include the D-isomers of the above-listed genetically-encoded amino acids, ornithine (Orn), 2,3-diaminobutyric acid (Dab) and homoserine (hSer).

"Acidic Amino Acid" refers to a hydrophilic amino acid having a side chain pK value of up to about 7 under physiological conditions. Acidic amino acids typically have negatively charged side chains at physiological pH due to loss of a hydrogen ion. Genetically encoded acidic amino acids include Glu (E) and Asp (D). Non-genetically encoded acidic amino acids include D-Glu (e) and D-Asp (d).

"Basic Amino Acid" refers to a hydrophilic amino acid having a side chain pK value of greater than 7 under physiological conditions. Basic amino acids typically have positively charged side chains at physiological pH due to association with hydronium ion. Genetically encoded basic amino acids include His (H), Arg (R) and Lys (K). Non-genetically encoded basic amino acids include the D-isomers of the above-listed genetically-encoded amino acids, ornithine (Orn) and 2,3-diaminobutyric acid (Dab).

"Polar Amino Acid" refers to a hydrophilic amino acid having a side chain that is uncharged at physiological pH, but which comprises at least one covalent bond in which the pair of electrons shared in common by two atoms is held more closely by one of the atoms. Genetically encoded polar amino acids include Asn (N), Gln (O), Ser (S), and Thr (T). Non-genetically encoded polar amino acids include the D-isomers of the above-listed genetically-encoded amino acids and homoserine (hSer).

"Hydrophobic Amino Acid" refers to an amino acid having a side chain exhibiting a hydrophobicity of greater than zero according to the normalized consensus hydrophobicity scale of Eisenberg et al. (1984) J. Mol. Biol. 179:125-42. Typically, hydrophobic amino acids do not exhibit favorable interaction with water. Genetically encoded hydrophobic amino acids include Pro (P), Ile (I), Phe (F), Val (V), Leu (L), Trp (W), Met (M), Ala (A), Gly (G) and Tyr (Y). Non-genetically encoded hydrophobic amino acids include the D-isomers of the above-listed genetically-encoded amino acids, norleucine (Nle) and N-methyl valine (MeVal).

"Aromatic Amino Acid" refers to a hydrophobic amino acid having a side chain comprising at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$-C$_6$) alkyl, (C$_1$-C$_6$) alkenyl, or (C$_1$-C$_6$) alkynyl. Genetically encoded aromatic amino acids include Phe (F), Tyr (Y), Trp (W) and His (H). Non-genetically encoded aromatic amino acids include the D-isomers of the above-listed genetically-encoded amino acids.

"Apolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A). Non-genetically encoded apolar amino acids include the D-isomers of the above-listed genetically-encoded amino acids, norleucine (Nle) and N-methyl valine (MeVal).

"Aliphatic Amino Acid" refers to a hydrophobic amino acid having an aliphatic hydrocarbon side chain. Genetically encoded aliphatic amino acids include Ala (A), Val (V), Leu (L) and Ile (I). Non-genetically encoded aliphatic amino acids include the D-isomers of the above-listed genetically-encoded amino acids, norleucine (Nle) and N-methyl valine (MeVal).

As will be appreciated by those of skill in the art, the above-defined classes or categories are not mutually exclusive. Thus, amino acids having side chains exhibiting two or more physical-chemical properties can be included in multiple categories. For example, amino acid side chains having aromatic groups that are further substituted with polar substituents, such as Tyr (Y), may exhibit both aromatic hydrophobic properties and polar or hydrophilic properties, and could therefore be included in both the aromatic and polar categories. Typically, amino acids will be categorized in the class or classes that most closely define their net physical-chemical properties. The appropriate categorization of any amino acid will be apparent to those of skill in the art.

Other amino acid residues not specifically mentioned herein can be readily categorized based on their observed physical and chemical properties in light of the definitions provided herein.

When a group or atom is described as "associated" or "interacts" or makes "contact" with another group or atom, it refers to the situation whereby two or more molecules are in close proximity to each other so as to influence each other. An association, interaction or contact may be by any recognized physicochemical means. For example, two atoms or groups of atoms may be close to each other so as to form a non-covalent or covalent interaction. Examples of non-covalent interactions are hydrogen-bonding, van der Waals, electrostatic or hydrophobic or hydrophilic interactions. A hydrogen bond is formed by three atoms: one hydrogen atom and two electronegative atoms (often N or O). The hydrogen atom is covalently bonded to one of electronegative atoms, called the hydrogen bond donor. The other electronegative atom is referred to as the hydrogen bond acceptor. The hydrogen atom is not covalently bonded to the other electronegative atom, but is situated in close proximity. The two electronegative atoms may take up some electron density from the hydrogen atom, so that each electronegative atom carries a partial negative charge and the hydrogen atom carries a partial positive charge. The hydrogen atom and the hydrogen bond acceptor attract each other as a result of these partial charges. The distance from one electronegative atom to the other is usually between 2.6 to 3.6 Å. The bond energy of hydrogen bonds depends on the nature of the donor and acceptor as well as their environment. Typically, bond energies range from 1 kcal/mol to 5 kcal/mol.

Hydrophobic regions or hydrophobic cores are composed of hydrophobic atoms or groups of atoms. For example, a hydrophobic region may be composed of hydrophobic or apolar amino acids. Hydrophobic regions do not favorably interact with water.

Hydrophilic regions or hydrophilic cores are composed of hydrophilic atoms or groups of atoms. For example, a hydrophilic region may be composed of hydrophilic, acid, basic, ionized or polar amino acids. Hydrophilic regions exhibit favorable interaction with water.

Ionizable regions are composed of atoms or groups of atoms that are capable of accepting or donating one or more electrons so as to assume negative or positive charges. For example, ionizable regions may be composed of acid or basic amino acids.

Aromatic rings are group of atoms that form carbocyclic or heterocyclic rings with delocalized $\pi$ electrons over the entire ring system. Aromatic rings may be monocyclic or polycyclic. Aromatic rings may be composed of, for example, benzene, naphthalene, indane, tetralin, fluorene and the like.

A training set is collection of compounds that share one or more common characteristics. For example, the training set of compounds used for generating conformers of SYK comprises compounds that are ligands for SYK. In addition, such ligands may further be limited to ligands that bind to SYK with a certain strength, for example, the ligands exhibit SYK inhibitory activity measured by their $IC_{50}$ values in the range of 500 nM or less.

A "conformer" or "conformation" refers to a three-dimensional construct. A conformer may be, for example, a polypeptide alone or in association with one or more ligands. Such ligands include, by way of example and not limitation, cofactors, ligands, substrates, substrate analogues, inhibitors, allosteric affecters, etc. A conformer may also refer to a computer generated and represented association between a peptide and a ligand. A conformer also refers to a co-crystal or co-complex that exists in crystalline form or in aqueous form. A conformer is a three-dimensional construct that defines a particular structure or configuration as a function of time. Thus, a conformer as used herein includes all possible three-dimensional structures or configuration that can be obtained as time is varied. Co-crystals or co-complexes refer to a conformer that comprises a polypeptide in association with one or more ligands. Co-crystals include native co-crystals and heavy-atom derivative co-crystals.

A "scaffold" is a lead group of atoms that comprises points of attachments for substituents that comprise one or more features. A scaffold itself may also comprise one or more features. Thus, a scaffold refers to any chemical moiety that comprises points of attachments for substituents that can interact with a binding site. For example, a scaffold for designing SYK inhibitors include, but are not restricted to, an atom, pyrimidine, benzene, indole, hydrogen bond donors; hydrogen bond acceptors, hydrophobic groups, hydrophilic groups, ionizable groups, aromatic groups, polar groups, apolar groups, and adenine. By adding various substituents at the points of attachment of a scaffold, a structure can be derived that binds to and modulates the activity of SYK.

A "binding site" or "binding pocket" refers to a site or region in SYK that, because of its shape, likely associates with a substrate or ligand. This site may include, for example, residues involved in catalysis, as well as residues involved in binding a substrate. Inhibitors may bind to the residues of the binding site. A binding site or binding pocket may also be an active site or regulatory site. In SYK, the binding site includes one or more of the following amino acid residues: Leu377, Gly378, Phe382, Val385, Ala400, Val433, Met448, Glu449, Met450, Ala451, Glu452, Gly454, Pro455, Lys458, Leu501, Asp512, Lys375, Ser379, Gly380, Gly383, Thr384, Lys402, Leu453, Arg498, Asn499, and Ser511. A binding site also refers to a region in SYK which associates with a ligand such as a natural substrate, non-natural substrate, inhibitor, substrate analog, agonist, antagonist, protein, co-factor, small molecule, various ions or water. A binding site has an internal cavity sufficient to bind a molecule and may be used as a target for binding drugs.

A ligand is a molecule, group, structure or compound that binds to a binding site. A ligand comprises specific features at different locations along the ligand. For example, a ligand may be comprised of a phenyl group linked to a furanyl group which is linked to an alkyl group. Each of the phenyl, furanyl and alkyl groups define locations on the ligand. In turn, each of the phenyl, furanyl and alkyl groups are themselves classifiable as features. Thus, such a ligand can be describe or classified, for example, as having an aromatic ring in one location followed by a hydrophilic group in a second location which is followed by a hydrophobic group in a third location. Of course, such a ligand can be describe in any number of ways depending on how each group is classified and positioned relative to each other. Thus, a pharmacophore can be formulated from one or more ligands by defining the class of the group in a specific location on the one or more ligands.

The term "rotamer" refers to low energy conformations. The use of a library of rotamers facilitates determining or modeling a structure by testing the most likely conformation that would fit into a model, for example, a pharmacophore model. The use of rotamers of the correct low energy in modeling allows for structures that are more likely to be correct. Rotamer libraries and programs are publicly available. For example, Lovell S. C., Word J. M., Richardson J. S. and Richardson D. C., The Penultimate Rotamer Library, Proteins: Structure Function and Genetics 40 389-408 (2000).

"Crystal" refers to a composition comprising a polypeptide in crystalline form. The term "crystal" includes native crystals, heavy-atom derivative crystals and co-crystals, as defined herein.

"Native Crystal" refers to a crystal wherein the polypeptide is substantially pure. As used herein, native crystals do not include crystals of polypeptides comprising amino acids that are modified with heavy atoms, such as crystals of selenomethionine mutants, selenocysteine mutants or other mutants.

"AMP-PNP" refers to adenylyl imidodiphosphate, a non-hydrolyzable analogue of ATP.

"Heavy-atom Derivative Crystal" refers to a crystal wherein the polypeptide is in association with one or more heavy-metal atoms. As used herein, heavy-atom derivative crystals include native crystals into which a heavy metal atom is soaked, as well as crystals of selenomethionine mutants and selenocysteine mutants.

"Apo-crystal" refers to a crystal wherein the polypeptide is substantially pure and substantially free of compounds or ligands that might form a co-crystal with the polypeptide such as cofactors, ligands, substrates, substrate analogues, inhibitors, allosteric affecters, etc.

"Diffraction Quality Crystal" refers to a crystal that is well-ordered and of a sufficient size such that it produces measurable diffraction to at least 3 Åresolution, preferably to at least 2 Å resolution, and most preferably to at least 1.5 Åresolution or lower. Diffraction quality crystals include native crystals, heavy-atom derivative crystals, and co-crystals.

"Unit Cell" refers to the smallest and simplest volume element (i.e., parallelepiped-shaped block) of a crystal that is completely representative of the unit or pattern of the crystal, such that the entire crystal can be generated by translation of the unit cell. The dimensions of the unit cell are defined by six numbers: dimensions a, b and c and the angles are defined as α, β, and γ (Blundell et al., Protein Crystallography, 83-84, Academic Press. 1976). A crystal is an efficiently packed array of many unit cells.

"Crystal Lattice" refers to the array of points defined by the vertices of packed unit cells.

"Space Group" refers to the set of symmetry operations of a unit cell. In a space group designation (e.g., C2) the capital letter indicates the lattice type and the other symbols represent symmetry operations that can be carried out on the unit cell without changing its appearance.

"Asymmetric Unit" refers to the largest aggregate of molecules in the unit cell that possesses no symmetry elements that are part of the space group symmetry, but that can be juxtaposed on other identical entities by symmetry operations.

"Structure coordinates" or "three-dimensional coordinates" refers to mathematical coordinates derived from mathematical equations related to the patterns obtained on diffraction of a monochromatic beam of X-rays by the atoms (scattering centers) of a SYK crystals or co-crystals. The diffraction data are used to calculate an electron density map of the repeating unit of the crystal. The electron density maps are used to establish the positions of the individual atoms within the unit cell of the crystal. Thus, the structural coordinates define the arrangement of atoms in space.

Determination of SYK Coordinates

Methods for the crystallization and analysis of crystals to determine the three-dimensional coordinates are well known in the art. One skilled in the art would know where to find such methods, and would also know how to use such methods. One skilled in the art would also know how to modify the conditions of such methods to crystallize and determine the coordinates for particular proteins and their ligands. For example, such methods are described in U.S. Patent Application No. 2004/0253178, which is incorporated by reference in its entirety.

I. Crystallization

One skilled in the art may use various methods known in the art may be used to produce the native and heavy-atom derivative crystals of the present invention. Methods known in the art include, but are not limited to, batch, liquid bridge, dialysis, and vapor diffusion (see, e.g., McPherson, Crystallization of Biological Macromolecules, Cold Spring Harbor Press, New York, 1998; McPherson, Eur. J. Biochem. 189:1-23, 1990; Weber, Adv. Protein Chem. 41:1-36, 1991; Methods in Enzymology 276:13-22, 100-110; 131-143, Academic Press, San Diego, 1997).

Generally, native crystals are grown by dissolving substantially pure polypeptide in an aqueous buffer containing a precipitant at a concentration just below that necessary to precipitate the protein. Examples of precipitants include, but are not limited to, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof. Water is removed by controlled evaporation to produce precipitating conditions, which are maintained until crystal growth ceases.

In one embodiment, native crystals are grown by vapor diffusion in hanging drops or sitting drops (McPherson, Preparation and Analysis of Protein Crystals, John Wiley, New York, 1982; McPherson, Eur. J. Biochem. 189:1-23, 1990). Generally, up to about 25 or up to about 5 μl, 3 μl, or 2 μl, of substantially pure polypeptide solution is mixed with a volume of reservoir solution. The ratio may vary according to biophysical conditions, for example, the ratio of protein volume: reservoir volume in the drop may be 1:1, giving a precipitant concentration about half that required for crystallization. Those of ordinary skill in the art recognize that the drop and reservoir volumes may be varied within certain biophysical conditions and still allow crystallization. In the sitting drop method, the polypeptide/precipitant solution is allowed to equilibrate in a closed container with a larger aqueous reservoir having a precipitant concentration optimal for producing crystals. In the hanging drop method, the polypeptide solution mixed with reservoir solution is suspended as a droplet underneath, for example, a cover slip, which is sealed onto the top of the reservoir. For both methods, the sealed container is allowed to stand, usually, for example, for up to 2-6 weeks, until crystals grow. It is preferable to check the drop periodically to determine if a crystal has formed. One way of viewing the drop is using, for example, a microscope. One method of checking the drop, for high throughput purposes, includes methods that may be found in, for example, U.S. Utility patent application Ser. No. 10/042,929, filed Oct. 18, 2001, entitled "Apparatus and Method for Identification of Crystals By In-situ X-Ray Diffraction." Such methods include, for example, using an automated apparatus comprising a crystal growing incubator, an X-ray source adjacent to the crystal growing incubator, where the X-ray source is configured to irradiate the crystalline material grown in the crystal growing incubator, and an X-ray detector configured to detect the presence of the diffracted X-rays from crystalline material grown in the incubator. In more preferred methods, a charge coupled video camera is included in the detector system.

Those having skill in the art will recognize that the above-described crystallization conditions can be varied. Such variations may be used alone or in combination, and may include various volumes of protein solution and reservoir solution known to those of ordinary skill in the art. Other buffer solutions may be used such as Tris, imidazole, or MOPS buffer, so long as the desired pH range is maintained, and the chemical composition of the buffer is compatible with crystal formation.

Heavy-atom derivative crystals can be obtained by soaking native crystals in mother liquor containing salts of heavy metal atoms and can also be obtained from SeMet and/or SeCys mutants, as described above for native crystals.

Mutant proteins may crystallize under slightly different crystallization conditions than wild-type protein, or under very different crystallization conditions, depending on the nature of the mutation, and its location in the protein. For example, a non-conservative mutation may result in alteration of the hydrophilicity of the mutant, which may in turn make the mutant protein either more soluble or less soluble than the wild-type protein. Typically, if a protein becomes more hydrophilic as a result of a mutation, it will be more soluble than the wild-type protein in an aqueous solution and a higher precipitant concentration will be needed to cause it to crystallize. Conversely, if a protein becomes less hydrophilic as a result of a mutation, it will be less soluble in an aqueous solution and a lower precipitant concentration will be needed to cause it to crystallize. If the mutation happens to be in a region of the protein involved in crystal lattice contacts, crystallization conditions may be affected in more unpredictable ways.

II. Characterization of SYK Crystals and Co-Crystals

Unit cell dimensions a crystal are defined by six variables that include the lengths of the three unique edges (a, b, and c)

and the three unique angles (α, β, and γ). The type of unit cell that comprises a crystal is determined by the values of these variables.

When a crystal is exposed to an X-ray beam, the electrons of the molecules in the crystal diffract the beam so that a sphere of diffracted X-rays around the crystal is formed. The angle at which diffracted beams emerge from the crystal can be computed by treating diffraction as reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, namely, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. For example, the 235 planes cut the edge of each unit cell into halves, the b edge of each unit cell into thirds, and the c edge of each unit cell into fifths. Planes that are parallel to the bc face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, may be recorded of a still crystal (not rotated) to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections are recorded on the detector, resulting in a diffraction pattern.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal must be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

Once the dimensions of the unit cell are determined, the likely number of polypeptides in the asymmetric unit can be deduced from the size of the polypeptide, the density of the average protein, and the typical solvent content of a protein crystal, which is usually in the range of 30-70% of the unit cell volume (Matthews, J. Mol. Biol. 33(2):491-97, 1968). The diffraction pattern is related to the three-dimensional shape of the molecule by a Fourier transform. The process of determining the solution is in essence a re-focusing of the diffracted X-rays to produce a three-dimensional image of the molecule in the crystal. Since re-focusing of X-rays cannot be done with a lens at this time, it is done via mathematical operations.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded in order to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. In one embodiment, a complete dataset is collected using one crystal. In another embodiment, a complete dataset is collected using more than one crystal of the same type.

III. Determination of Crystal Phases

The information in a dataset is used to determine the three-dimensional structure of the molecule in the crystal. The phase information may be acquired by methods described below in order to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, the positions of heavy atoms bound to the molecules in the heavy-atom derivative crystal are determined, and this information is then used to obtain the phase information necessary to elucidate the three-dimensional structure of a native crystal (Blundell et al., Protein Crystallography, Academic Press, 1976).

A second method of obtaining phase information is by molecular replacement, which is a method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules comprising the new crystal (Lattman, Methods in Enzymology 115:55-77, 1985; Rossmann, "The Molecular Replacement Method," Int. Sci. Rev. Ser. No. 13, Gordon & Breach, New York, 1972).

A third method of phase determination is multi-wavelength anomalous diffraction or MAD. In this method, X-ray diffraction data are collected at several different wavelengths from a single crystal containing at least one heavy atom with absorption edges near the energy of incoming X-ray radiation. The resonance between X-rays and electron orbitals leads to differences in X-ray scattering that permits the locations of the heavy atoms to be identified, which in turn provides phase information for a crystal of a polypeptide. A detailed discussion of MAD analysis can be found in Hendrickson, Trans. Am. Crystallogr. Assoc., 21:11, 1985; Hendrickson et al., EMBO J. 9:1665, 1990; and Hendrickson, Science, 254:51-58, 1991).

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen, et al., Acta Cryst., D56:431-41, 2000.

A fifth method of determining phase information is single isomorphous replacement with anomalous scattering or SIRAS. SIRAS combines isomorphous replacement and anomalous scattering techniques to provide phase information for a crystal of a polypeptide. X-ray diffraction data are collected at a single wavelength, usually from both a native and a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is extracted from both the location of the heavy atoms and from anomalous scattering of the heavy atoms. A detailed discussion of SIRAS analysis can be found in North, Acta Cryst. 18:212-16, 1965; Matthews, Acta Cryst. 20:82-86, 1966; Methods in Enzymology 276:530-37, 1997.

IV. Determination of Electron Density Map

The phase information is combined with the diffraction data to produce an electron density map, an image of the electron clouds surrounding the atoms that constitute the molecules in the unit cell. The higher the resolution of the data, the more distinguishable the features of the electron density map, because atoms that are closer together are resolvable. A model of the macromolecule is then built into the electron density map with the aid of a computer, using as a guide all available information, such as the polypeptide sequence and the established rules of molecular structure and stereochemistry. Interpreting the electron density map is a process of finding the chemically reasonable conformation that fits the map precisely.

After a model is generated, a structure is refined. Refinement is the process of minimizing the function $\phi$, which is the difference between observed and calculated intensity values (measured by an R-factor), and which is a function of the position, temperature factor, and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the function $\phi$ converges on a minimum wherein the model fits the electron density map and is stereochemically and conformationally reasonable. During the last stages of refinement, ordered solvent molecules are added to the structure.

V. Structure Coordinates

The molecular structure coordinates can be used in molecular modeling and design, as described more fully below. The present invention encompasses the structure coordinates and other information, e.g., amino acid sequence, connectivity tables, vector-based representations, temperature factors, etc., used to generate the three-dimensional structure of the polypeptide for use in the software programs described below and other software programs.

The invention includes methods of producing computer readable databases comprising the three-dimensional molecular structure coordinates of certain molecules, including, for example, the SYK structure coordinates, the structure coordinates of binding pockets or active sites of SYK, or structure coordinates of compounds capable of binding to SYK. The databases of the present invention may comprise any number of sets of molecular structure coordinates for any number of molecules, including, for examples, structure coordinates of one molecule. In other embodiments, the databases of the present invention may comprise structure coordinates of a compound or compounds that have been identified by virtual screening to bind to a SYK binding pocket, or other representations of such compounds such as, for example, a graphic representation or a name. By "database" is meant a collection of retrievable data. The invention encompasses machine readable media embedded with or containing information regarding the three-dimensional structure of a crystalline polypeptide and/or model, such as, for example, its molecular structure coordinates, described herein, or with subunits, domains, and/or, portions thereof such as, for example, portions comprising active sites, accessory binding sites, and/or binding pockets in either liganded or unliganded forms. Alternatively, the information may be that of identifiers which represent specific structures found in a protein. As used herein, "machine readable medium" refers to any medium that can be read and accessed directly by a computer or scanner. Such media may take many forms, including but not limited to, non-volatile, volatile and transmission media. Non-volatile media, i.e., media that can retain information in the absence of power, includes a ROM. Volatile media, i.e., media that cannot retain information in the absence of power, includes a main memory. Transmission media includes coaxial cables, copper wire and fiber optics, including the wires that comprise the bus. Transmission media can also take the form of carrier waves; i.e., electromagnetic waves that can be modulated, as in frequency, amplitude or phase, to transmit information signals. Additionally, transmission media can take the form of acoustic or light waves, such as those generated during radio wave and infrared data communications.

Such media also include, but are not limited to: magnetic storage media, such as floppy discs, flexible discs, hard disc storage medium and magnetic tape; optical storage media such as optical discs or CD-ROM; electrical storage media such as RAM or ROM, PROM (i.e., programmable read only memory), EPROM (i.e., erasable programmable read only memory), including FLASH-EPROM, any other memory chip or cartridge, carrier waves, or any other medium from which a processor can retrieve information, and hybrids of these categories such as magnetic/optical storage media. Such media further include paper on which is recorded a representation of the molecular structure coordinates, e.g., Cartesian coordinates, that can be read by a scanning device and converted into a format readily accessed by a computer or by any of the software programs described herein by, for example, optical character recognition (OCR) software. Such media also include physical media with patterns of holes, such as, for example, punch cards, and paper tape.

A variety of data storage structures are available for creating a computer readable medium having recorded thereon the molecular structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, macromolecular Crystallographic Information File ("mmCIF") and Protein Data Bank ("PDB") format (Research Collaboratory for Structural Bioinformatics; Cambridge Crystallographic Data Centre format; Structure-data ("SD") file format (MDL Information Systems, Inc.; Dalby, et al., J. Chem. Inf. Comp. Sci., 32:244-55, 1992; and line-notation, e.g., as used in SMILES (Weininger, J. Chem. Inf. Comp. Sci. 28:31-36, 1988). Methods of converting between various formats read by different computer software will be readily apparent to those of skill in the art, e.g., BABEL (v. 1.06, Walters & Stahl, © 1992, 1993, 1994).

All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

A computer may be used to display the structure coordinates or the three-dimensional representation of the protein or peptide structures, or portions thereof, such as, for example, portions comprising active sites, accessory binding sites, and/or binding pockets, in either liganded or unliganded form, of the present invention. The term "computer" includes, but is not limited to, mainframe computers, personal computers, portable laptop computers, and personal data assistants ("PDAs") which can store data and independently run one or more applications, i.e., programs. The computer may include, for example, a machine readable storage medium of the present invention, a working memory for storing instructions for processing the machine-readable data encoded in the machine readable storage medium, a central processing unit operably coupled to the working memory and to the machine readable storage medium for processing the machine readable information, and a display operably coupled to the central processing unit for displaying the structure coordinates or the three-dimensional representation. The information contained in the machine-readable medium may be in the form of, for example, X-ray diffraction data, structure coordinates, electron density maps, or ribbon structures. The information may also include such data for co-complexes between a compound and a protein or peptide of the present invention.

The computers used in the present invention may also include, for example, a central processing unit, a working memory which may be, for example, random-access memory (RAM) or "core memory," mass storage memory (for example, one or more disk drives or CD-ROM drives), one or more cathode-ray tube ("CRT") display terminals or one or more LCD displays, one or more keyboards, one or more input lines, and one or more output lines, all of which are interconnected by a conventional bi-directional system bus. Machine-readable data of the present invention may be inputted and/or outputted through a modem or modems connected by a telephone line or a dedicated data line (either of which may include, for example, wireless modes of communication). The input hardware may also (or instead) comprise CD-ROM drives or disk drives. Other examples of input devices are a keyboard, a mouse, a trackball, a finger pad, or cursor direction keys. Output hardware may also be implemented by conventional devices. For example, output hardware may include a CRT, or any other display terminal, a printer, or a disk drive. The CPU coordinates the use of the various input and output devices, coordinates data accesses from mass storage and accesses to and from working memory, and determines the order of data processing steps. The computer may use various software programs to process the data of the present invention. Examples of many of these types of software are discussed throughout the present application.

Those of skill in the art will recognize that a set of structure coordinates is a relative set of points that define a shape in three dimensions. Therefore, two different sets of coordinates could define the identical or a similar shape. Also, minor changes in the individual coordinates may have very little effect on the peptide's shape. Minor changes in the overall structure may have very little to no effect, for example, on the binding pocket, and would not be expected to significantly alter the nature of compounds that might associate with the binding pocket.

Although Cartesian coordinates are important and convenient representations of the three-dimensional structure of a polypeptide, other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, and a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all inter-atomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

The structural information of a compound that binds a SYK of the invention may be similarly stored and transmitted as described above for structural information of SYK.

VI. Analysis of Three-Dimensional Coordinates

Structure information can be used in a variety of computational or computer-based methods to design, screen for, and/or identify pharmacophores and/or compounds that bind SYK or a portion or fragment thereof.

When designing or identifying pharmacophores and/or compounds that may associate with a SYK, the binding pockets are often analyzed. The term "binding pocket," refers to a region of a protein that, because of its shape, likely associates with a chemical entity or compound. A binding pocket may be the same as an active site. A binding pocket of a protein is usually involved with binding ligands or substrates, and is often the basis for the protein's activity. A binding pocket may refer to an active site. Many drugs act by associating with a binding pocket of a protein. A binding pocket may comprise amino acid residues that line the cleft of the pocket. Those of ordinary skill in the art will recognize that the numbering system used for other isoforms of SYK may be different, but that the corresponding amino acids may be determined with a homology software program known to those of ordinary skill in the art. A binding pocket homolog comprises amino acids having structure coordinates that have a root mean square deviation of the binding pocket amino acids of up to about 1.5 Å, preferably up to about 1.25 Å, more preferably up to about 1 Å, more preferably up to about 0.75 Å, more preferably up to about 0.5 Å, and even more preferably up to about 0.25 Å.

Where a binding site or regulatory site is said to comprise amino acids having particular structural coordinates, the site may comprise any amino acid residues having similar functional or structural properties, and that have either the same three-dimensional structural coordinates, or have an rmsd of less than 1.5 Å.

The crystals and structure coordinates may be used for rational drug design to identify and/or design pharmacophores and compounds that bind SYK to develop new therapeutic agents. For example, a high resolution X-ray structure of a crystallized protein saturated with ligands will show the locations of the ligand and solvent molecules around the protein, and in particular at or near binding pockets. This information can then be used to design pharmacophores that bind at the binding pockets by identifying features of the ligand that interact with residues lining the binding pockets. The pharmacophores can then be used to design compounds that can bind SYK.

The structure may also be computationally screened with a plurality of molecules to determine their ability to bind to the SYK at various sites. Such compounds can be used as targets or leads in medicinal chemistry efforts to identify, for example, inhibitors of potential therapeutic importance (Travis, Science, 262:1374, 1993). The three dimensional structures of such compounds may be superimposed on a three dimensional representation of SYKKD or an active site or binding pocket thereof to assess whether the compound fits spatially into the representation and hence the protein. Structural information produced by such methods and concerning a compound or a portion of such a compound that fits may be stored in a machine readable medium. Alternatively, one or more descriptors of a compound or a portion thereof, that fits may be stored in a machine readable medium. Examples of descriptors include chemical name or abbreviation, chemical or molecular formula, chemical structure, hydrogen bond donor, a hydrogen bond acceptor, a hydrophobic region, a ionizable region, an aromatic ring feature, the distance separating features, and/or other identifying information. As an non-limiting example, if the three dimensional structure of phenyl is found to fit the binding site of SYK, the structural information of phenyl, or the portion that fits, may be stored for further use and given the descriptor of aromatic ring. Other identifying information for phenyl may also be used to represent it.

In an analogous manner, the structure of SYK or the binding site can be used to computationally screen small molecule databases for chemical entities or compounds that can bind in whole, or in part, to SYK. In this screening, the quality of fit of such entities or compounds to the binding site may be judged either by shape complementarity or by estimated interaction energy (Meng, et al., J. Comp. Chem. 13:505-24, 1992).

The design of compounds that bind to and/or modulate SYK, for example that inhibit SYK generally involves consideration of two factors. First, the compound must be capable of physically and structurally associating, either covalently or non-covalently with SYK. For example, covalent interactions may be important for designing irreversible or suicide inhibitors of a protein. Non-covalent molecular interactions important in the association of SYK with the compound include hydrogen bonding, ionic interactions and van der Waals and hydrophobic interactions. Second, the compound must be able to assume a conformation and orientation in relation to the binding pocket, that allows it to associate with SYK. Although certain portions of the compound will not directly participate in this association with SYK, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with SYK.

Computer modeling techniques may be used to assess the potential modulating or binding effect of a chemical compound on SYK. If computer modeling indicates a strong interaction, the molecule may then be synthesized and tested for its ability to bind to SYK and inhibit its activity.

Modulating or other binding compounds of SYK may be computationally evaluated and designed by means of a series of steps in which chemical groups or fragments are screened and selected for their ability to associate with the individual binding pockets or other areas of SYK. Several methods are available to screen chemical groups or fragments for their ability to associate with SYK. This process may begin by visual inspection of, for example, the active site on the computer screen based on the SYK coordinates. Selected fragments or chemical groups may then be positioned in a variety of orientations, or docked, within an individual binding pocket of SYK (Blaney, J. M. and Dixon, J. S., Perspectives in Drug Discovery and Design, 1:301, 1993). Manual docking may be accomplished using software such as Insight II (Accelrys, San Diego, Calif.) MOE; CE (Shindyalov, Ind., Bourne, P E, "Protein Structure Alignment by Incremental Combinatorial Extension (CE) of the Optimal Path," Protein Engineering, 11:739-47, 1998); and SYBYL (Molecular Modeling Software, Tripos Associates, Inc., St. Louis, Mo., 1992), followed by energy minimization and molecular dynamics with standard molecular mechanics force fields, such as CHARMM (Brooks, et al., J. Comp. Chem. 4:187-217, 1983). More automated docking may be accomplished by using programs such as DOCK (Kuntz et al., J. Mol. Biol., 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., J. Mol. Biol. 245: 43-53, 1995); and FLEXX (Tripos, St. Louis, Mo.; Rarey, M., et al., J. Mol. Biol. 261:470-89, 1996); AMBER (Weiner, et al., J. Am. Chem. Soc. 106: 765-84, 1984) and $C^2$ MMFF (Merck Molecular Force Field; Accelrys, San Diego, Calif.). Other appropriate programs are described in, for example, Halperin, et al.

As is evident from the foregoing, a vast array of techniques for evaluating and manipulating data are known, readily available, and routinely usable by those of ordinary skill in the art. Thus, all publications recited in this specification are hereby incorporated by reference in their entirety. To the extent of any inconsistencies or contradictions between such publications and the explicit teachings of this specification, the explicit teachings of this specification take precedent and shall be followed.

In one embodiment, discovering SYK inhibitors uses a pharmacophore model and comprising the steps of: (a) providing a first virtual library of at least one scaffold, each scaffold comprising at least one attachment point for a substituent, each scaffold including a plurality of atoms defined by a set of three-dimensional coordinates; (b) providing a second virtual library of a plurality of substituents, each of said plurality of substituents being described by a set of discrete conformations, wherein each conformation is a rotamer; (c) adding all rotamers from said second virtual library to each attachment point of each scaffold to form at least one structure; (d) assigning pharmacophore descriptors to all possible groups of at least one atom on said rotamers and on said scaffold; (e) testing the compatibility of each rotamer in each structure with a pharmacophore model; (f) eliminating a specific rotamer if said specific rotamer cannot exist in at least one combination compatible with each pharmacophore model; (g) eliminating a specific scaffold if said scaffold descriptor assignments are not compatible with at least one pharmacophore model; and (h) identifying at least one molecule from a combination of remaining rotamers and a remaining scaffold.

Specialized computer programs may also assist in the process of selecting fragments or chemical groups. These include DOCK; GOLD; LUDI; FLEXX (Tripos, St. Louis, Mo.; Rarey, M., et al., J. Mol. Biol. 261:470-89, 1996); and GLIDE (Eldridge, et al., J. Comput. Aided Mol. Des. 11:425-45, 1997; Schrodinger, Inc., New York). Other appropriate programs are described in, for example, Halperin, et al., (Portland, Org.).

Once suitable chemical groups or fragments have been selected, they can be assembled into a single compound or inhibitor. Assembly may proceed by visual inspection of the relationship of the fragments to each other in the three-dimensional image displayed on a computer screen in relation to the structure coordinates of SYK. This would be followed by manual model building using software such as SYBYL, (Tripos, St. Louis, Mo.); Insight II (Accelrys, San Diego, Calif.); and MOE (Chemical Computing Group, Inc., Montreal, Canada). Other appropriate programs are described in, for example, Halperin, et al.

Useful programs to aid one of skill in the art in connecting the individual chemical groups or fragments include, for example: CAVEAT (Bartlett et al., "CAVEAT: A Program to Facilitate the Structure-Derived Design of Biologically Active Molecules". In Molecular Recognition in Chemical and Biological Problems, Special Pub., Royal Chem. Soc. 78:182-96, 1989; and available from the University of California, Berkeley, Calif.); 3D Database systems such as ISIS or MACCS-3D (MDL Information Systems, San Leandro, Calif.); HOOK (Eisen et al., Proteins: Struct., Funct., Genet., 19:199-221, 1994; and available from Accelrys, Inc., San Diego, Calif.); and LUDI (Bohm, J. Comp. Aid. Molec. Design 6:61-78, 1992; and available from Accelrys, Inc., San Diego, Calif.).

Instead of proceeding to build a SYK inhibitor in a stepwise fashion one fragment or chemical group at a time, as described above, SYK binding compounds may be designed as a whole using either an empty binding site as a model or optionally including some portion(s) of a known inhibitor as a scaffold.

Other molecular modeling techniques may also be employed. See, for example, Cohen et al., J. Med. Chem. 33:883-94, 1990; Navia & Murcko, Current Opinions in Structural Biology 2:202-10, 1992; Balbes et al., Reviews in Computational Chemistry, 5:337-80, 1994, (Lipkowitz and Boyd, Eds.) (VCH, New York); and Guida, Curr. Opin. Struct. Biol. 4:777-81, 1994.

During design and selection of compounds by the above methods, the efficiency with which that compound may bind to SYK may be tested and optimized by computational evaluation. For example, a compound that has been designed or selected to function as a SYK inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective SYK inhibitor may demonstrate a relatively small difference in energy between its bound and free states (i.e., it must have a small deformation energy of binding and/or low conformational strain upon binding). Thus, the most efficient SYK inhibitors should, for example, be designed with a deformation energy of binding of not greater than 10 kcal/mol, for example, not greater than 7 kcal/mol, for example, not greater than 5 kcal/mol and, for example, not greater than 2 kcal/mol. SYK inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

A compound selected or designed for binding to SYK may be further computationally optimized so that in its bound state it would, for example, lack repulsive electrostatic interaction with the target protein. Non-complementary electrostatic interactions include repulsive charge-charge, dipole-dipole and charge-dipole interactions. Specifically, the sum of all electrostatic interactions between the inhibitor and the protein when the inhibitor is bound to it may make a neutral or favorable contribution to the enthalpy of binding.

Specific computer software is available in the art to evaluate compound deformation energy and electrostatic interaction. Examples of programs designed for such uses include: Gaussian 94, revision C (Frisch, Gaussian, Inc., Pittsburgh, Pa. © 1995); AMBER, version 7.1 (Kollman, University of California at San Francisco, © 2002); QUANTA/CHARMM (Accelrys, Inc., San Diego, Calif. ©1995); Insight II/Discover (Accelrys, Inc., San Diego, Calif. ©1995); DelPhi (Accelrys, Inc., San Diego, Calif. © 1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Once a SYK binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to SYK by the same computer methods described in detail above. Methods of structure-based drug design are described in, for example, Klebe, G., J. Mol. Med. 78:269-81, 2000); Hol. W. G. J., Angewandte Chemie (Int'l Edition in English) 25:767-852, 1986; and Gane, P. J. and Dean, P. M., Current Opinion in Structural Biology, 10:401-04, 2000.

The present invention also provides means for the preparation of a compound the structure of which has been identified or designed, as described above, as binding SYK or binding pocket thereof. Where the compound is already known or designed, the synthesis thereof may readily proceed by means known in the art. Alternatively, compounds that match the structure of one or more pharmacophores as described above may be prepared by means known in the art.

In an alternative embodiment, the production of a compound may proceed by introduction of one or more desired chemical groups by attachment to an initial compound which binds SYK or an active site or binding pocket thereof and which has, or has been modified to contain, one or more chemical moieties for attachment of one or more desired chemical groups. The initial compound may be viewed as a "scaffold" comprising at least one moiety capable of binding or associating with one or more residues of SYK or an active site or binding pocket thereof.

The initial compound may be a flexible or rigid "scaffold", optionally containing a linker for introduction of additional chemical moieties. Various scaffold compounds can be used, including, but not limited to, aliphatic carbon chains, pyrrolidinones, sulfonamidopyrrolidinones, cycloalkanonedienes including cyclopentanonedienes, cyclohexanonedienes, and cycloheptanonedienes, carbazoles, imidazoles, benzimidazoles, pyridine, isoxazoles, isoxazolines, benzoxazinones, benzamidines, pyridinones and derivatives thereof. Other scaffolds are described in, for example, Klebe, G., J. Mol. Med. 78: 269-281 (2000); Maignan, S. and Mikol, V., Curr. Top. Med. Chem. 1: 161-174 (2001); and U.S. Pat. No. 5,756,466 to Bemis et al. The scaffold compound used may, for example, be one that comprises at least one moiety capable of binding or associating with one or more residues of SYK or binding pocket thereof.

Chemical moieties on the scaffold compound that permit attachment of one or more desired functional chemical groups may undergo conventional reactions by coupling, substitution, and electrophilic or nucleophilic displacement. For example, the moieties may be those already present on the compound or readily introduced. Alternatively, a variant of the scaffold compound comprising the moieties is utilized initially. As a non-limiting example, the moiety can be a leaving group which can readily be removed from the scaffold compound. Various moieties can be used, including but not limited to pyrophosphates, acetates, hydroxy groups, alkoxy groups, tosylates, brosylates, halogens, and the like. In another embodiment of the invention, the scaffold compound is synthesized from readily available starting materials using conventional techniques. (See e.g., U.S. Pat. No. 5,756,466 for general synthetic methods). Chemical groups are then introduced into the scaffold compound to increase the number of interactions with one or more residues of SYK or binding pocket thereof.

Subsets of the molecular structure coordinates can be used in any of the above methods. Particularly useful subsets of the coordinates include, but are not limited to, coordinates of single domains, coordinates of residues lining an active site or binding pocket, coordinates of residues that participate in important protein-protein contacts at an interface, and alpha-carbon coordinates. For example, the coordinates of one domain of a protein that contains a binding site may be used to design inhibitors that bind to that site, even though the protein is fully described by a larger set of atomic coordinates. Therefore, a set of atomic coordinates that define the entire polypeptide chain, although useful for many applications, do not necessarily need to be used for the methods described herein. For example, the kinase domain comprising 1358 to N635 may be used.

Pharmaceutical Compositions and Administration

Pharmaceutical compositions comprising SYK modulators, such as inhibitors, are useful, for example, for treating diseases and conditions that involve SYK activity. Pharmaceutical compositions containing SYK modulators may also be useful to modify the activity of SYK homologs.

Pharmaceutical compositions include compositions wherein the active ingredients are contained in an effective amount to achieve its intended purpose. The active ingredient can be the compound itself or one of its pharmaceutically acceptable salts. Methods for the determination of the effective amounts are known to those skilled in the art. In addition to the active ingredients, pharmaceutical compositions may comprise pharmaceutically acceptable carriers. Pharmaceutically acceptable carriers comprise excipients and auxiliaries that facilitate processing of the active compounds into preparations that can be used in pharmaceutical compositions.

The compounds and the pharmaceutical compositions can be formulated for oral administration, and may be in the form of tablets, capsules, solutions such as syrups and elixirs, gels such as hydrogels, inorganic hydrogels and organic gels, emulsions, suspensions, hard lozenges, soft lozenges, or any other suitable mean, such as a medicated candies. The capsules can be push-fit capsules made of gelatin, as well as soft, sealed capsules made of gelatin, and a plasticizer, such as, but not limited to, glycerol or sorbitol. The push-fit capsules can contain the active ingredients in admixture with fillers, binders, and/or lubricants and, optionally, stabilizers. Fillers include lactose or other kinds of sugars, binders include starches, and lubricants include talc or magnesium stearate. One skilled in the art would recognize that fillers, binders, lubricants and stabilizers can include other substances which are known to those skilled in the art. Soft capsules may comprise the active compounds dissolved or suspended in suitable liquids, such as fatty oils, liquid paraffin, or liquid polyethylene glycols (PEGS), and optionally, stabilizers.

Compounds and pharmaceutical compositions of the invention may be formulated into liquid or solid dosage forms and administered systemically or locally. The compounds and pharmaceutical compositions may be delivered, for example, in a timed- or sustained-low release form as is known to those skilled in the art. Techniques for formulation and administration may be found in *Remington: The Science and Practice of Pharmacy* ($20^{th}$ ed.) Lippincott, Williams & Wilkins (2000). Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections.

For injection, the Compounds and pharmaceutical compositions of the invention may be formulated in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutically acceptable salts are generally well known to those of ordinary skill in the art, may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, *Remington: The Science and Practice of Pharmacy* (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Compounds and pharmaceutical compositions for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Medicated candies may be provided with suitable coatings. For example, coatings can be concentrated sugar solutions, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or coatings for identification or to characterize different combinations of active compound doses.

The compounds identified according to the invention are effective over a range of dosage. For example, dosages from 0.01 to 1000 mg per day, from 0.5 to 100 mg per day, from 1 to 50 mg per day, from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending medical care provider.

In therapeutic or diagnostic applications, the compounds of the invention can be formulated for a variety of modes of administration, including systemic, topical or localized administration. Techniques and formulations generally may be found in *Remington: The Science and Practice of Pharmacy* (20$^{th}$ ed.) Lippincott, Williams & Wilkins (2000).

EXAMPLES

The following examples serve to illustrate in a non-limiting manner the construction of conformers comprising co-crystals of SYK ligands and the SYK domain consisting of 1358 to N635 with the mutation E440Q.

Example 1

Crystal Structure of SYK Kinase (1358-N635) Containing Bound AMP-PNP Refined to 2.6 Å

Expression and Purification

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 μm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE (FIG. 1), which indicated that the protein was sufficiently pure for crystallization experiments.

Crystallization

The pooled fractions were dialyzed against 300 mM NaCl, 10 mM Hepes pH 7.5, 5 mM DTT overnight at 4° C. then concentrated to 10.4 mg/mL in a Vivaspin centrifugal concentrator (MWCO=10 kDa). Prior to crystal growth, 2 mM MgCl$_2$ and 1 mM AMP-PNP were added to the protein. Crystals were obtained at 20° C. in sitting drop plates using 1 μL of protein and 1 μL of crystallant (20% PEG 3000, 100 mM Citrate pH 5.5) equilibrated against 200 μL of crystallant in the reservoir. Plate-shaped crystals were observed after approximately 24 hours. A single crystal was transferred from the crystallization drop to a cryoprotectant containing 80% crystallant and 20% glycerol. The crystal was plunge frozen into liquid nitrogen for X-ray diffraction analysis.

Data Collection and Processing

Data were collected at the Advanced Light Source (ALS) beamline 5.0.1 using an ADSC Quantum 210 CCD detector and 1° ω-scans. The X-ray wavelength was 1.0000 Å. Intensities were integrated and scaled with the HKL2000 package. Indexing indicated a primitive orthorhombic lattice with a=40.05 Å, b=85.14, c=91.10 Å and the space group was determined to be P 2$_1$2$_1$2$_1$ based upon systematic absences h00; h=2n, 0k0; k=2n; 001; 1=2n.

Structure Solution and Refinement

The Matthew's coefficient (V$_m$) of 2.2 Å$^3$/kDa was calculated giving a solvent content of 43.9% and a single monomer in the asymmetric unit. The structure was solved by molecular replacement using MOLREP version 8.2 and the previously determined crystal structure of SYK kinase (PDB ID: 1XBA) served as the search model. Initial refinement of the model using Refmac5 version 5.2 and data from 30 Å to 2.6 Å resolution converged at R=23%, R$_{free}$=32% indicating that a correct solution was determined. Model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with the non-hydrolyzable analogue of ATP (AMP-PNP). The AMP-PNP molecule was included in the final refinement along with 33 water molecules. A list of non-bonded contacts between AMP-PNP and SYK kinase are enumerated in Table A. Refinement statistics are provided in Table B. See FIGS. 2-4 and 21 for the three-dimensional structure results.

TABLE A

Non-Bonded Contacts Between SYK E440Q and AMP-PNP

| AMP-PNP Atom | Protein or Water Atom | Distance (Å) |
|---|---|---|
| N1 | Ala 451 N | 3.12 |
| N6 | Glu 449 O | 2.66 |
| O1A | Lys 402 NZ | 2.98 |
| O2A | Water O33 | 2.10 |
| O3 | Water O30 | 2.73 |
| O1B | Asn 381 N | 2.86 |
| O2B | Lys 402 NZ | 2.81 |
| O1G | Asn 381 N | 3.11 |
| O3G | Asp 512 OD2 | 2.86 |

TABLE B

Crystallographic Data for SYK Kinase E440Q Containing AMP-PNP

| Data Collection | |
|---|---|
| Unit Cell (Å) | a = 40.05 |
|  | b = 85.14 |
|  | c = 91.10 |
| Space group | $P2_12_12_1$ |
| Resolution (Å) | 50–2.6 |
| Wavelength (Å) | 1.0000 |
| Total Reflections | 60707 |
| Unique Reflections | 9876 |
| I/(sigI)* | 16.0 (2.0) |
| $R_{merge}$ (%)* | 9.7 (53.6) |
| Completeness (%)* | 95.9 (77.2) |
| Refinement | |
| Resolution (Å) | 30–2.6 |
| Unique Reflections (working/test) | 9249/464 |
| $R_{working}/R_{free}$ (%) | 21.6/30.1 |
| Number of atoms (protein/ligand/water) | 2154/21/33 |
| r.m.s. deviation bond length (Å) | 0.016 |
| r.m.s. deviation bond angle (degrees) | 1.60 |
| Mean B factor all (Å$^2$) | 41.0 |
| Mean B factor protein (Å$^2$) | 40.1 |
| Mean B factor ligand (Å$^2$) | 50.0 |
| Mean B factor water (Å$^2$) | 33.6 |
| r.m.s. positional (Å) | 0.27 |
| Ramachandran Analysis (%) | |
| Most Favored | 90.2 |
| Additionally Allowed | 8.5 |
| Generously Allowed | 1.3 |

*Parentheses indicate values for the 2.69 Å to 2.60 Å shell.

Example 2

Crystal Structure of SYK Kinase (1358-N635) Containing Bound Cpd. No. 4 Refined to 2.2 Å

Expression and Purification

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 μm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

Crystallization

The pooled fractions were dialyzed against 300 mM NaCl, 10 mM Hepes pH 7.5, 5 mM DTT, 10% glycerol overnight at 4° C. then concentrated to 10.0 mg/mL in a Vivaspin centrifugal concentrator (MWCO=10 kDa). Crystals were obtained at 20° C. in sitting drop plates using 1 μl of protein and 1 μl of crystallant (20% PEG 3000, 10 0 mM Citrate pH 5.5, 5% DMSO and 2.8 mM Cpd. No. 4) equilibrated against 200 μl of crystallant in the reservoir. Plate-shaped crystals were observed after approximately 24 hours. Crystals was transferred to a cryoprotectant containing 20% PEG 3000, 100 mM Citrate pH 5.5, 15% glycerol then plunge frozen into liquid nitrogen for X-ray diffraction analysis.

Data Collection and Processing

Data were collected at the Advanced Photon Source (APS) Structural Biology Center (SBC) beamline 19-BM, located at Argonne National Laboratory, using a custom built CCD detector and 1° ω-scans. The X-ray wavelength was 0.97934 Å. Intensities were integrated and scaled with the HKL2000 package. Indexing indicated a primitive orthorhombic lattice with a=39.92 Å, b=84.88, c=90.98 Å and the space group was determined to be P $2_12_12_1$ based upon systematic absences h00; h=2n, 0k0; k=2n; 001; 1=2n.

Structure Solution and Refinement

Figure 5:
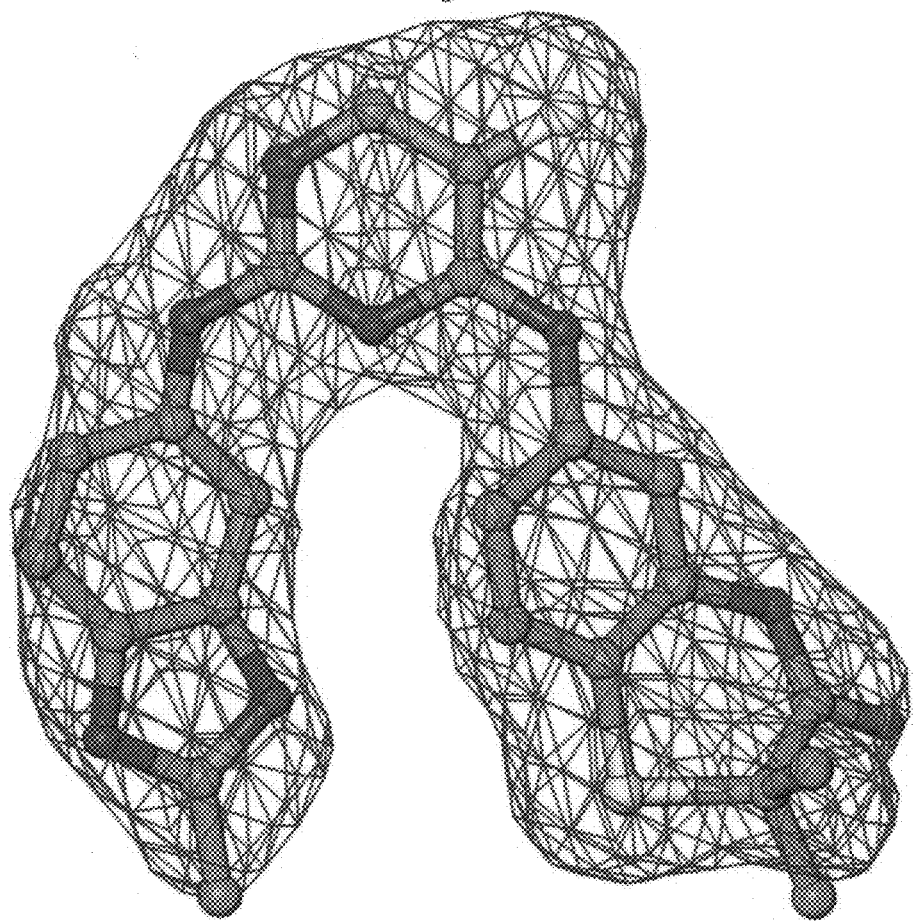
FIG. 5 illustrates the calculated Fo-Fc omit map of Cpd. No. 4 contoured at 2.5σ. The sulfur atom is represented in yellow and the fluorine atom is represented in white. Molecules are represented using this color scheme throughout the figures.
Figure 6:
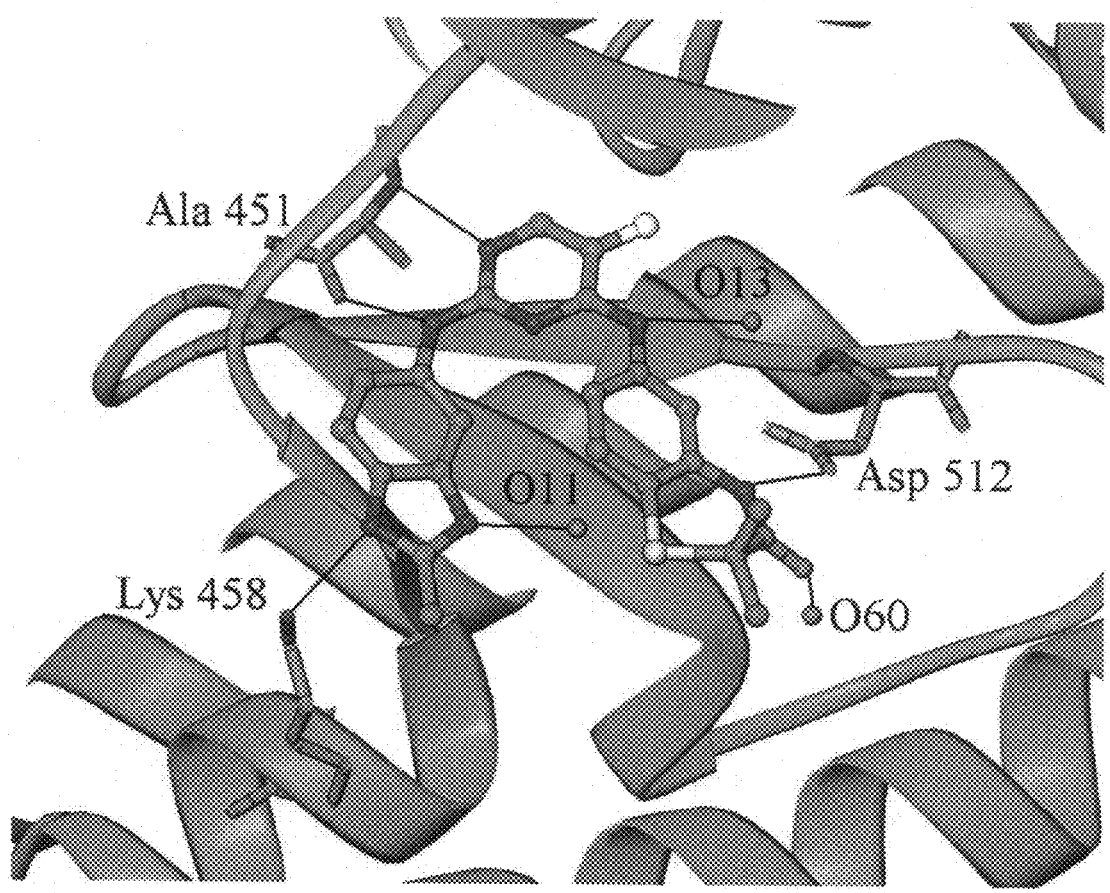
FIG. 6 illustrates the non-bonded interactions between Cpd. No. 4, SYK kinase and water molecules. Water molecules are represented by red balls and are throughout the figures.
Figure 7:
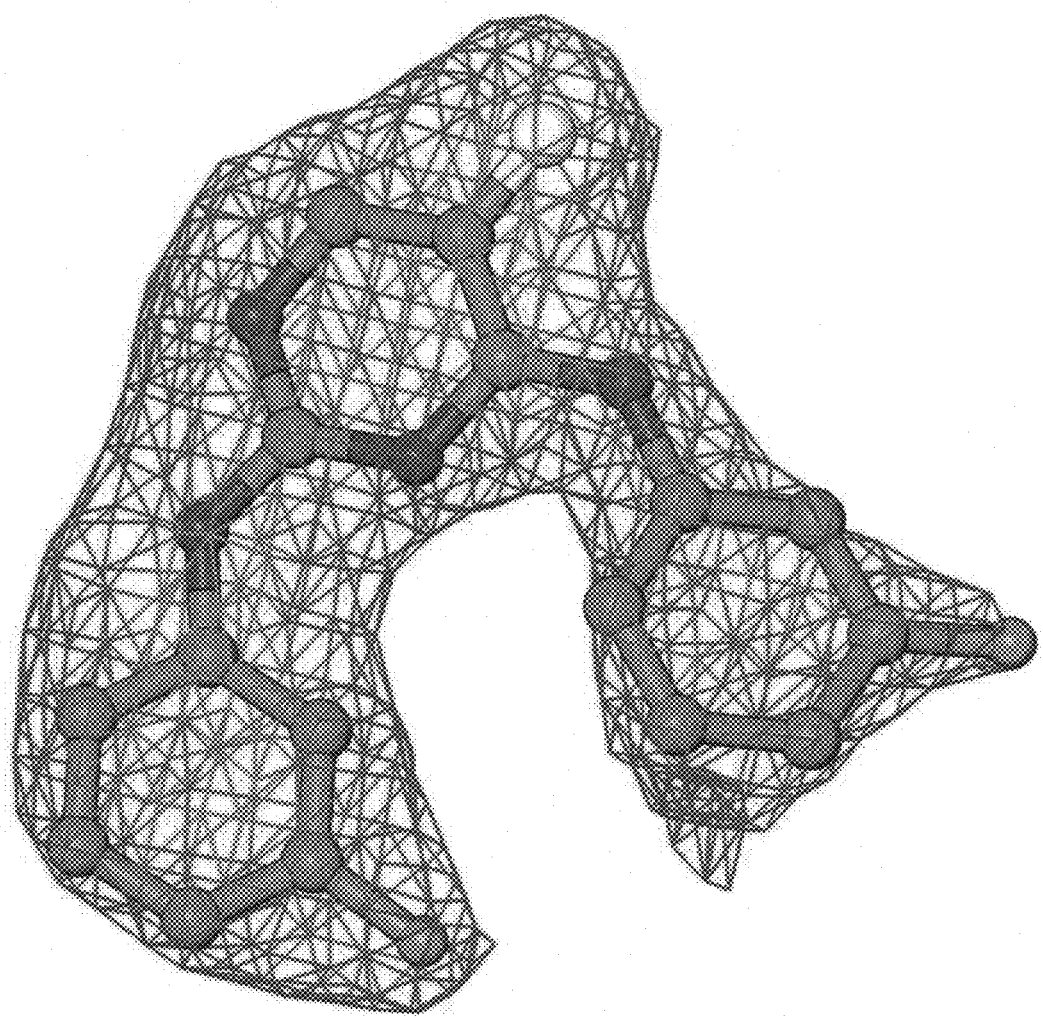
FIG. 7 illustrates the calculated Fo-Fc omit map of Cpd. No. 1 contoured at 2σ.
Figure 8:
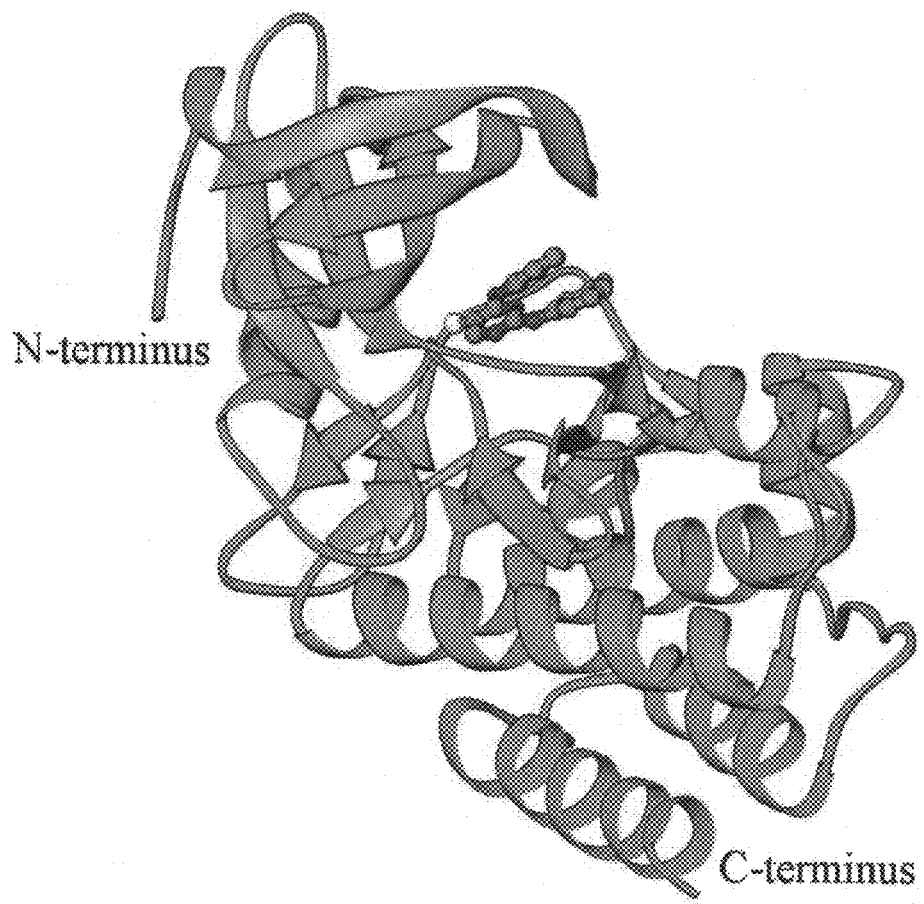
FIG. 8 illustrates Cpd. No. 1 in the ATP binding pocket of SYK kinase.
Figure 9:
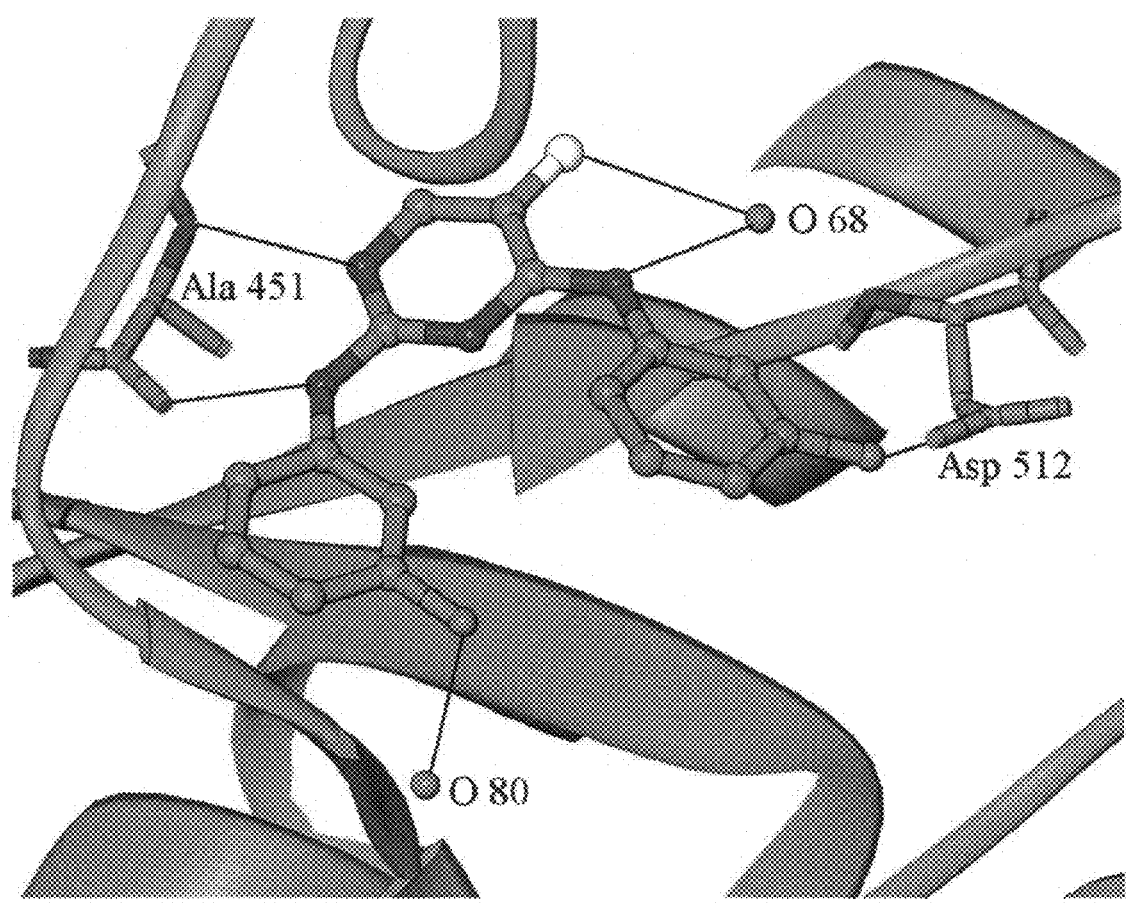
FIG. 9 illustrates the non-bonded interactions between Cpd. No. 1, SYK kinase and water molecules.
Figure 10:
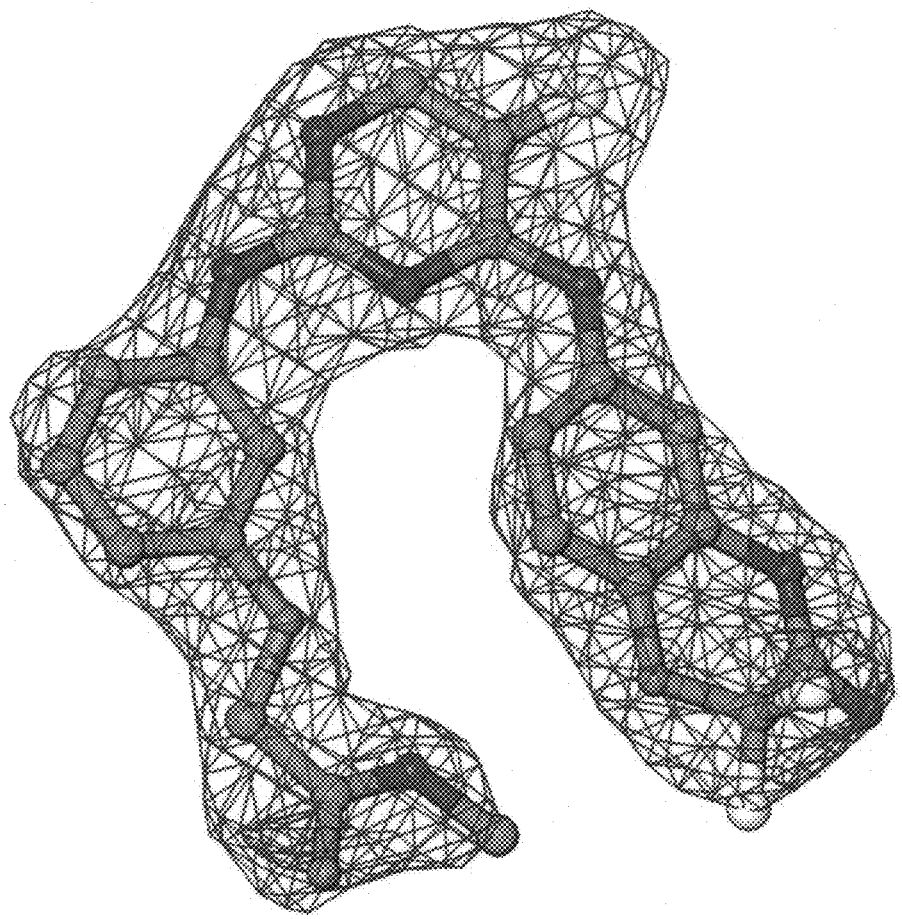
FIG. 10 illustrates the calculated Fo-Fc omit map of Cpd. No. 5 contoured at 2.5σ.
Figure 11:
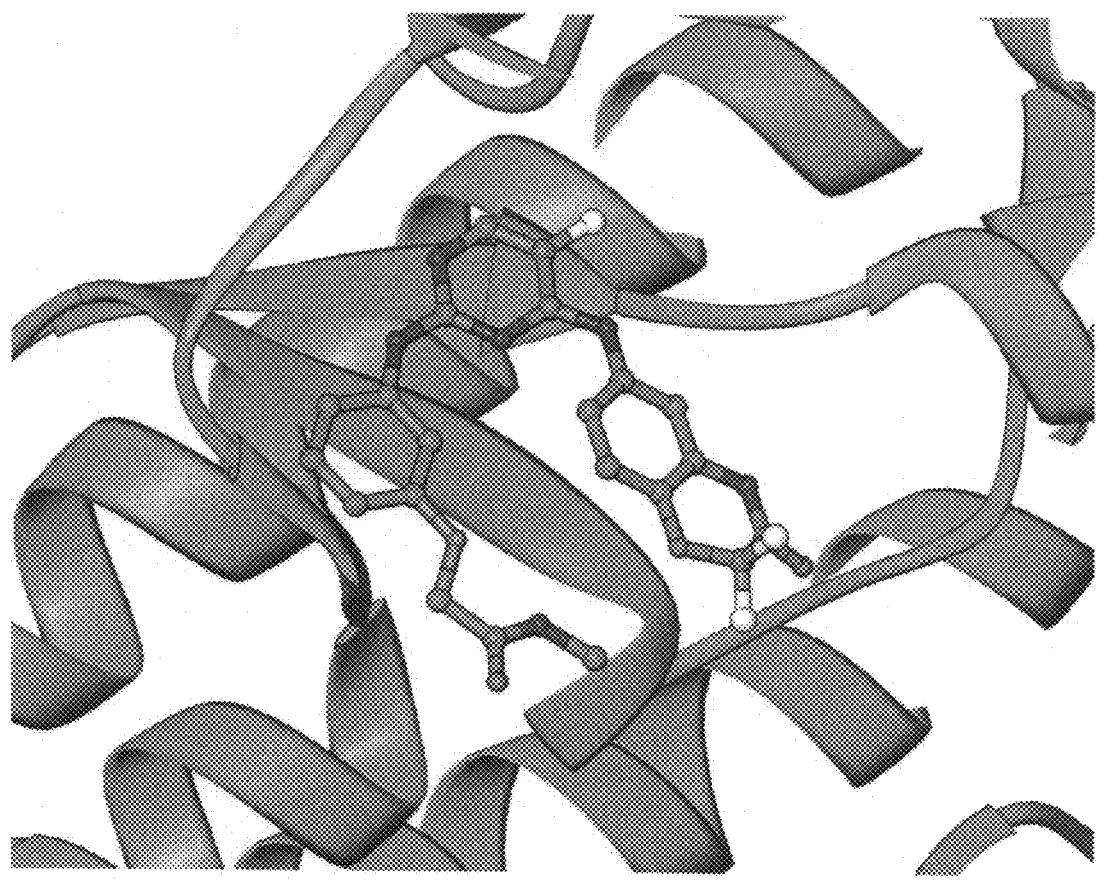
FIG. 11 illustrates Cpd. No. 5 in the ATP binding pocket of SYK kinase
Figure 12:
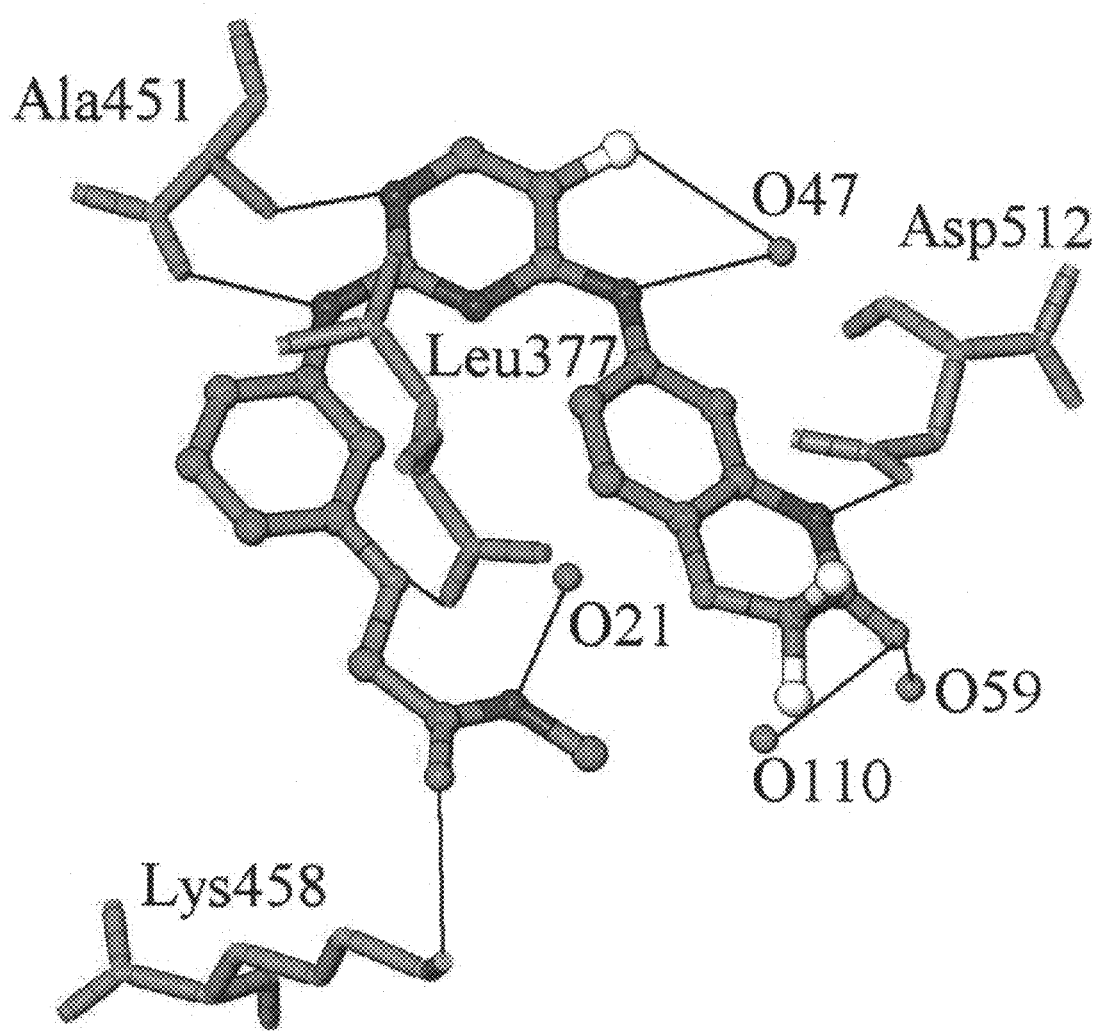
FIG. 12 illustrates the non-bonded interactions between Cpd. No. 5, SYK kinase and water molecules. Amino acids are represented by pink stick drawings.
Figure 25:
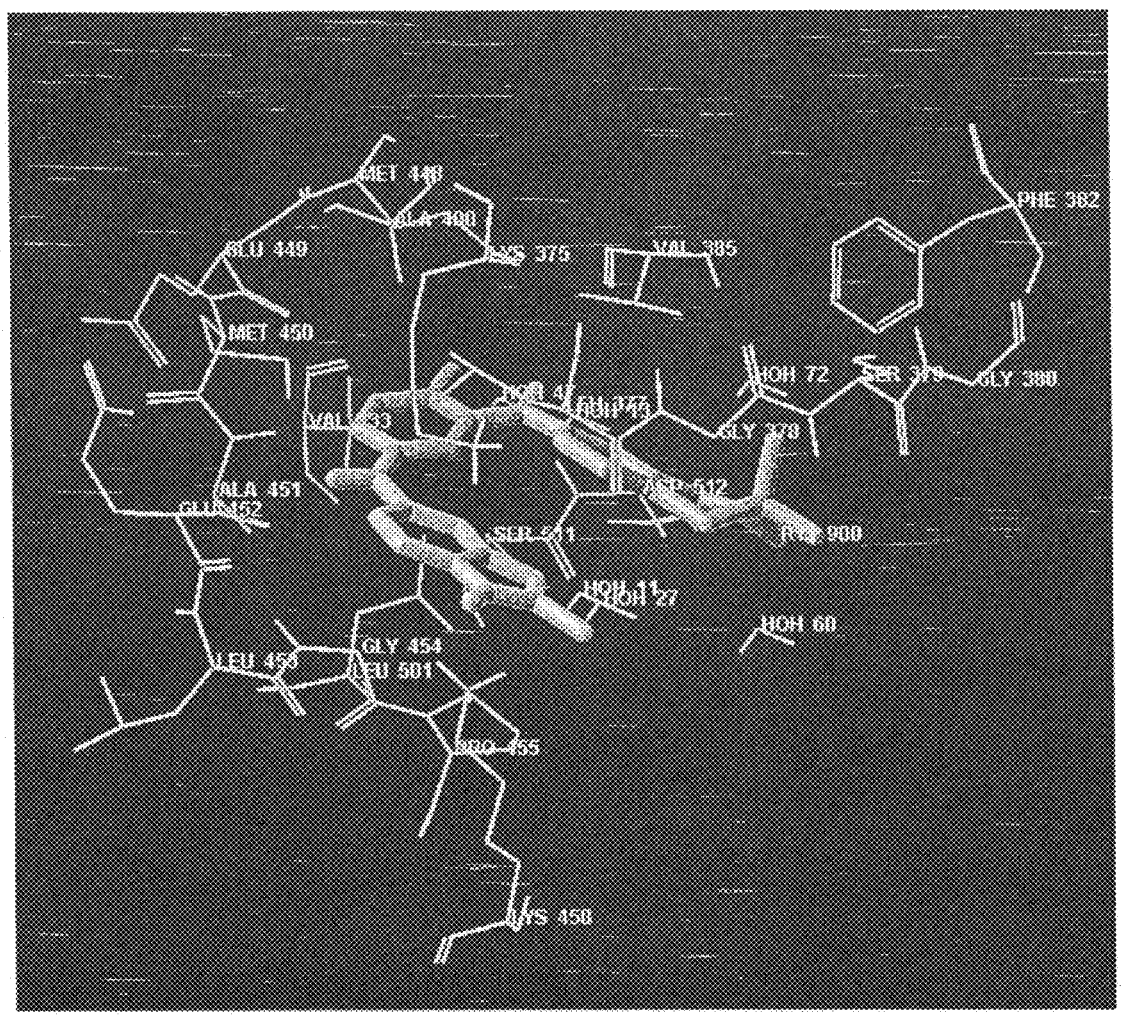
FIG. 25 illustrates the co-crystals of SYK with Cpd. No. 4.

The structure was solved by molecular replacement using MOLREP version 8.2. The previously determined crystal structure of SYK kinase E440Q containing Cpd. No. 4, refined to 2.0 Å, served as the search model. The structure was refined with Refmac5 version 5.2 using data from 30 Å to 2.2 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 4. The electron density was well-defined for the entire ligand. The Cpd. No. 4 inhibitor was included in the final refinement along with 80 water molecules. Cpd. No. 4 forms non-bonded contacts with Ala 451, Lys 458, Asp512 and water molecules #11, 13, and 60. See FIGS. 5-6 and 25 for the three-dimensional structure results. The three-dimensional coordinates are listed in Table 1 in the file entitled 05-689

Table 1.txt in CD-R 1. The non-bonded contacts are enumerated in the Table C. Refinement statistics are provided in Table D.

TABLE C

Non-Bonded Contacts Between SYK E440Q and Cpd. No. 4

| RGE13 Atom | Protein or Water Atom | Distance (Å) |
| --- | --- | --- |
| N4 | Ala 451 N | 3.08 |
| N5 | Ala 451 O | 2.88 |
| N7 | Lys 458 NZ | 2.85 |
| N1 | Asp512 OD1 | 2.79 |
| N6 | Water O11 | 2.97 |
| F2 | Water O13 | 2.92 |
| O1 | Water O60 | 2.79 |

TABLE D

Crystallographic Data for SYK Kinase E440Q Containing Cpd. No.4

| Data Collection | |
| --- | --- |
| Unit Cell (Å) | a = 39.92 |
| | b = 84.88 |
| | c = 90.98 |
| Space group | $P2_12_12_1$ |
| Resolution (Å) | 50.0 – 2.2 |
| Wavelength (Å) | 0.97934 |
| Total Reflections | 102,194 |
| Unique Reflections | 16,389 |
| I/(sigI)* | 16.7 (2.1) |
| $R_{merge}$ (%)* | 15.2 (52.1) |
| Completeness (%)* | 98.6 (92.5) |
| Refinement | |
| Resolution (Å) | 30.0 – 2.2 |
| Unique Reflections (working/test) | 15,303/812 |
| $R_{working}/R_{free}$ (%) | 21.4/27.5 |
| Number of atoms (protein/ligand/water) | 2154/32/80 |
| r.m.s. deviation bond length (Å) | 0.01 |
| r.m.s. deviation bond angle (degrees) | 1.4 |
| Mean B factor all (Å$^2$) | 40.2 |
| Mean B factor protein (Å$^2$) | 40.3 |
| Mean B factor ligand (Å$^2$) | 29.8 |
| Mean B factor water (Å$^2$) | 40.5 |
| r.m.s. positional (Å) | 0.29 |
| Ramachandran Analysis (%) | |
| Most Favored | 92.3 |
| Additionally Allowed | 7.3 |
| Generously Allowed | 0.4 |

*Parentheses indicate values for the 2.28 Å to 2.20 Å resolution shell.

Example 3

Crystal Structure of SYK Kinase (1358-N635) Containing Bound Cpd. No. 1 Refined to 2.0 Å

Expression and Purification

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 μm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

Crystallization

The pooled fractions were dialyzed against 300 mM NaCl, 10 mM Hepes pH 7.5, 5 mM DTT overnight at 4° C. then concentrated to 10.9 mg/mL in a Vivaspin centrifugal concentrator (MWCO=10 kDa). Crystals were obtained at 20° C. in sitting drop plates using 1 μl of protein and 1 μl of crystallant (20% PEG 3000, 100 mM Citrate pH 5.5) equilibrated against 200 μl of crystallant in the reservoir. Plate-shaped crystals were observed after approximately 24 hours. A single crystal was transferred from the crystallization drop to a plate containing crystallant and 11.5 mM Cpd. No. 1. The crystal was soaked for 22.5 hours in this solution. Some precipitation of Cpd. No. 1 was observed at the end of the soak. The crystal was transferred to a cryoprotectant containing 20% PEG 3000, 100 mM Citrate pH 5:5, 15% glycerol then plunge frozen into liquid nitrogen for X-ray diffraction analysis.

Data Collection and Processing

Data were collected at the Advanced Light Source (ALS) beamline 5.0.2 using an ADSC Quantum 315 CCD detector and 1° ω-scans. The X-ray wavelength was 1.0000 Å. Intensities were integrated and scaled with the HKL2000 package. Indexing indicated a primitive orthorhombic lattice with a=40.02 Å, b=85.14, c=90.26 Å and the space group was determined to be P $2_12_12_1$ based upon systematic absences h00; h=2n, 0k0; k=2n; 001; 1=2n.

Structure Solution and Refinement

A Matthew's coefficient ($V_m$) of 2.3 Å$^3$/kDa was calculated giving a solvent content of 45.3% and a single monomer in the asymmetric unit. The structure was solved by molecular replacement using MOLREP version 8.2. The previously determined crystal structure of SYK kinase E440Q containing Cpd. No. 1, refined to 2.6 Å, served as the search model. The structure was refined with Refmac5 version 5.2 using data from 30 Å to 2.0 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 1. The electron density was more detailed than the previous structure that was refined to 2.6 Å. The orientation of the phenol rings of Cpd. No. 1 was more apparent than the previous structure. Moreover, water molecules that formed non-bonded contacts to Cpd. No. 1 were discernable. The Cpd. No. 1 inhibitor was included in the final refinement along with 109 water molecules. Cpd. No. 1 molecule forms two non-bonded contacts with Ala 451. Non-bonded distances of 3.01 Å and 2.81 Å were measured between N2-N(Ala451) and N3-O(Ala 451) respectively. F1 and N4 of Cpd. No. 1 form non-bonded contacts with water molecule 068 or 3.14 Å and 2.92 Å respectively. Cpd. No. 1 O1 forms a hydrogen bond with water O 80 of 2.77 Å. A marginal non-bonded contact of 3.33 Å was observed between Cpd. No. 1 O1 and OD2 of Asp 512. Refinement statistics are provided below. See FIGS. 7-9 and 22 for the three-dimensional structure results. The three-dimensional coordinates are listed in Table 2 in the file entitled 05-689 Table 2.txt in CD-R 1. The non-bonded contacts are enumerated in the Table E. Refinement statistics are provided in Table F.

TABLE E

Non-Bonded Contacts Between SYK E440Q and Cpd. No. 1

| RGE5 Atom | Protein or Water Atom | Distance (Å) |
|---|---|---|
| F3 | Met448 C | 3.44 |
| N4 | Ala 451 N | 3.00 |
| N5 | Ala 451 O | 2.81 |
| C5 | Ala400C | 3.45 |
| OH1 | Asp512 OD1 | 3.33 |
| N6 | Water O68 | 2.92 |
| F3 | Water O68 | 3.14 |
| C5 | Leu501C | 3.50 |
| OH2 | Water O80 | 2.77 |

TABLE F

Crystallographic Data for SYK Kinase E440Q Containing Cpd. No. 1

| Data Collection | |
|---|---|
| Unit Cell (Å) | a = 40.02 |
|  | b = 85.14 |
|  | c = 90.26 |
| Space group | $P2_12_12_1$ |
| Resolution (Å) | 50.0 – 2.0 |
| Wavelength (Å) | 1.0000 |
| Total Reflections | 120,026 |
| Unique Reflections | 19,920 |
| I/(sigI)* | 28.1 (2.4) |
| $R_{merge}$ (%)* | 6.8 (46.2) |
| Completeness (%)* | 92.1 (69.9) |
| Refinement | |
| Resolution (Å) | 30.0 – 2.0 |
| Unique Reflections (working/test) | 18,821/1,009 |
| $R_{working}/R_{free}$ (%) | 20.9/26.5 |
| Number of atoms (protein/ligand/water) | 2154/23/109 |
| r.m.s. deviation bond length (Å) | 0.02 |
| r.m.s. deviation bond angle (degrees) | 1.68 |
| Mean B factor all (Å$^2$) | 37.6 |
| Mean B factor protein (Å$^2$) | 37.6 |
| Mean B factor ligand (Å$^2$) | 34.3 |
| Mean B factor water (Å$^2$) | 39.7 |
| r.m.s. positional (Å) | 0.21 |
| Ramachandran Analysis (%) | |
| Most Favored | 93.6 |
| Additionally Allowed | 6.0 |
| Generously Allowed | 0.4 |

*Parentheses indicate values for the 2.07 Å to 2.00 Å resolution shell.

Example 4

Crystal Structure of SYK Kinase (I358-N635) Containing Bound Cpd. No. 5 Refined to 2.1 Å

Expression and Purification

The Kinase domain of spleen tyrosine kinase (SYK) encompassing amino acid residues I358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 µm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

Crystallization

The pooled fractions were dialyzed against 300 mM NaCl, 10 mM Hepes pH 7.5, 5 mM DTT, 10% glycerol overnight at 4° C. then concentrated to 10.0 mg/mL in a Vivaspin centrifugal concentrator (MWCO=10 kDa). Crystals were obtained at 20° C. in sitting drop plates using 1 µl of protein and 1 µl of crystallant (20% PEG 4000, 100 mM Citrate pH 5.5) equilibrated against 200 µl of crystallant in the reservoir. Plate-shaped crystals were observed after approximately 24 hours. A single crystal was transferred from the crystallization drop to a plate containing 30% PEG 4000, 50 mM Citrate pH 5.5, 5% DMSO and 1.5 mM Cpd. No. 5. The crystal was soaked for 22.25 hours in this solution. The crystal was transferred to a cryoprotectant containing 20% PEG 4000, 100 mM Citrate pH 5.5, 15% glycerol then plunge frozen into liquid nitrogen for X-ray diffraction analysis.

Data Collection and Processing

Data were collected at the Advanced Photon Source (APS) Structural Biology Center (SBC) beamline 19-BM, located at Argonne National Laboratory, using a custom built CCD detector and 1° ω-scans. The X-ray wavelength was 0.97934 Å. Intensities were integrated and scaled with the HKL2000 package. Indexing indicated a primitive orthorhombic lattice with a=39.89 Å, b=85.07, c=89.83 Å and the space group was determined to be $P\ 2_12_12_1$ based upon systematic absences h00; h=2n, 0k0; k=2n; 001; 1=2n.

Structure Solution and Refinement

The structure was solved by molecular replacement using MOLREP version 8.2. The previously determined crystal structure of SYK kinase E440Q containing Cpd. No. 5, refined to 2.0 Å, served as the search model. The structure was refined with Refmac5 version 5.2 using data from 30 Å to 2.3 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 5. The electron density was well-defined for the entire ligand. The Cpd. No. 5 inhibitor was included in the final refinement along with 114 water molecules. Cpd. No. 5 forms non-bonded contacts with Leu377, Ala 451, Lys 458, Asp512 and water molecules #21, 47, 59 and 110. See FIGS. 10-12 and 24 for the three-dimensional structure results. The three-dimensional coordinates are listed in Table 3 in the file entitled 05-689 Table 3.txt in CD-R 1. The non-bonded contacts are enumerated in the Table G. Refinement statistics are provided in Table H.

TABLE G

Non-Bonded Contacts Between SYK E440Q and Cpd. No. 5

| RGE2 Atom | Protein or Water Atom | Distance (Å) |
|---|---|---|
| O3 | Leu377 O | 3.14 |
| N4 | Ala 451 N | 2.93 |
| N5 | Ala 451 O | 2.83 |
| O4 | Lys 458 NZ | 3.06 |
| N2 | Asp512 OD1 | 3.01 |
| N6 | Water O21 | 3.11 |
| F3 | Water O47 | 3.06 |
| N1 | Water O47 | 3.13 |
| O2 | Water O59 | 2.86 |
| O2 | Water O110 | 3.01 |

TABLE H

Crystallographic Data for SYK Kinase E440Q Containing Cpd. No. 5

| Data Collection | |
|---|---|
| Unit Cell (Å) | a = 39.89 |
| | b = 5.07 |
| | C = 9.83 |
| Space group | P2$_1$2$_1$2$_1$ |
| Resolution (Å) | 50.0 – 2.03 |
| Wavelength (Å) | 0.97934 |
| Total Reflections | 119,054 |
| Unique Reflections | 20059 |
| I/(sigI)* | 15.6 (2.0) |
| R$_{merge}$ (%)* | 10.0 (64.9) |
| Completeness (%)* | 96.6 (88.9) |
| Refinement | |
| Resolution (Å) | 30.0 – 2.1 |
| Unique Reflections (working/test) | 17,115/923 |
| R$_{working}$/R$_{free}$ (%) | 19.9/25.6 |
| Number of atoms (protein/ligand/water) | 2154/34/114 |
| r.m.s. deviation bond length (Å) | 0.02 |
| r.m.s. deviation bond angle (degrees) | 1.6 |
| Mean B factor all (Å$^2$) | 33.7 |
| Mean B factor protein (Å$^2$) | 33.6 |
| Mean B factor ligand (Å$^2$) | 32.8 |
| Mean B factor water (Å$^2$) | 36.8 |
| r.m.s. positional (Å) | 0.23 |
| Ramachandran Analysis (%) | |
| Most Favored | 94.0 |
| Additionally Allowed | 5.1 |
| Generously Allowed | 0.9 |

*Parentheses indicate values for the 2.10 Å to 2.03 Å resolution shell.

Example 5

Crystal Structure of SYK Kinase (1358-N635) Containing Bound Cpd. No. 6 Refined to 2.0 Å

Expression and Purification

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 μm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

Crystallization

The pooled fractions were dialyzed against 300 mM NaCl, 10 mM Hepes pH 7.5, 5 mM DTT, 10% glycerol overnight at 4° C. then concentrated to 10.0 mg/mL in a Vivaspin centrifugal concentrator (MWCO=10 kDa). Crystals were obtained at 20° C. in sitting drop plates using 1 μL of protein and 1 μL of crystallant (20% PEG 3000, 100 mM Citrate pH 5.5, 5% DMSO and 3.0 mM Cpd. No. 6) equilibrated against 200 μL of crystallant in the reservoir. Plate-shaped crystals were observed after approximately 24 hours. Crystals was transferred to a cryoprotectant containing 20% PEG 3000, 100 mM Citrate pH 5.5, 15% glycerol then plunge frozen into liquid nitrogen for X-ray diffraction analysis.

Data Collection and Processing

Data were collected at the Advanced Photon Source (APS) Structural Biology Center (SBC) beamline 19-BM, located at Argonne National Laboratory, using a custom built CCD detector and 1° ω-scans. The X-ray wavelength was 0.97934 Å. Intensities were integrated and scaled with the HKL2000 package. Indexing indicated a primitive orthorhombic lattice with a=39.91 Å, b=85.15, c=90.68 Å and the space group was determined to be P 2$_1$2$_1$2$_1$ based upon systematic absences h00; h=2n, 0k0; k=2n; 001; 1=2n.

Structure Solution and Refinement

Figure 17:
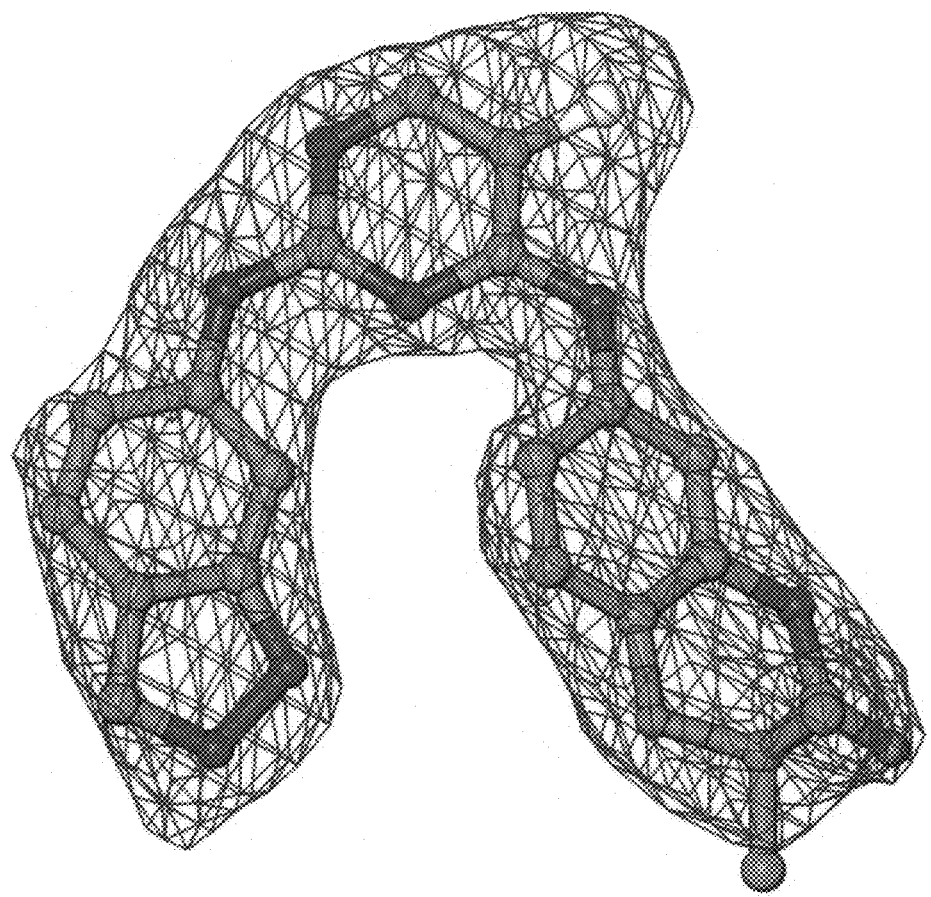
FIG. 17 illustrates the calculated Fo-Fc omit map of Cpd. No. 6 contoured at 2.5σ.
Figure 18:
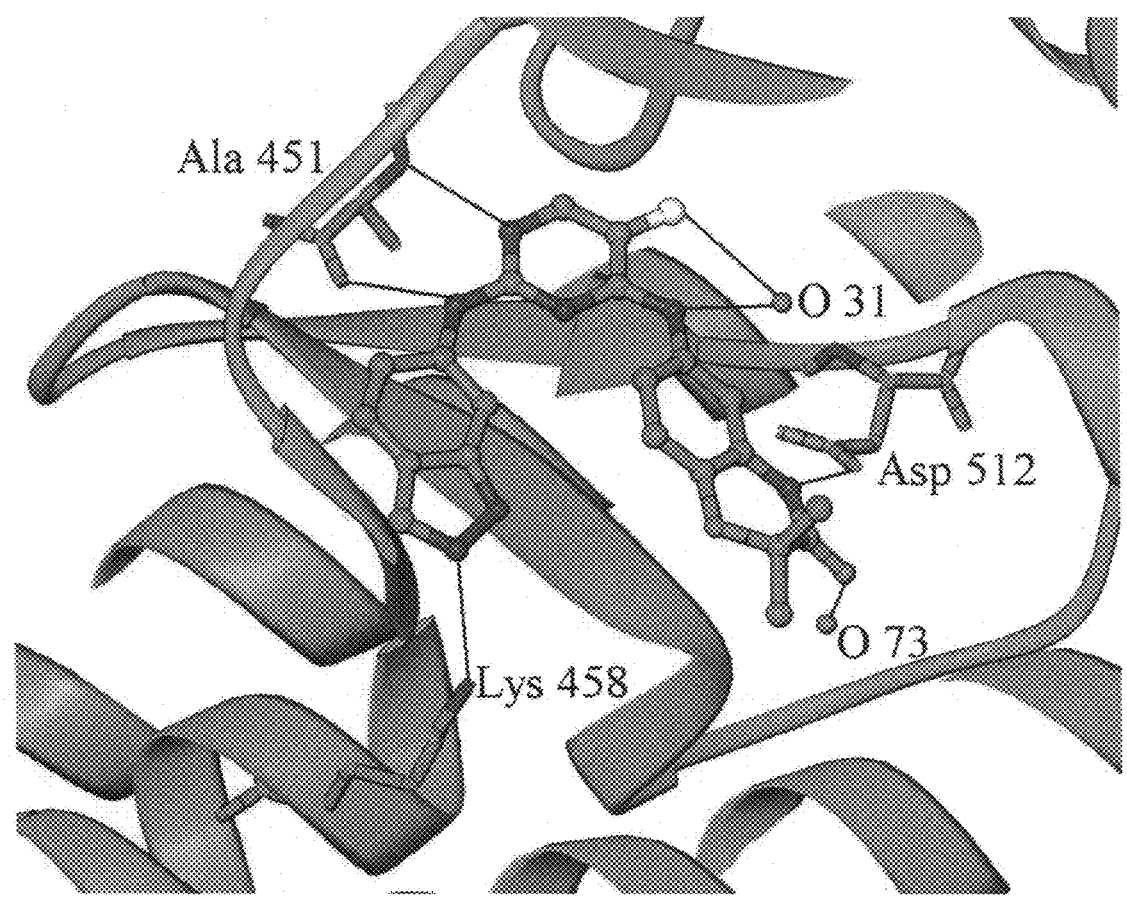
FIG. 18 illustrates the non-bonded interactions between Cpd. No. 6, SYK kinase and water molecules.
Figure 26:
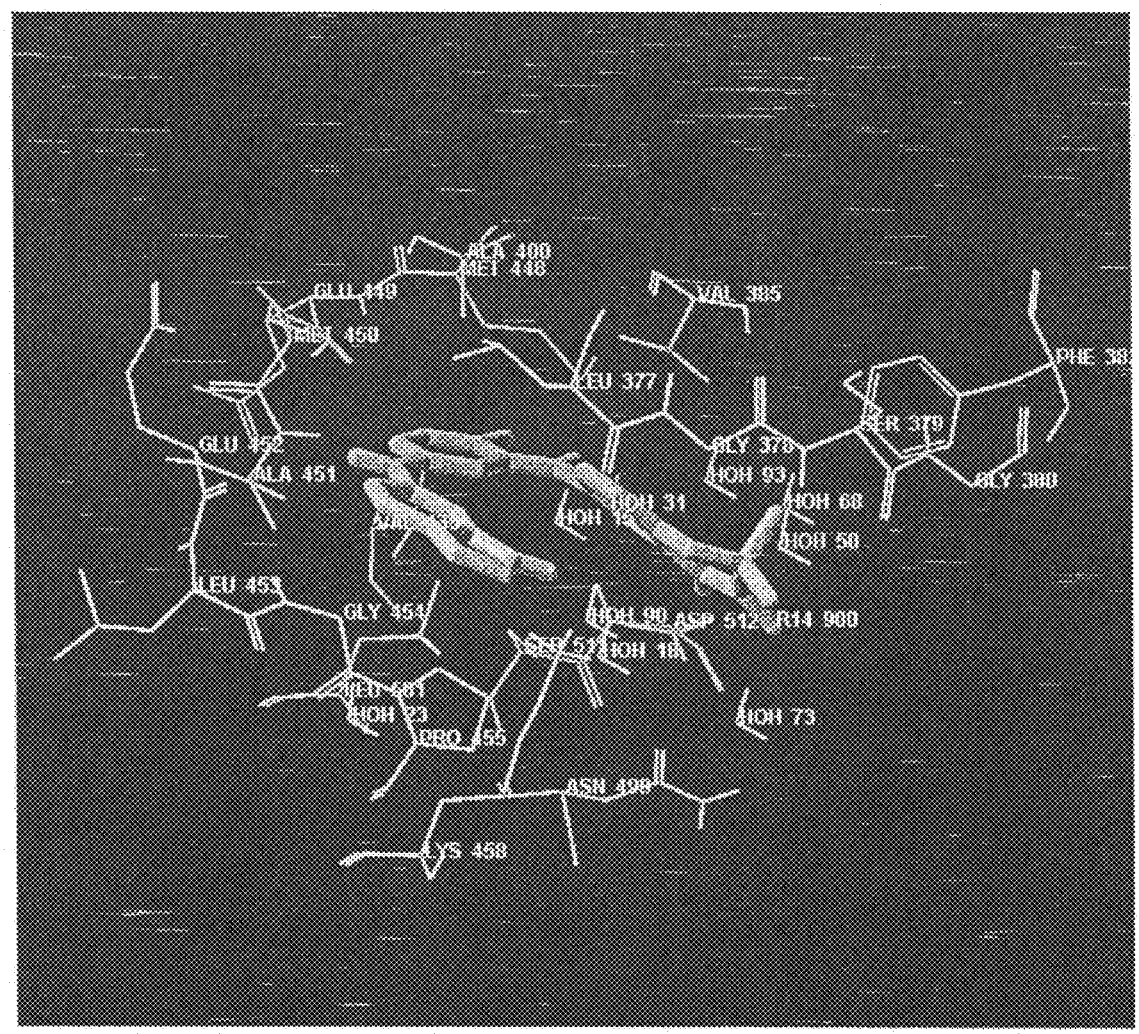
FIG. 26 illustrates the co-crystals of SYK with Cpd. No. 6.

The structure was solved by molecular replacement using MOLREP version 8.2. The previously determined crystal structure of SYK kinase E440Q containing Cpd. No. 1, refined to 2.0 Å, served as the search model. The structure was refined with Refmac5 version 5.2 using data from 30 Å to 2.0 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 6. The electron density was well-defined for the entire ligand. The Cpd. No. 6 inhibitor was included in the final refinement along with 103 water molecules. Cpd. No. 6 forms non-bonded contacts with Ala 451, Lys 458, Asp512 and water molecules #31 and 73. See FIGS. 17-18 and 26 for the three-dimensional structure results. The three-dimensional coordinates are listed in Table 4 in the file entitled 05-689 Table 4.txt in CD-R 1. The non-bonded contacts are enumerated in Table I. Refinement statistics are provided in Table J.

TABLE I

Non-Bonded Contacts Between SYK E440Q and Cpd. No. 6

| RGE14 Atom | Protein or Water Atom | Distance (Å) |
|---|---|---|
| N2 | Ala 451 N | 3.06 |
| N4 | Ala 451 O | 2.98 |
| N7 | Lys 458 NZ | 2.98 |
| N5 | Asp512 OD1 | 2.91 |
| F1 | Water O31 | 3.15 |
| N3 | Water O31 | 3.07 |
| O2 | Water O73 | 2.81 |

TABLE J

Crystallographic Data for SYK Kinase E440Q Containing Cpd. No. 6

| Data Collection | |
|---|---|
| Unit Cell (Å) | a = 39.91 |
|  | b = 85.15 |
|  | c = 90.68 |
| Space group | $P2_1 2_1 2_1$ |
| Resolution (Å) | 50.0 – 2.0 |
| Wavelength (Å) | 0.97934 |
| Total Reflections | 107,508 |
| Unique Reflections | 20,602 |
| I/(sigI)* | 14.5 (1.7) |
| $R_{merge}$ (%)* | 10.0 (52.4) |
| Completeness (%)* | 94.6 (88.6) |
| Refinement | |
| Resolution (Å) | 30.0 – 2.0 |
| Unique Reflections (working/test) | 19,364/1059 |
| $R_{working}/R_{free}$ (%) | 22.0/28.0 |
| Number of atoms (protein/ligand/water) | 2154/31/103 |
| r.m.s. deviation bond length (Å) | 0.01 |
| r.m.s. deviation bond angle (degrees) | 1.4 |
| Mean B factor all (Å$^2$) | 34.0 |
| Mean B factor protein (Å$^2$) | 34.1 |
| Mean B factor ligand (Å$^2$) | 24.9 |
| Mean B factor water (Å$^2$) | 35.5 |
| r.m.s. positional (Å) | 0.22 |
| Ramachandran Analysis (%) | |
| Most Favored | 93.2 |
| Additionally Allowed | 6.4 |
| Generously Allowed | 0.4 |

*Parentheses indicate values for the 2.07 Å to 2.00 Å resolution shell.

Example 6

Crystal Structure of SYK Kinase (1358-N635) Containing Bound Cpd. No. 3 Refined to 2.3 Å

Expression and Purification

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 µm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

Crystallization

The pooled fractions were dialyzed against 300 mM NaCl, 10 mM Hepes pH 7.5, 5 mM DTT, 10% glycerol overnight at 4° C. then concentrated to 10.0 mg/mL in a Vivaspin centrifugal concentrator (MWCO=10 kDa). Crystals were obtained at 20° C. in sitting drop plates using 1 µl of protein and 1 µl of crystallant (20% PEG 3000, 100 mM Citrate pH 5.5) equilibrated against 200 µl of crystallant in the reservoir. Plate-shaped crystals were observed after approximately 24 hours. A single crystal was transferred from the crystallization drop to a plate containing 30% PEG 3000, 50 mM Citrate pH 5.5, 5% DMSO and 2.4 mM RGE1. The crystal was soaked for 23.5 hours in this solution. Some precipitation of Cpd. No. 3 was observed therefore the concentration of the ligand in solution was less than 2.4 mM. The crystal was transferred to a cryoprotectant containing 20% PEG 3000, 100 mM Citrate pH 5.5, 15% glycerol then plunge frozen into liquid nitrogen for X-ray diffraction analysis.

Data Collection and Processing

Data were collected at the Advanced Photon Source (APS) Structural Biology Center (SBC) beamline 19-BM, located at Argonne National Laboratory, using a custom built CCD detector and 1° ω-scans. The X-ray wavelength was 0.97934 Å. Intensities were integrated and scaled with the HKL2000 package. Indexing indicated a primitive orthorhombic lattice with a=39.94 Å, b=85.24, c=91.02 Å and the space group was determined to be P $2_1 2_1 2_1$ based upon systematic absences h00; h=2n, 0k0; k=2n; 001; 1=2n.

Structure Solution and Refinement

Figure 15:
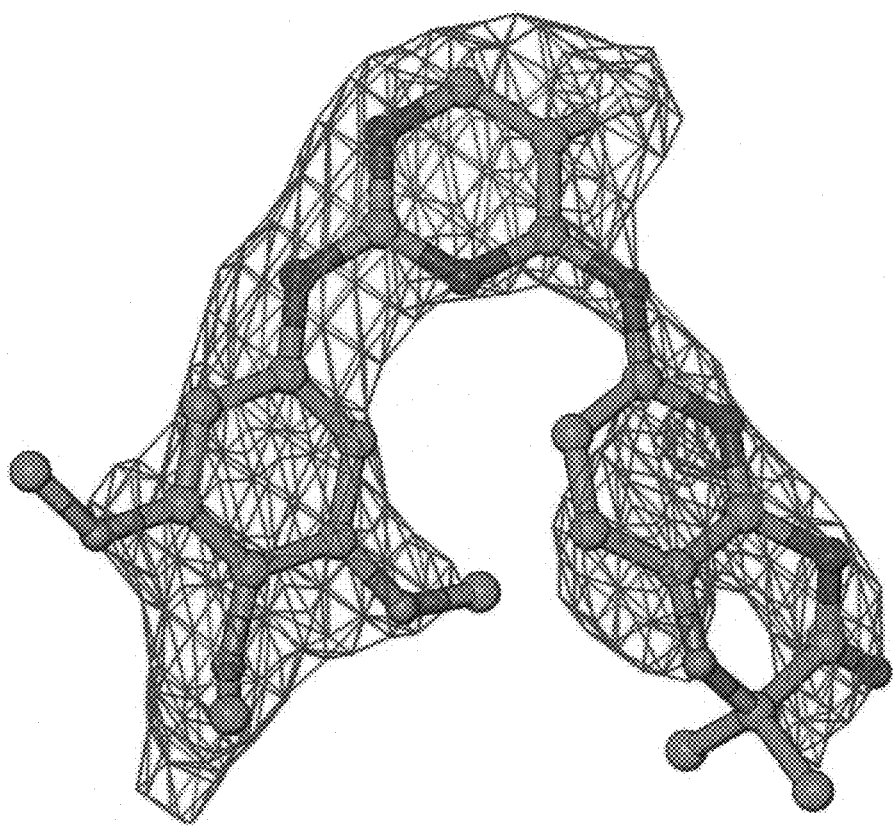
FIG. 15 illustrates the calculated Fo-Fc omit map of Cpd. No. 3 contoured at 2.5σ.
Figure 16:
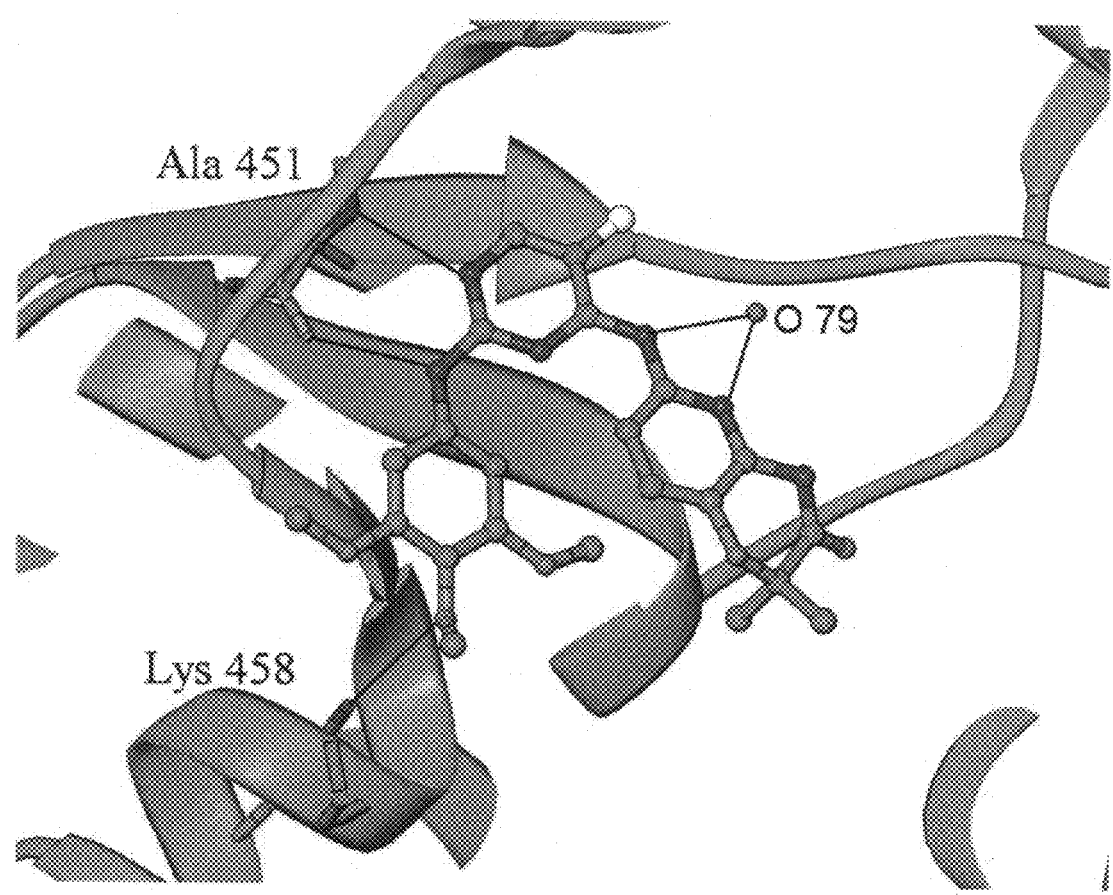
FIG. 16 illustrates the non-bonded interactions between Cpd. No. 3, SYK kinase and water molecules
Figure 23:
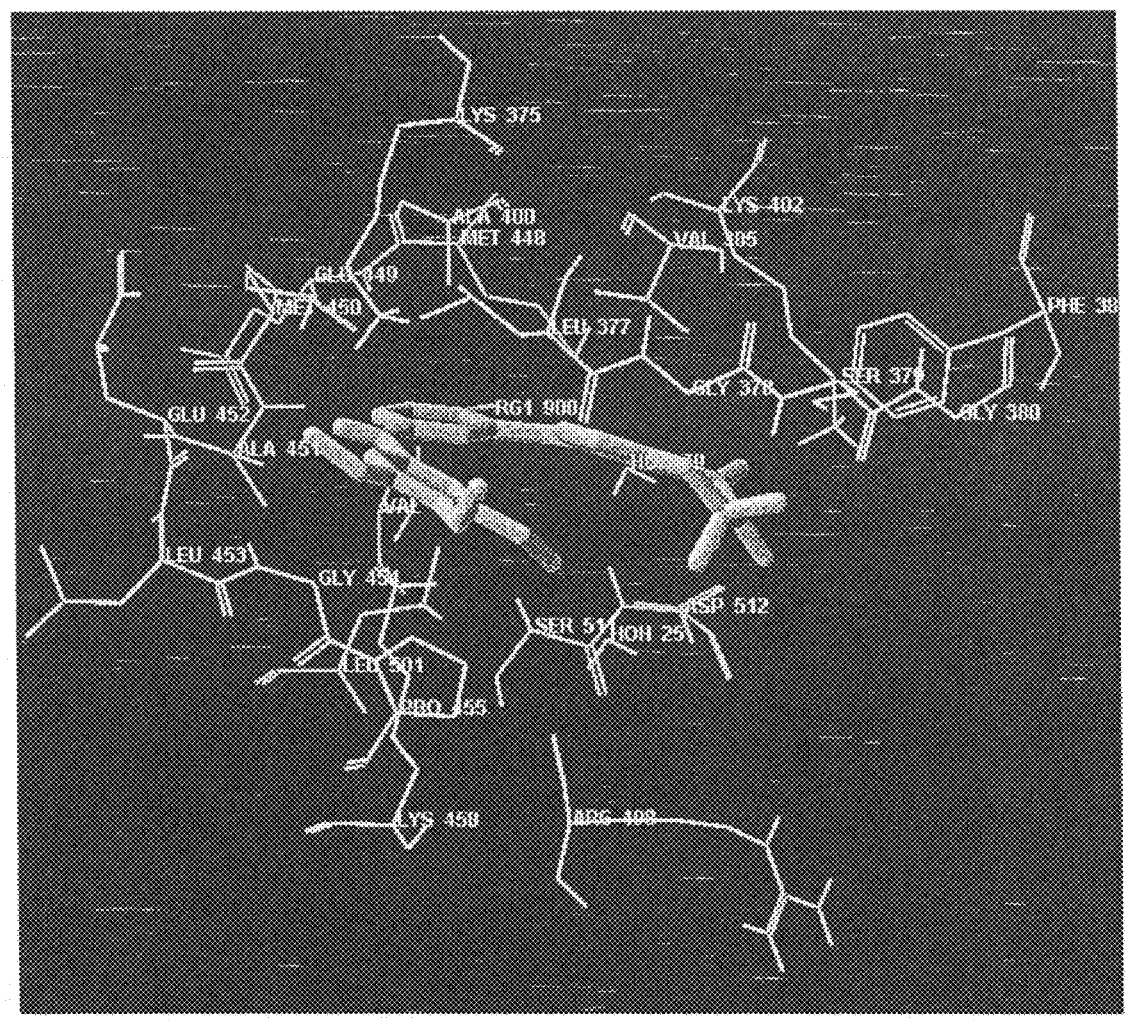
FIG. 23 illustrates the co-crystals of SYK with Cpd. No. 3.
Figure 24:
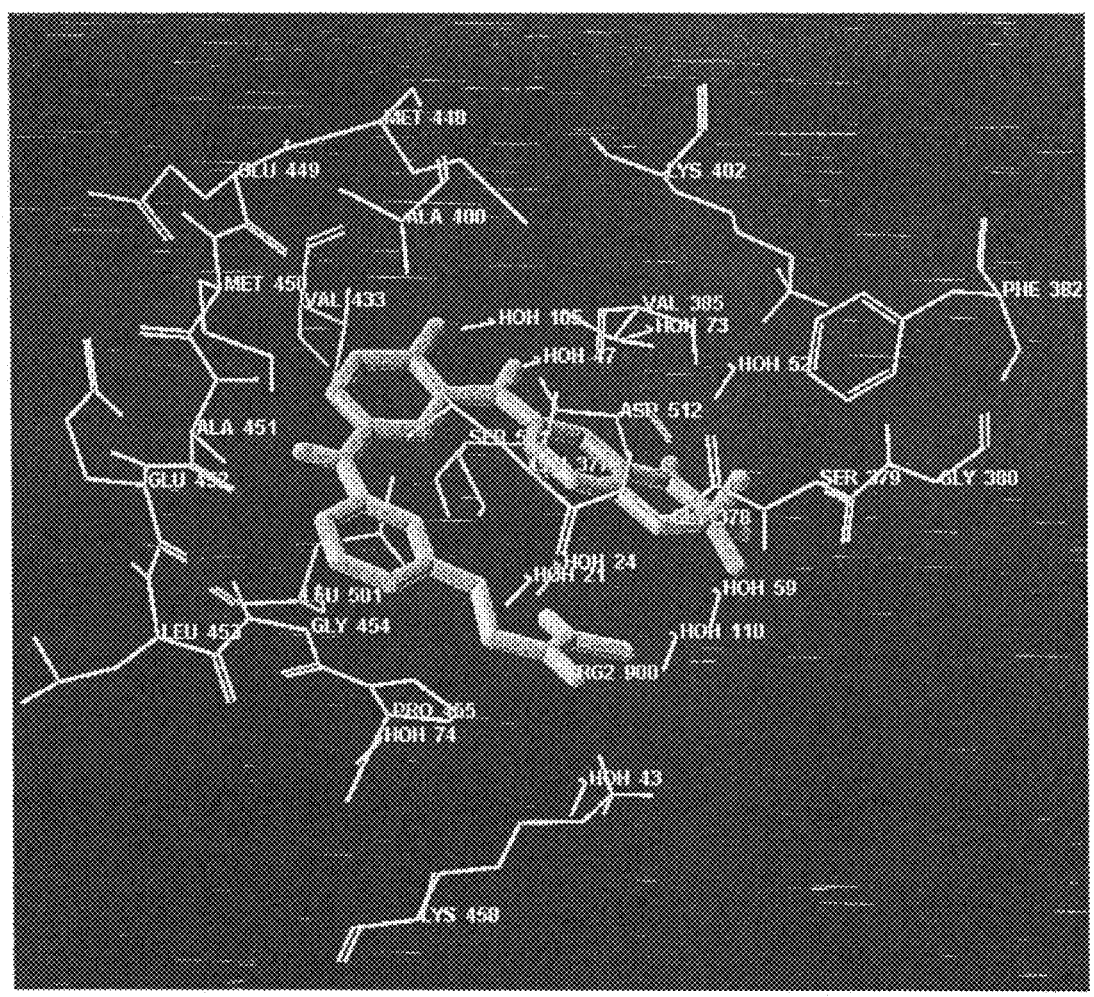
FIG. 24 illustrates the co-crystals of SYK with Cpd. No. 5.

The structure was solved by molecular replacement using MOLREP version 8.2. The previously determined crystal structure of SYK kinase E440Q containing Cpd. No. 3, refined to 2.0 Å, served as the search model. The structure was refined with Refmac5 version 5.2 using data from 30 Å to 2.3 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 3. However, the electron density for the portion of the ligand containing the aliphatic ring fused to the pyridine was not well defined. This was likely due to thermal motion at this site. The Cpd. No. 3 inhibitor was included in the final refinement along with 82 water molecules. Cpd. No. 3 forms non-bonded contacts with Ala 451, Lys 458 and water molecule (#79) and are enumerated in the table below. See FIGS. 15-16 and 23 for the three-dimensional structure results. The three-dimensional coordinates are listed in Table 5 in the file entitled 05-689 Table 5.txt in CD-R 1. The non-bonded contacts are enumerated in Table K. Refinement statistics are provided in Table L.

TABLE K

Non-Bonded Contacts Between SYK E440Q and Cpd. No. 3

| RGE1 Atom | Protein or Water Atom | Distance (Å) |
|---|---|---|
| N2 | Ala 451 N | 2.93 |
| N6 | Ala 451 O | 3.06 |
| O3 | Lys 458 NZ | 2.96 |
| N3 | Water O79 | 2.70 |
| N5 | Water O79 | 2.85 |

TABLE L

Crystallographic Data for SYK Kinase E440Q Containing Cpd. No. 3

| Data Collection | |
|---|---|
| Unit Cell (Å) | a = 39.94 |
| | b = 85.24 |
| | c = 91.02 |
| Space group | $P2_12_12_1$ |
| Resolution (Å) | 50.0 – 2.3 |
| Wavelength (Å) | 0.97934 |
| Total Reflections | 60,686 |
| Unique Reflections | 14,289 |
| I/(sigI)* | 13.2 (2.1) |
| $R_{merge}$ (%)* | 10.3 (41.7) |
| Completeness (%)* | 97.5 (94.5) |
| Refinement | |
| Resolution (Å) | 30.0 – 2.3 |
| Unique Reflections (working/test) | 13,353/702 |
| $R_{working}/R_{free}$ (%) | 20.9/28.2 |
| Number of atoms (protein/ligand/water) | 2154/34/82 |
| r.m.s. deviation bond length (Å) | 0.01 |
| r.m.s. deviation bond angle (degrees) | 1.4 |
| Mean B factor all (Å$^2$) | 39.6 |
| Mean B factor protein (Å$^2$) | 39.5 |
| Mean B factor ligand (Å$^2$) | 50.1 |
| Mean B factor water (Å$^2$) | 38.3 |
| r.m.s. positional (Å) | 0.36 |
| Ramachandran Analysis (%) | |
| Most Favored | 92.7 |
| Additionally Allowed | 6.8 |
| Generously Allowed | 0.4 |

*Parentheses indicate values for the 2.38 Å to 2.30 Å resolution shell.

Example 7

Crystal Structure of SYK Kinase (1358-N635) Containing Bound Cpd. No. 2 Refined to 2.0 Å

Expression and Purification

The cells were thawed at room temperature then resuspended in 5 times (v/w) of lysis buffer containing 150 mM NaCl, 50 mM Tris pH 8.0, 10% glycerol, 200 mM Arginine, 0.2% Igepal-630. The cells were lysed for 20 minutes on ice then sonicated with a 15 second pulse at 40% power. After pelleting the insoluble material for 30 minutes at 17,000 rpm, the supernatant was filtered through a 5 μm syringe filter and loaded onto a 5 mL His-Trap HP chelating column (Pharmacia) at 0.5 mL/min. The column was then washed with ~4 column volumes of buffer A (500 mM NaCl, 20 mM Tris (pH 8.0), 10% glycerol). A linear gradient from 0% to 10% buffer B (500 mM NaCl, 20 mM Tris pH (8.0), 20% glycerol, 500 mM Imidazole) was applied to the column to remove non-specifically bound impurities. The protein was eluted with a linear gradient up to 50% buffer B. The protein began to elute at ~130 mM imidazole. Elution fractions were analyzed by SDS-PAGE, which indicated that the protein was sufficiently pure for crystallization experiments.

The Kinase domain of spleen tyrosine kinase (SYK) encompassing amino acid residues 1358 to N635 with the single mutation E440Q and a C-terminal rTEV-hexahisdine purification tag was created using whole gene synthesis. The synthetic construct was cloned into the BacloDirect (Invitrogen) entry vector for expression in SF9 cells. Following transfection, viral amplification was carried out for 3-days at 27° C. at the 10-liter scale. The SF9 cells were harvested and flash frozen in liquid nitrogen until ready for use.

Crystallization

The pooled fractions were dialyzed against 300 mM NaCl, 10 mM Hepes pH 7.5, 5 mM DTT, 10% glycerol overnight at 4° C. then concentrated to 10.0 mg/mL in a Vivaspin centrifugal concentrator (MWCO=10 kDa). Crystals were obtained at 20° C. in sitting drop plates using 1 μl of protein and 1 μl of crystallant (20% PEG 3000, 100 mM Citrate pH 5.5, 5% DMSO and 1.1 mM Cpd. No. 2) equilibrated against 200 μl of crystallant in the reservoir. Plate-shaped crystals were observed after approximately 24 hours. Crystals was transferred to a cryoprotectant containing 20% PEG 3000, 100 mM Citrate pH 5.5, 15% glycerol then plunge frozen into liquid nitrogen for X-ray diffraction analysis.

Data Collection and Processing

Data were collected at the Advanced Photon Source (APS) Structural Biology Center (SBC) beamline 19-BM, located at Argonne National Laboratory, using a custom built CCD detector and 1° ω-scans. The X-ray wavelength was 0.97934 Å. Intensities were integrated and scaled with the HKL2000 package. Indexing indicated a primitive orthorhombic lattice with a=39.70 Å, b=85.52, c=89.84 Å and the space group was determined to be $P\,2_12_12_1$ based upon systematic absences h00; h=2n, 0k0; k=2n; 001; 1-2n.

Structure Solution and Refinement

Figure 13:
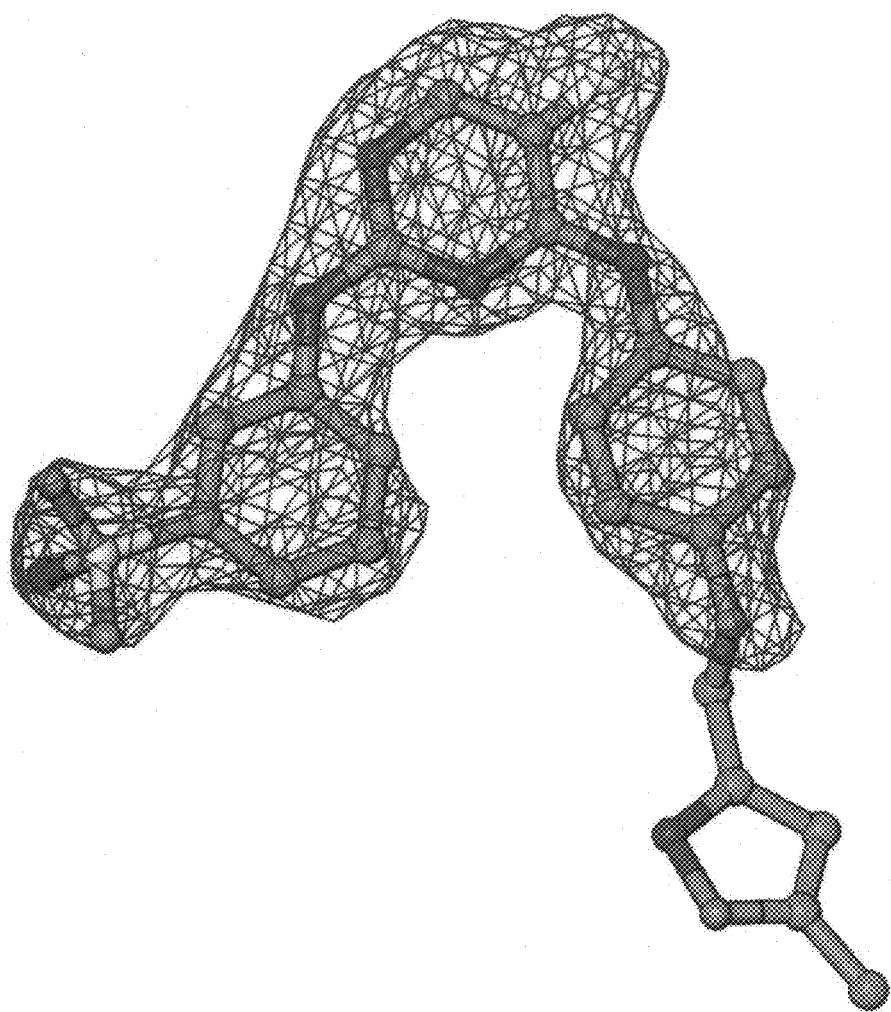
FIG. 13 illustrates the calculated Fo-Fc omit map of Cpd. No. 2 contoured at 2.5σ.
Figure 14:
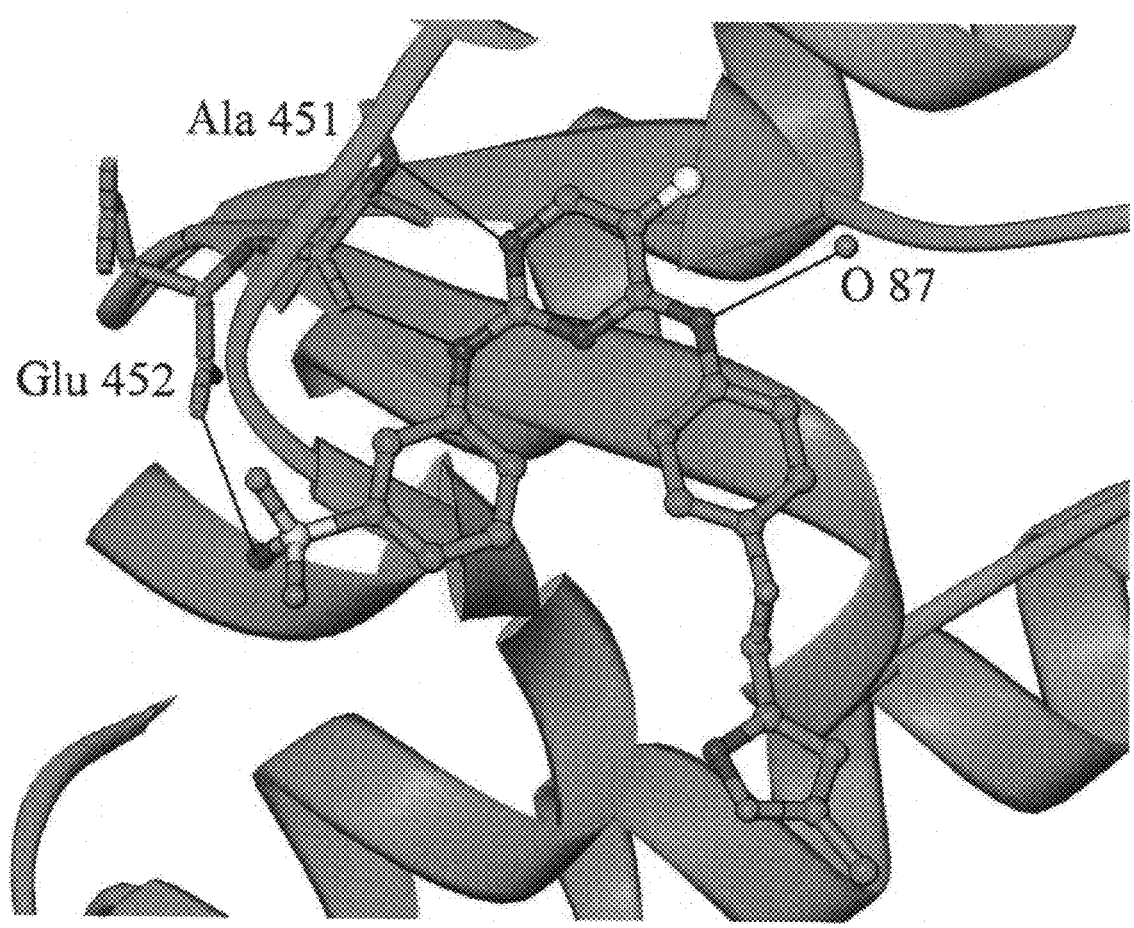
FIG. 14 illustrates the non-bonded interactions between Cpd. No. 2, SYK kinase and water molecules.

The structure was solved by molecular replacement using MOLREP version 8.2. The previously determined crystal structure of SYK kinase E440Q containing Cpd. No. 1, refined to 2.0 Å, served as the search model. The structure was refined with Refmac5 version 5.2 using data from 30 Å to 2.0 Å resolution and model building was carried out with O. Residues Val 363 to Asn 635 were discernable in the electron density maps except for Lys 393, Lys394 and Lys 405 to Asp 410 which were disordered and could not be fit to the electron density. Examination of the ATP binding pocket revealed difference electron density consistent with compound Cpd. No. 2. The electron density was well-defined for most of the ligand. However, atoms C17, 18, 19, 20, 21, N5 and O2 could not be discerned most likely due to disorder. The heterocyclic ring containing these atoms is situated in a solvent channel where it is free to rotate. This is most likely the source of the disorder. The Cpd. No. 2 inhibitor was included in the final refinement along with 119 water molecules. The disordered atoms in Cpd. No. 2 were refined with 0.5 occupancy factors. Cpd. No. 2 forms non-bonded contacts with Ala 451, Glu 452 and water molecule #87. See FIGS. 13-14 for the three-dimensional structure results. The three-dimensional coordinates are listed in Table 6 in the file entitled 05-689 Table 6.txt in CD-R 1. The non-bonded contacts are enumerated in Table M. Refinement statistics are provided Table N.

TABLE M

Non-Bonded Contacts Between SYK E440Q and Cpd. No. 2

| RGE15 Atom | Protein or Water Atom | Distance (Å) |
|---|---|---|
| N2 | Ala 451 N | 2.99 |
| N4 | Ala 451 O | 2.88 |

TABLE M-continued

Non-Bonded Contacts Between SYK E440Q and Cpd. No. 2

| RGE15 Atom | Protein or Water Atom | Distance (Å) |
|---|---|---|
| N6 | Glu 452 O | 3.09 |
| N3 | Water O87 | 3.16 |

TABLE N

Crystallographic Data for SYK Kinase E440Q Containing Cpd. No. 2

| Data Collection | |
|---|---|
| Unit Cell (Å) | a = 39.39 |
|  | b = 85.52 |
|  | c = 89.84 |
| Space group | P2$_1$2$_1$2$_1$ |
| Resolution (Å) | 50.0 – 2.0 |
| Wavelength (Å) | 0.97934 |
| Total Reflections | 136,389 |
| Unique Reflections | 21,291 |
| I/(sigI)* | 18.3 (2.2) |
| R$_{merge}$ (%)* | 7.3 (2.2) |
| Completeness (%)* | 98.6 (96.4) |
| Refinement | |
| Resolution (Å) | 30.0 – 2.0 |
| Unique Reflections (working/test) | 19,996/1080 |
| R$_{working}$/R$_{free}$ (%) | 21.2/26.3 |
| Number of atoms (protein/ligand/water) | 2154/33/119 |
| r.m.s. deviation bond length (Å) | 0.01 |
| r.m.s. deviation bond angle (degrees) | 1.4 |
| Mean B factor all (Å$^2$) | 29.9 |
| Mean B factor protein (Å$^2$) | 29.7 |
| Mean B factor ligand (Å$^2$) | 33.4 |
| Mean B factor water (Å$^2$) | 33.2 |
| r.m.s. positional (Å) | 0.22 |

TABLE N-continued

Crystallographic Data for SYK Kinase E440Q Containing Cpd. No. 2

| Ramachandran Analysis (%) | |
|---|---|
| Most Favored | 91.5 |
| Additionally Allowed | 8.5 |
| Generously Allowed | — |

*Parentheses indicate values for the 2.07 Å to 2.00 Å resolution shell.

The present invention is not to be limited in scope by the exemplified embodiments and examples, which are intended merely as illustrations of some aspects of the invention. Various modifications of the invention in addition to those described herein will become apparent to those having skill in the art from the foregoing description and accompanying drawings. Such modifications are intended to fall within the scope of the invention. References cited throughout this application illustrate the level of skill in the art and are hereby incorporated by reference in their entirety, whether previously specifically incorporated or not.

REFERENCES

1. Z. Otwinowski and W. Minor, "Processing of X-ray Diffraction Data Collected in Oscillation Mode", *Methods in Enzymology*, Volume 276: Macromolecular Crystallography, part A, p. 307-326, (1997), C. W. Carter, Jr. & R. M. Sweet, Eds., Academic Press (New York).
2. A. A. Vagin and A. Teplyakov, *J. Appl. Cryst.*, 30, 1022, (1997).
3. S. Atwell, J. M Adams, J. Badger, M. D. Buchanan, I. K. Feil, K. J. Froning, X. Gao, J. Hendle, K. Keegan, B. C. Leon, H. J. Muller-Dieckmann, V. L Nienaber, B. W. Noland, K. Post, K. R. Rajashankar, A. Ramos, M. Russell, S. K. Burley and S. G. Buchanan, J. Biol. Chem., 279, 55827, (2004).
4. A. A. Vagin and E. J. Dodson, in Acta Cryst. D53, 240, (1997).
5. T. A Jones, J. Y Zou, S. W. Cowan, and M. Kjeldgaard, Acta. Cryst. A47, 110, (1991).

---

What is claimed is:

1. A method of constructing a spleen tyrosine kinase (SYK) inhibitor pharmacophore comprising:
   (a) generating on a computer a set of three-dimensional conformers comprising a binding site of SYK and compounds from a training set comprising one or more SYK ligands for the binding site, wherein the three-dimensional conformers are generated by using the coordinates of the SYK binding site as set forth in any one of Tables 1 to 6 and the conformers comprise residues selected from the group consisting of Leu377, Gly378, Phe382, Val385, Ala400, Val433, Met448, Glu449, Met450, Ala451, Glu452, Gly454, Pro455, Lys458, Leu501, Asp512, Lys375, Ser379, Gly380, Gly383, Thr384, Lys402, Leu453, Arg498, Asn499, and Ser511 or any combinations thereof, wherein the amino acid numbering is of SEQ ID NO: 1;
   (b) using the conformers generated in (a) to identify on a computer one or more features on the ligands, wherein the features comprise groups that interact with the residues lining the binding site;
   (c) formulating (i) by chemical synthesis or (ii) on a computer a set of one or more pharmacophores from the conformers of (a), each of the pharmacophore comprising one or more features identified in (b); and
   (d) determining
      (i) by testing the chemically synthesized pharmacophores for their ability to bind to SYK, or
      (ii) on a computer
   those pharmacophores that bind to SYK
   wherein the training set comprises one or more compounds having the structure:

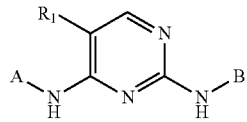

wherein
   A and B are independently aryl or heteroaryl, wherein each of the aryl and heteroaryl is optionally substituted with one or more groups selected from —OH, —S(O)$_{0-2}$—NH$_2$, C$_1$-C$_6$ alkyl, oxo, halo, and C$_1$-C$_6$ alkyloxy; and
   $R_1$ is halo.

2. The method of claim 1, wherein the three-dimensional conformers are generated by using the coordinates from co-crystals of SYK and SYK ligands.

3. The method of claim 1, wherein the SYK comprising the fragment from Ile358 to Asn635 of SEQ ID NO: 1.

4. The method of claim 3, wherein the SYK fragment comprises the mutation Glu440Gln.

5. The method of claim 1, wherein the three-dimensional conformers are generated by using the coordinates of the SYK binding site and the SYK ligands from any one of Tables 1 to 6.

6. The method of claim 1, wherein the features are selected from the group consisting of a hydrogen bond donor, a hydrogen bond acceptor, a hydrophobic region, a hydrophilic region, a ionizable region, and an aromatic ring, wherein the features are arranged in three-dimensional space and interact with the residues lining the binding site.

7. The method of claim 1, wherein the step of formulating a pharmacophore comprises measuring the distances separating the features.

8. The method of claim 1, wherein the step of formulating a pharmacophore comprises measuring the angles separating the features.

9. The method of claim 1, wherein the step of formulating a pharmacophore comprises measuring the distances and angles separating the features.

10. The method of claim 1, wherein the steps are carried out using molecular modeling software.

11. The method of claim 1, wherein the training set of SYK ligands comprises compounds that are SYK inhibitors with $IC_{50}$ values of 500 nM or less.

12. The method of claim 1, wherein the training set comprises at least three compounds.

13. The method of claim 1, wherein the training set comprises at least six compounds.

14. The method of claim 1, wherein the training set comprises one or more compounds selected from the group consisting of:

Cpd. No. 1

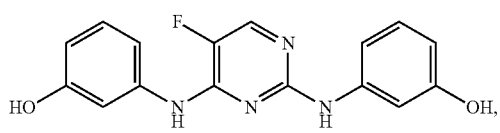

Cpd. No. 2

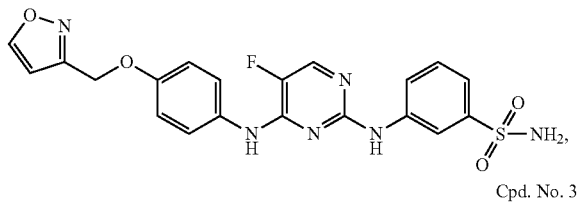

Cpd. No. 3

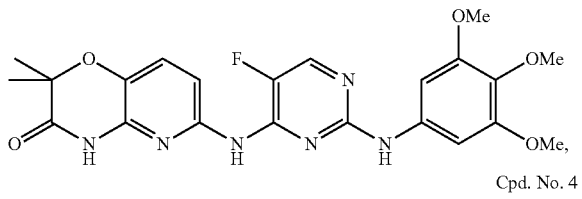

Cpd. No. 4

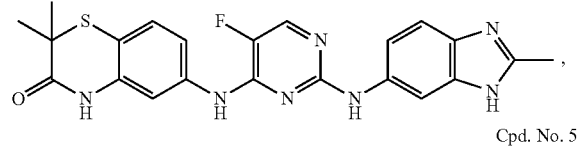

Cpd. No. 5

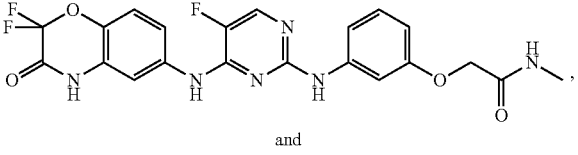

and

Cpd. No. 6

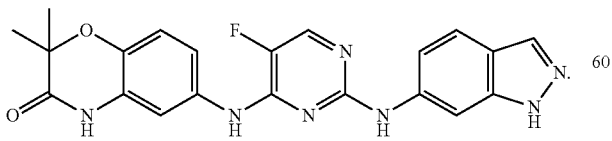

15. The method of claim 1, wherein the conformer comprises a hydrophobic core comprising Met448, Ala400, Val433, Met448, Glu449, Met450, Ala451, and Leu501, wherein Met448 interacts with a hydrophobic region or an aromatic ring of the ligand, wherein the amino acid numbering is of SEQ ID NO: 1.

16. The method of claim 1, wherein the backbone carbonyl group of Glu449 and Ala451 act as hydrogen bond acceptors from the ligand, wherein the amino acid numbering is of SEQ ID NO: 1.

17. The method of claim 1, wherein the backbone amine group of Ala451 act as hydrogen bond donors to the ligand, wherein the amino acid numbering is of wild type SYK.

18. The method of claim 1, wherein the conformer comprises a hydrophobic core comprising Leu377, Gly378, Phe382, and Val385, wherein the amino acid numbering is of SEQ ID NO: 1.

19. The method of claim 1, wherein the conformer comprises a hydrophobic core comprising Leu377, Met450, Ala451, Glu452, Gly454, Pro455, and Leu501, wherein the amino acid numbering is of SEQ ID NO: 1.

20. The method of claim 1, wherein the carboxyl group of Asp512 acts as a hydrogen bond acceptor from the ligand, wherein the amino acid numbering is of SEQ ID NO: 1.

21. The method of claim 1, wherein the amine of Lys458 acts as one or more hydrogen bond donor to the ligand, wherein the amino acid numbering is of SEQ ID NO: 1.

22. The method of claim 1, wherein the binding site in the conformer is surrounded by Val433, Met448, Asp512 and a ligand, wherein the binding site comprises one or more water molecules and the amino acid numbering is of SEQ ID NO: 1.

23. The method of claim 1, wherein Arg498 and Asn499 forms a hydrophilic region, wherein the hydrophilic region contributes to ligand selectivity, and wherein the amino acid numbering is of SEQ ID NO: 1.

24. A method for screening for spleen tyrosine kinase (SYK) inhibitors comprising:
(a) generating on a computer a set of three-dimensional conformers comprising a binding site of SYK and compounds from a training set comprising a plurality of SYK inhibitors, wherein the three-dimensional conformers are generated by using the coordinates of the SYK binding site as set forth in any one of Tables 1 to 6 and the conformers comprise residues selected from the group consisting of Leu377, Gly378, Phe382, Val385, Ala400, Val433, Met448, Glu449, Met450, Ala451, Glu452, Gly454, Pro455, Lys458, Leu501, Asp512, Lys375, Ser379, Gly380, Gly383, Thr384, Lys402, Leu453, Arg498, Asn499, and Ser511 or any combinations thereof, wherein the amino acid numbering is of SEQ ID NO: 1;
(b) formulating on a computer a set of one or more pharmacophores from the conformers of (a), the pharmacophores comprising one or more features; and
(c) providing on a computer a set of one or more compounds that are possible SYK inhibitors;
(d) comparing on a computer the compound(s) with the pharmacophore(s) and maximizing the fit of the compound(s) to the pharmacophores; and
(e) identifying on a computer one or more compounds that fit the constraints imposed by the pharmacophore(s), each of the constraints of the pharmacophore(s) being defined by at least one pharmacophore feature; and
(f) determining the ability of the compound(s) to bind SYK.

25. The method of claim 24, wherein finding the optimum fit in step (d) is carried out using a molecular modeling software.

26. The method of claim 24, wherein the inhibitors comprises compounds having the structure:

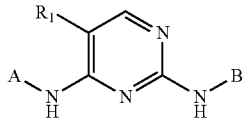

wherein
  A and B are independently aryl or heteroaryl, wherein each of the aryl and heteroaryl is optionally substituted with one or more groups selected from —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, mono- to perhalogenated C$_1$-C$_6$ alkyl, mono- to perhalogenated C$_1$-C$_6$ alkyloxy, —S(O)$_2$—NH$_2$, —S(O)$_2$—N(H)—C$_1$-C$_6$ alkyl, —S(O)$_2$—N(C$_1$-C$_6$ alkyl)$_2$, C$_1$-C$_6$ alkyl, oxo, halo, and C$_1$-C$_6$ alkyloxy; and
  R$_1$ is halo, —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, C$_1$-C$_6$ alkyl, C$_1$-C$_6$ alkyloxy, mono- to perhalogenated C$_1$-C$_6$ alkyl, and mono- to perhalogenated C$_1$-C$_6$ alkyloxy.

27. A method for inhibiting SYK comprising contacting SYK with a compound identified according to claim 24.

28. The method of claim 27, wherein the inhibitors comprises compounds having the structure:

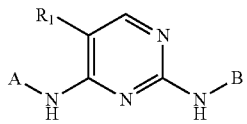

wherein
  A and B are independently aryl or heteroaryl, wherein each of the aryl and heteroaryl is optionally substituted with one or more groups selected from —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, mono- to perhalogenated C$_1$-C$_6$ alkyl, mono- to perhalogenated C$_1$-C$_6$ alkyloxy, —S(O)$_2$—NH$_2$, —S(O)$_2$—N(H)—C$_1$-C$_6$ alkyl, —S(O)$_2$—N(C$_1$-C$_6$ alkyl)$_2$, C$_1$-C$_6$ alkyl, oxo, halo, and C$_1$-C$_6$ alkyloxy; and
  R$_1$ is halo, —OH, —NH$_2$, —N(H)—C$_1$-C$_6$ alkyl, —N(C$_1$-C$_6$ alkyl)(C$_1$-C$_6$ alkyl), —SH, —S—C$_1$-C$_6$ alkyl, —CN, C$_1$-C$_6$ alkyl, C$_1$-C$_6$ alkyloxy, mono- to perhalogenated C$_1$-C$_6$ alkyl, and mono- to perhalogenated C$_1$-C$_6$ alkyloxy.

29. The method of claim 27, wherein the features are selected from the group consisting of a hydrogen bond donor, a hydrogen bond acceptor, a hydrophobic region, a ionizable region and an aromatic ring, wherein the features are arranged in three-dimensional space and interact with the residues lining the binding site.

* * * * *

SEQUENCE LISTING

```
<160> NUMBER OF SEQ ID NOS: 1

<210> SEQ ID NO 1
<211> LENGTH: 291
<212> TYPE: PRT
<213> ORGANISM: Homo sapiens

<400> SEQUENCE: 1

Met Ala Leu Glu Glu Ile Arg Pro Lys Glu Val Tyr Leu Asp Arg Lys
1               5                   10                  15

Leu Leu Thr Leu Glu Asp Lys Glu Leu Gly Ser Gly Asn Phe Gly Thr
            20                  25                  30

Val Lys Lys Gly Tyr Tyr Gln Met Lys Lys Val Val Lys Thr Val Ala
        35                  40                  45

Val Lys Ile Leu Lys Asn Glu Ala Asn Asp Pro Ala Leu Lys Asp Glu
    50                  55                  60

Leu Leu Ala Glu Ala Asn Val Met Gln Gln Leu Asp Asn Pro Tyr Ile
65                  70                  75                  80

Val Arg Met Ile Gly Ile Cys Glu Ala Glu Ser Trp Met Leu Val Met
                85                  90                  95

Glu Met Ala Glu Leu Gly Pro Leu Asn Lys Tyr Leu Gln Gln Asn Arg
```

```
                     100                 105                 110
His Val Lys Asp Lys Asn Ile Ile Glu Leu Val His Gln Val Ser Met
        115                 120                 125

Gly Met Lys Tyr Leu Glu Glu Ser Asn Phe Val His Arg Asp Leu Ala
        130                 135                 140

Ala Arg Asn Val Leu Leu Val Thr Gln His Tyr Ala Lys Ile Ser Asp
145                 150                 155                 160

Phe Gly Leu Ser Lys Ala Leu Arg Ala Asp Glu Asn Tyr Tyr Lys Ala
                165                 170                 175

Gln Thr His Gly Lys Trp Pro Val Lys Trp Tyr Ala Pro Glu Cys Ile
            180                 185                 190

Asn Tyr Tyr Lys Phe Ser Ser Lys Ser Asp Val Trp Ser Phe Gly Val
        195                 200                 205

Leu Met Trp Glu Ala Phe Ser Tyr Gly Gln Lys Pro Tyr Arg Gly Met
        210                 215                 220

Lys Gly Ser Glu Val Thr Ala Met Leu Glu Lys Gly Glu Arg Met Gly
225                 230                 235                 240

Cys Pro Ala Gly Cys Pro Arg Glu Met Tyr Asp Leu Met Asn Leu Cys
                245                 250                 255

Trp Thr Tyr Asp Val Glu Asn Arg Pro Gly Phe Ala Ala Val Glu Leu
            260                 265                 270

Arg Leu Arg Asn Tyr Tyr Tyr Asp Val Val Asn Glu Gly His His His
        275                 280                 285

His His His
    290
```